United States Patent
Ueng et al.

(10) Patent No.: US 9,827,228 B2
(45) Date of Patent: Nov. 28, 2017

(54) OPIOID RECEPTOR MODULATORS AND USE THEREOF

(71) Applicants: National Health Research Institutes, Zhunan Town (TW); Regents of the University of Minnesota, Minneapolis, MN (US)

(72) Inventors: Shau-Hua Ueng, Zhunan (TW); Shiu-Hwa Yeh, Zhunan (TW); Horace Loh, Little Canada, MN (US); Yu-Sheng Chao, New York, NY (US)

(73) Assignees: National Health Research Institutes, Zhunan Town (TW); Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/207,951

(22) Filed: Jul. 12, 2016

(65) Prior Publication Data

US 2017/0056377 A1    Mar. 2, 2017

Related U.S. Application Data

(60) Provisional application No. 62/212,145, filed on Aug. 31, 2015.

(51) Int. Cl.

| | | |
|---|---|---|
| *A61K 31/5377* | (2006.01) | |
| *A61K 31/422* | (2006.01) | |
| *A61K 31/428* | (2006.01) | |
| *A61K 31/485* | (2006.01) | |
| *A61K 31/427* | (2006.01) | |
| *A61K 31/4439* | (2006.01) | |
| *G01N 33/50* | (2006.01) | |
| *A61K 31/426* | (2006.01) | |
| *A61K 31/454* | (2006.01) | |
| *G01N 33/94* | (2006.01) | |

(52) U.S. Cl.
CPC .......... *A61K 31/426* (2013.01); *A61K 31/422* (2013.01); *A61K 31/427* (2013.01); *A61K 31/428* (2013.01); *A61K 31/4439* (2013.01); *A61K 31/454* (2013.01); *A61K 31/485* (2013.01); *A61K 31/5377* (2013.01); *G01N 33/9486* (2013.01); *G01N 2500/04* (2013.01); *G01N 2500/10* (2013.01)

(58) Field of Classification Search
CPC .............. A61K 31/5377; A61K 31/422; A61K 31/428; A61K 31/427; A61K 31/4439
See application file for complete search history.

(56) References Cited

U.S. PATENT DOCUMENTS

| | | | |
|---|---|---|---|
| 2004/0254236 A1* | 12/2004 | Dong | C07D 249/14 514/426 |
| 2014/0288050 A1 | 9/2014 | Malcolm et al. | |
| 2014/0296274 A1* | 10/2014 | Toledano | A61K 31/485 514/282 |

FOREIGN PATENT DOCUMENTS

| | | |
|---|---|---|
| WO | WO 2006/125805 | * 11/2006 |
| WO | WO-2009/053449 A1 | 4/2009 |
| WO | WO-2012/015758 A2 | 2/2012 |
| WO | WO 2012/068209 | 5/2012 |
| WO | WO 2012/162468 | 11/2012 |
| WO | WO 2014/107344 | 7/2014 |
| WO | WO-2014/112955 A1 | 7/2014 |
| WO | WO 2015/046193 | 4/2015 |

OTHER PUBLICATIONS

Burford et al. (PNAS (2013); 110(26); 10830-10835).*
Gao et al "Flexible Modulation of Agonist Efficacy at the Human $A_3$ Adenosine Receptor by the Imidazoquinoline Allosteric Enhancer LUF6000" BMC Pharmacology vol. 8, pp. 1-11, 2008.

* cited by examiner

*Primary Examiner* — Shirley V Gembeh
(74) *Attorney, Agent, or Firm* — Cesari and McKenna, LLP

(57) ABSTRACT

Disclosed is an in vitro screening method for identifying an antagonist-to-agonist allosteric modifier of a mu-opioid receptor and an in vivo method for confirming that a test compound is such a modifier of a mu-opioid receptor. Also disclosed is a method for treating an opioid receptor-associated condition using a compound of Formula (I) and a pharmaceutical composition containing the same.

18 Claims, No Drawings

OPIOID RECEPTOR MODULATORS AND USE THEREOF

CROSS-REFERENCE TO RELATED APPLICATIONS

The present application claims the benefit of U.S. Provisional Patent Application No. 62/212,145, which was filed on Aug. 31, 2015, which is hereby incorporated by reference.

GOVERNMENT SUPPORT CLAUSE

This invention was made with government support under DA001583 awarded by the National Institutes of Health. The government has certain rights in the invention.

BACKGROUND

Opioids, e.g., morphine, act in both central and peripheral nervous systems to produce various pharmacological effects including, among others, analgesia and decreased gastrointestinal motility. Opioids have long been used as the most effective analgesics for treating acute pain, e.g., post-operative pain, and chronic pain, e.g., pain from cancer.

Opioids primarily activate three classic subtypes of opioid receptors, which are all G-protein-coupled receptors, namely, mu-opioid receptor (MOR), delta-opioid receptor (DOR), and kappa-opioid receptor (KOR). Currently, most opioids clinically used as analgesics are either nonselective or selective MOR agonists, producing undesired effects, such as respiratory depression. Furthermore, long-term use of these opioids for controlling chronic pain develops severe side effects such as tolerance, dependence, and addiction.

There is a need to develop new MOR modulators that have fewer side effects for the treatment of pain.

SUMMARY

The present invention relates to antagonist-to-agonist allosteric modifiers of a MOR for treating an opioid receptor-associated condition. Such a modifier combined with a MOR antagonist produces anti-nociceptive effects without developing severe side effects.

One aspect of this invention is an in vitro screening method for identifying an antagonist-to-agonist allosteric modifier of a MOR.

The in vitro screening method includes the following steps: (i) treating cells that express the MOR with both a test compound and a MOR antagonist, (ii) determining whether the MOR is activated, and (iii) identifying the test compounds as an antagonist-to-agonist allosteric modifier if the MOR is activated.

Examples of the cells used in this method include CHO-K1 cells. Preferably, the CHO-K1 cells express both opioid receptor mu-1 and G-protein α-subunit Gα15.

The MOR antagonist can be naloxone, naltrexone, or samidorphan.

Another aspect of this invention is an in vivo method for confirming that a test compound is an antagonist-to-agonist allosteric modifier of a MOR.

The in vivo method includes the following steps: (i) administering the test compound and a MOR antagonist to an animal, e.g., a B6 mouse or an ICR mouse; (ii) determining whether an analgesic effect is exerted on the animal; and (iii) confirming that the test compound is an antagonist-to-agonist allosteric modifier of the MOR upon observation of an analgesic effect. Again, the MOR antagonist can be naloxone, naltrexone, or samidorphan.

Still within the scope of this invention is a method for treating an opioid receptor-associated condition, e.g., pain, immune disease, esophageal reflux, diarrhea, anxiety, heroin addiction, and cough.

The method includes administering to a subject in need thereof an effective amount of a compound of Formula (I):

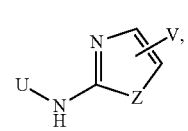

in which U is H, $C_{1-6}$ alkyl, $C_{3-8}$ cycloalkyl, $C_{2-8}$ heterocycloalkyl, $C_{6-14}$ aryl, or $C_{1-13}$ heteroaryl; V is H, $C_{1-6}$ alkyl, $C_{3-8}$ cycloalkyl, $C_{2-8}$ heterocycloalkyl, $C_{6-14}$ aryl, or $C_{1-13}$ heteroaryl; and Z is O or S.

Each of the $C_{1-6}$ alkyl, $C_{3-8}$ cycloalkyl, $C_{2-8}$ heterocycloalkyl, $C_{6-14}$ aryl, and $C_{1-13}$ heteroaryl, independently, is optionally mono-, di-, or tri-substituted with halo, OH, CN, $NH_2$, $NO_2$, COOH, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, —C(O)OR, —C(O)NRR', —NRC(O)R', —S(O)$_2$R, —S(O)$_2$NRR', —NRS(O)$_2$R', —C(O)R, or —NRS(O)$_2$NR'R''; or is optionally fused with $C_{3-8}$ cycloalkyl, $C_{2-8}$ heterocycloalkyl, $C_{6-14}$ aryl, or $C_{1-13}$ heteroaryl; each of R, R', and R'', independently, being H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, $C_{6-14}$ aryl, or $C_{1-13}$ heteroaryl.

In Formula (I), U can be:

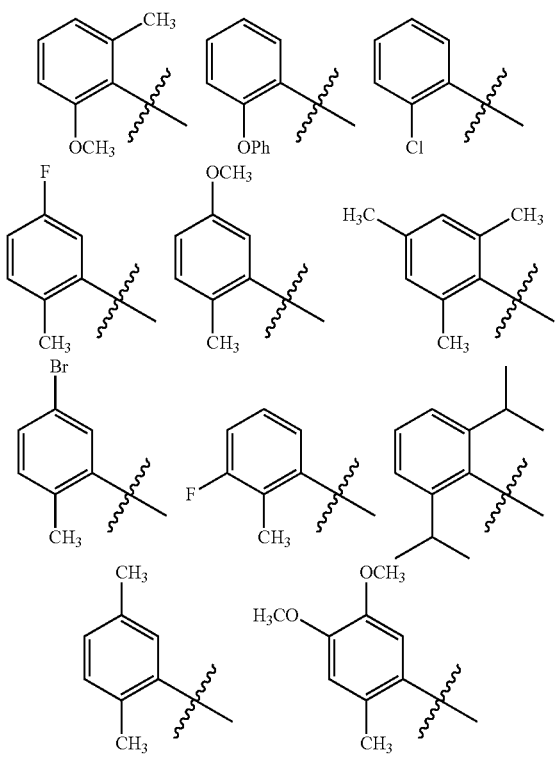

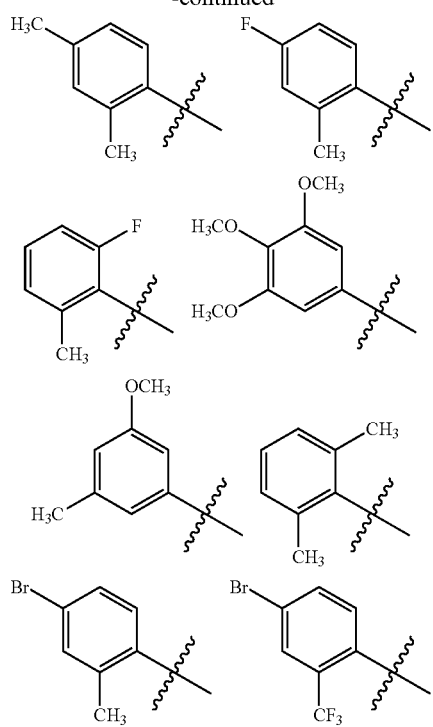
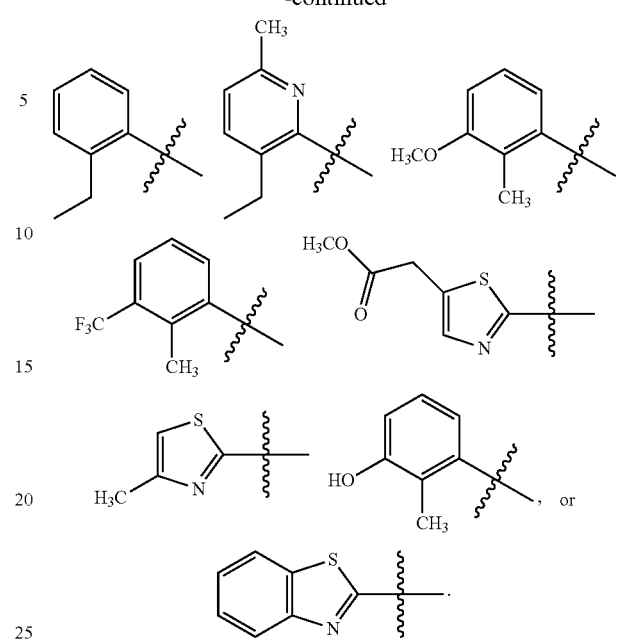
V can be:
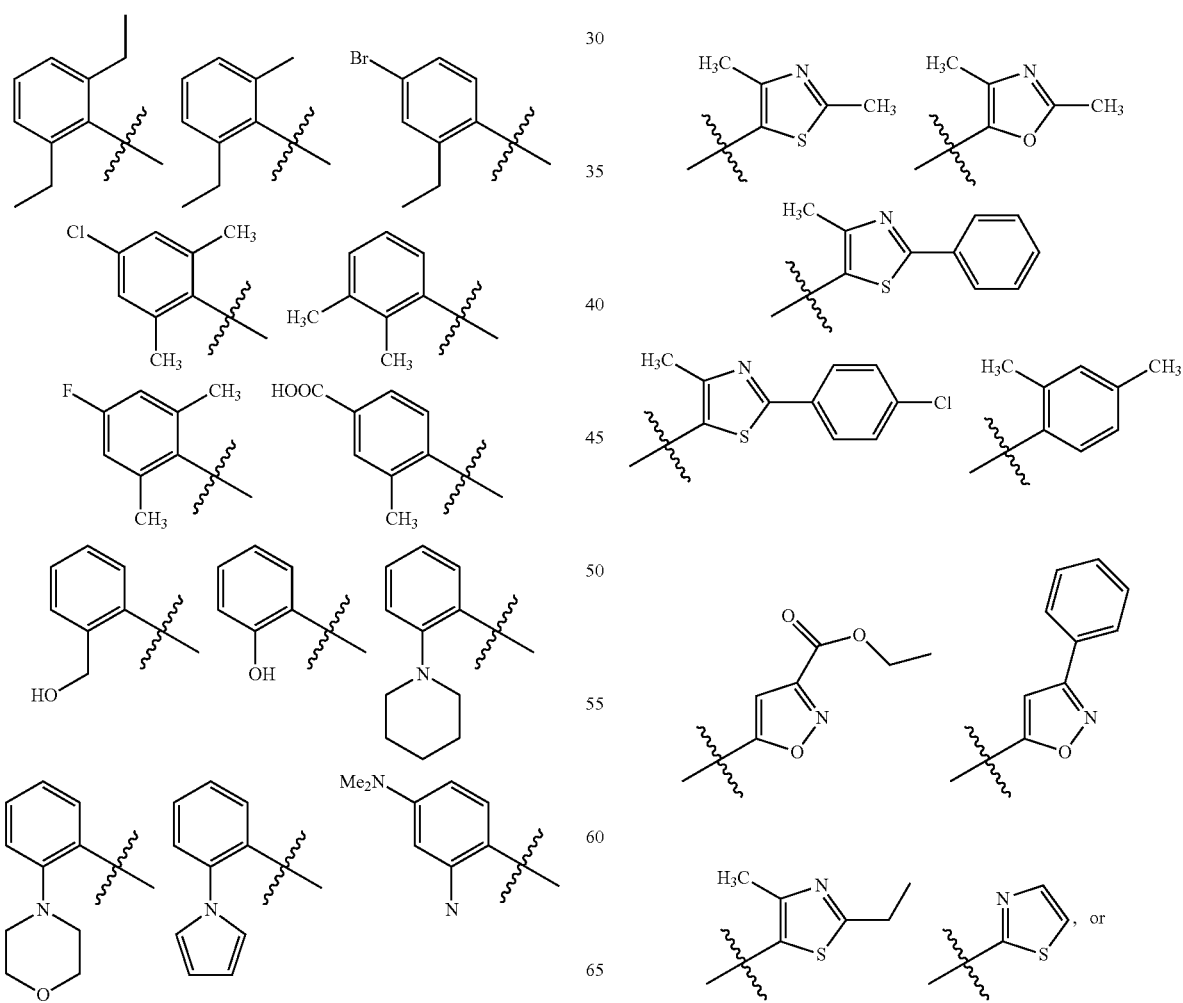

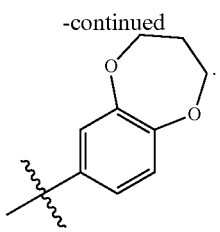

The term "alkyl" herein refers to a straight or branched hydrocarbon group, containing 1-20 (e.g., 1-10 and 1-6) carbon atoms. Examples include methyl, ethyl, n-propyl, i-propyl, n-butyl, i-butyl, and t-butyl. The term "haloalkyl" refers to alkyl substituted with one or more halogen (chloro, fluoro, bromo, or idodo) atoms. Examples include trifluoromethyl, bromomethyl, and 4,4,4-trifluorobutyl. The term "alkoxy" refers to an —O-alkyl group. Examples include methoxy, ethoxy, propoxy, and isopropoxy. The term "haloalkoxy" refers to alkoxy substituted with one or more halogen atoms. Examples include —O—$CH_2$Cl and —O—CHCl$CH_2$Cl.

The term "cycloalkyl" refers to a saturated and partially unsaturated monocyclic, bicyclic, tricyclic, or tetracyclic hydrocarbon group having 3 to 12 carbons. Examples include cyclopropyl, cyclobutyl, cyclopentyl, cyclopentenyl, cyclohexyl, cyclohexenyl, cycloheptyl, and cyclooctyl. The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "aryl" refers to a 6-carbon monocyclic, 10-carbon bicyclic, 14-carbon tricyclic aromatic ring system, in which each ring may have 1 to 5 substituents. Examples of aryl groups include phenyl, naphthyl, and anthracenyl. The term "aralkyl" refers to alkyl substituted with an aryl group. Examples include benzyl and naphthylmethyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl. The term "heteroaralkyl" refers to an alkyl group substituted with a heteroaryl group. Examples include pyridylmethyl and furylmethyl.

The term "halo" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl. The term "alkylamino" refers to alkyl-NH—. The term "dialkylamino" refers to alkyl-N(alkyl)-.

Alkyl, cycloalkyl, heterocycloalkyl, aralkyl, heteroaralkyl, haloalkyl, alkoxy, haloalkoxy, alkylamino, dialkylamino, aryl, and heteroaryl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cycloalkyl, and heterocycloalkyl, in which alkyl, alkenyl, alkynyl, alkyloxy, aryl, heteroaryl cycloalkyl, and heterocycloalkyl may further be substituted.

Herein, the term "compound" refers to the compounds of Formula (I) described above, as well as their salts and solvates, if applicable. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

The above-described method for treating an opioid receptor-associated condition, in addition to administration of a compound of Formula (I), can further include administration of a MOR antagonist, e.g., naloxone, naltrexone, and samidorphan. They can be administered jointly (i.e., in one pharmaceutical composition) or separately (i.e., in two pharmaceutical compositions; at the same time or at different times).

This method works via a unique mechanism, namely, opioid antagonist-mediated activation of a MOR to produce anti-nociceptive effects. Unlike using a MOR agonist, the method of this invention uses an allosteric modifier combined with a MOR antagonist to produce anti-nociceptive effects without developing severe side effects, e.g., tolerance, dependence, and addiction.

Also within the scope of the present invention is a pharmaceutical composition for treating an opioid receptor-associated condition.

The pharmaceutical composition contains a pharmaceutically acceptable carrier and one of the compounds of Formula (I) described above.

The pharmaceutical composition can further contain a MOR antagonist. Such a composition can be used for treating an opioid receptor-associated condition, e.g., pain, via the above-described mechanism, i.e., an opioid antagonist-mediated activation of a MOR.

This invention also covers use of such a composition for the manufacture of a medicament for treating an opioid receptor-associated condition.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The above-described compounds or a pharmaceutical composition containing such a compound can be administered to a subject orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

DETAILED DESCRIPTION

In an exemplary in vitro screening method of this invention for identifying antagonist-to-agonist allosteric modifiers of a MOR, cells that express a MOR are treated with a test compound and a MOR antagonist in a cellular calcium fluorescent assay and calcium fluorescence intensity is then measured to determine whether the MOR is activated. A test compound is identified as an antagonist-to-agonist allosteric modifier of the MOR if the MOR is activated.

Two parameters, i.e., $EC_{50}$ and the areas under the curves (AUC) of time-response curves obtained from a FLIPR® calcium assay, are typically used to measure the degree of MOR activation exerted by the test compound. $EC_{50}$ herein refers to the concentration of a compound that induces a response halfway between the baseline and the maximum after a specified exposure time. AUC refers to the area under the response curve, an indication of the compound's capability of activating a MOR when combined with a MOR antagonist.

In an exemplary in vivo method of this invention for confirming that a test compound is an antagonist-to-agonist allosteric modifier of a MOR, a test compound and a MOR antagonist are injected into a pain model mouse (for example, intravenous but not limited), basal latencies are recorded before the treatment and test latencies are recorded at various specified times after the injection, and a time-response curve is recorded and AUC values are calculated to determine whether an analgesic effect is exerted on the mouse. The test compound is confirmed to be an antagonist-to-agonist allosteric modifier of the MOR upon observation of an analgesic effect.

Within this invention is a pharmaceutical composition for treating an opioid receptor-associated condition, e.g., pain, the composition containing a pharmaceutically acceptable carrier and one of the compounds of Formula (I) set forth above. Examples of the pain include renal colic, acute pancreatitis, angina, chronic neuropathic pain, chronic regional complex pain syndrome, and cancer pain.

Also covered by this invention is a method for treating an opioid receptor-associated condition, e.g., pain, the method including administering to a subject in need thereof an effective amount of a compound of Formula (I).

Methods for synthesizing the compounds of Formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); and G. J. Yu et al., J. Med. Chem. 2008, 51, 6044-6054.

The compounds of Formula (I) thus prepared can be initially screened using in vitro assays, e.g., the FLIPR® calcium assay described in Example 72 below, for their potency in activating a MOR in cells. They can be subsequently evaluated using in vivo assays, e.g., a tail-flick test assay, for their efficacy in modulating the conformation of intercellular opioid receptor in a mammal. The selected compounds can be further tested to verify their efficacy in treating an opioid receptor-associated condition. For example, a compound can be administered to an animal (e.g., a mouse) having an opioid receptor-associated condition and its therapeutic effects are then assessed. Based on the results, an appropriate dosage range and administration route can be determined.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Shown in the table below are the structures and names of 71 exemplary compounds of Formula (I). The methods for preparing these compounds, as well as the analytical data for the compounds thus prepared, are set forth in Examples 1-71 below. The procedures for testing these compounds are described in Examples 72 and 73 also below.

All 71 compounds, when combined with a MOR antagonist, were found to activate a MOR to various degrees as indicated by their $EC_{50}$ and AUC values included in the following table. $EC_{50}$ values are presented in three ranges, i.e., A: 1 µM-3 µM, B: 3 µM-10 µM, and C: >10 µM. AUC values are presented in two ranges, i.e., +: >5000 and −: <5000.

| Number | Chemical structure | Compound name | EC$_{50}$ | AUC |
|---|---|---|---|---|
| 1 | 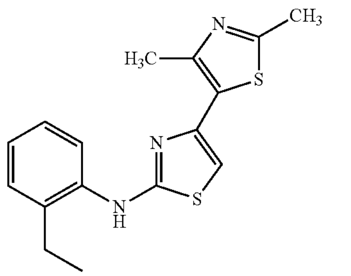 [SMILES: CCc1ccccc1Nc1nc(-c2sc(C)nc2C)cs1] | N-(2-Ethylphenyl)-2',4'-dimethyl-4,5'-bi-1,3-thiazol-2-amine | B | + |
| 4 | 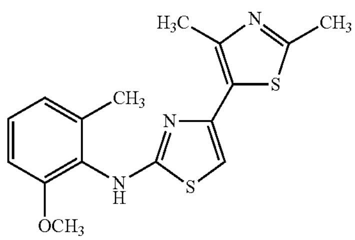 [SMILES: COc1cccc(C)c1Nc1nc(-c2sc(C)nc2C)cs1] | N-(2-Methoxy-6-methylphenyl)-2',4'-dimethyl-4,5'-bi-1,3-thiazol-2-amine | C | + |
| 6 | 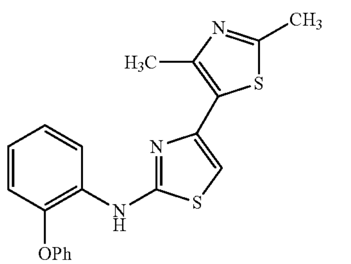 [SMILES: Cc1nc(C)c(-c2csc(Nc3ccccc3Oc3ccccc3)n2)s1] | N-(2-Phenoxyphenyl)-2',4'-dimethyl-4,5'-bi-1,3-thiazol-2-amine | C | − |
| 8 | 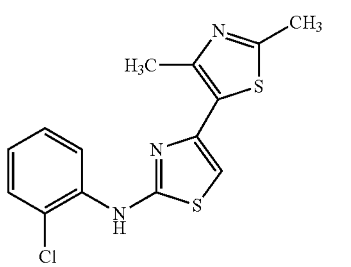 [SMILES: Cc1nc(C)c(-c2csc(Nc3ccccc3Cl)n2)s1] | N-(2-Chlorophenyl)-2',4'-dimethyl-4,5'-bi-1,3-thiazol-2-amine | C | − |
| 9 | 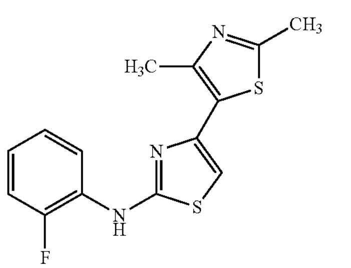 [SMILES: Cc1nc(C)c(-c2csc(Nc3ccccc3F)n2)s1] | N-(2-Fluorophenyl)-2',4'-dimethyl-4,5'-bi-1,3-thiazol-2-amine | C | − |
| 10 | 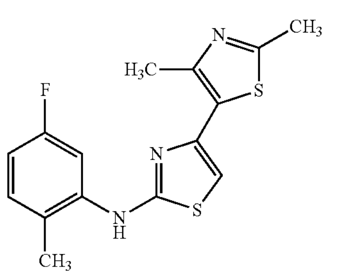 [SMILES: Cc1nc(C)c(-c2csc(Nc3cc(F)ccc3C)n2)s1] | N-(5-Fluoro-2-methylphenyl)-2',4'-dimethyl-4,5'-bi-1,3-thiazol-2-amine | C | − |

-continued

| Number | Chemical structure | Compound name | EC$_{50}$ | AUC |
|---|---|---|---|---|
| 12 | 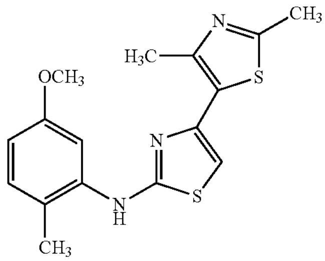 [SMILES: COc1ccc(C)c(Nc2nc(-c3sc(C)nc3C)cs2)c1] | N-(5-Methoxy-2-methylphenyl)-2',4'-dimethyl-4,5'-bi-1,3-thiazol-2-amine | C | − |
| 14 | 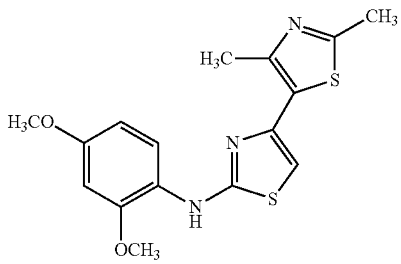 [SMILES: COc1ccc(Nc2nc(-c3sc(C)nc3C)cs2)c(OC)c1] | N-(2,4-Dimethoxyphenyl)-2',4'-dimethyl-4,5'-bi-1,3-thiazol-2-amine | C | + |
| 15 | 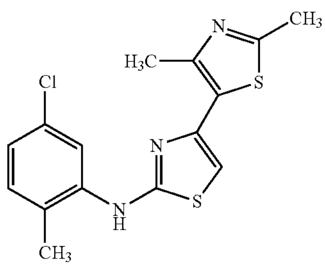 | N-(5-Chloro-2-methylphenyl)-2',4'-dimethyl-4,5'-bi-1,3-thiazol-2-amine | C | − |
| 17 | 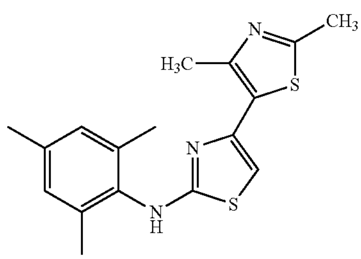 | 2',4'-Dimethyl-N-(2,4,6-trimethylphenyl)-4,5'-bi-1,3-thiazol-2-amine | B | + |
| 19 | 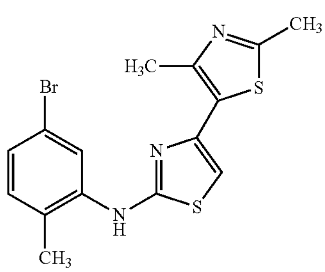 [SMILES: Cc1nc(C)c(-c2csc(Nc3cc(Br)ccc3C)n2)s1] | N-(5-Bromo-2-methylphenyl)-2',4'-dimethyl-4,5'-bi-1,3-thiazol-2-amine | C | − |
| 21 | 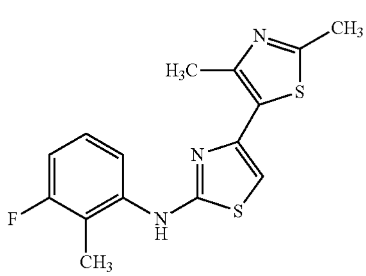 [SMILES: Cc1nc(C)c(-c2csc(Nc3cccc(F)c3C)n2)s1] | N-(3-Fluoro-2-methylphenyl)-2',4'-dimethyl-4,5'-bi-1,3-thiazol-2-amine | C | + |

| Number | Chemical structure | Compound name | EC$_{50}$ | AUC |
|---|---|---|---|---|
| 23 | 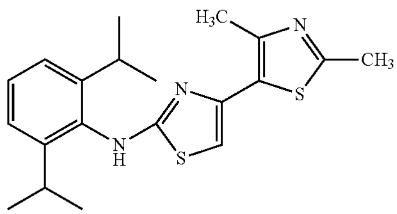 [SMILES: Cc1nc(C)c(-c2csc(Nc3c(C(C)C)cccc3C(C)C)n2)s1] | N-(2,6-Diisopropylphenyl)-2',4'-dimethyl-4,5'-bi-1,3-thiazol-2-amine | C | − |
| 25 | 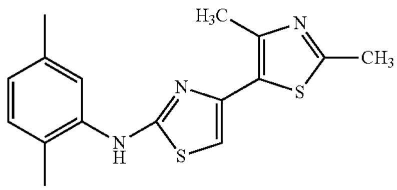 [SMILES: Cc1ccc(C)c(Nc2nc(-c3sc(C)nc3C)cs2)c1] | N-(2,5-Dimethylphenyl)-2',4'-dimethyl-4,5'-bi-1,3-thiazol-2-amine | C | − |
| 27 | 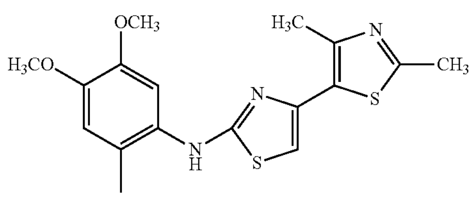 [SMILES: COc1cc(C)c(Nc2nc(-c3sc(C)nc3C)cs2)cc1OC] | N-(4,5-Dimethoxy-2-methylphenyl)-2',4'-dimethyl-4,5'-bi-1,3-thiazol-2-amine | C | − |
| 29 | 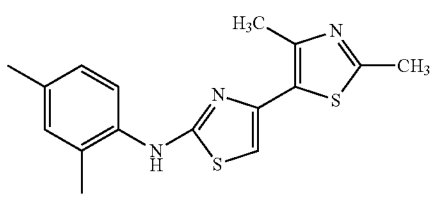 | N-(2,4-Dimethylphenyl)-2',4'-dimethyl-4,5'-bi-1,3-thiazol-2-amine | B | + |
| 31 | 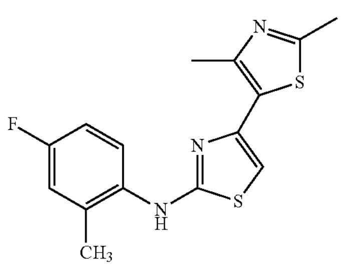 [SMILES: Cc1nc(C)c(-c2csc(Nc3ccc(F)cc3C)n2)s1] | N-(4-Fluoro-2-methylphenyl)-2',4'-dimethyl-4,5'-bi-1,3-thiazol-2-amine | C | − |
| 33 | 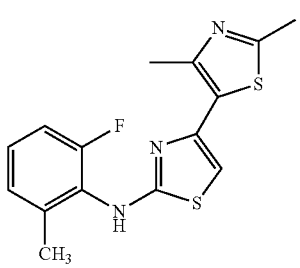 [SMILES: Cc1nc(C)c(-c2csc(Nc3c(C)cccc3F)n2)s1] | N-(2-Fluoro-6-methylphenyl)-2',4'-dimethyl-4,5'-bi-1,3-thiazol-2-amine | B | + |

-continued

| Number | Chemical structure | Compound name | EC$_{50}$ | AUC |
|---|---|---|---|---|
| 35 | 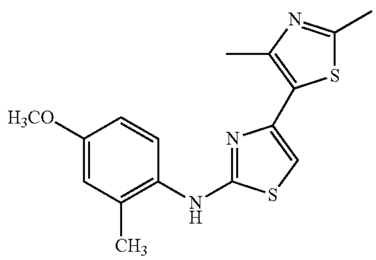 [SMILES: COc1ccc(Nc2nc(-c3sc(C)nc3C)cs2)c(C)c1] | N-(4-Methoxy-2-methylphenyl)-2',4'-dimethyl-4,5'-bi-1,3-thiazol-2-amine | C | + |
| 37 | 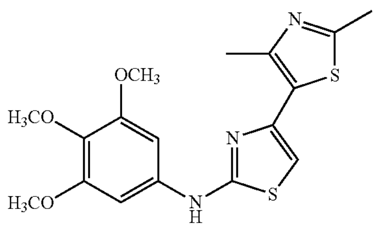 [SMILES: COc1cc(Nc2nc(-c3sc(C)nc3C)cs2)cc(OC)c1OC] | 2',4'-Dimethyl-N-(3,4,5-trimethoxyphenyl)-4,5'-bi-1,3-thiazol-2-amine | C | − |
| 39 | 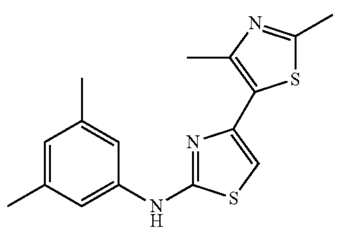 | N-(3,5-Dimethylphenyl)-2',4'-dimethyl-4,5'-bi-1,3-thiazol-2-amine | C | − |
| 41 | 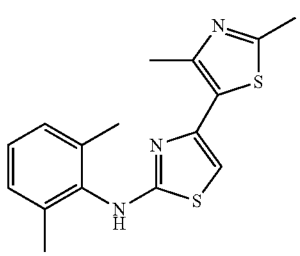 [SMILES: Cc1nc(C)c(-c2csc(Nc3c(C)cccc3C)n2)s1] | N-(2,6-Dimethylphenyl)-2',4'-dimethyl-4,5'-bi-1,3-thiazol-2-amine | C | − |
| 42 | 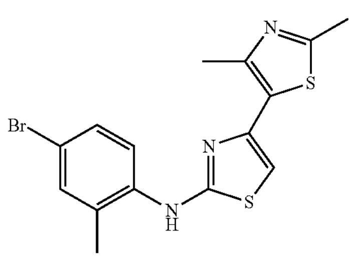 [SMILES: Cc1nc(C)c(-c2csc(Nc3ccc(Br)cc3C)n2)s1] | N-(4-Bromo-2-methylphenyl)-2',4'-dimethyl-4,5'-bi-1,3-thiazol-2-amine | C | − |
| 43 | 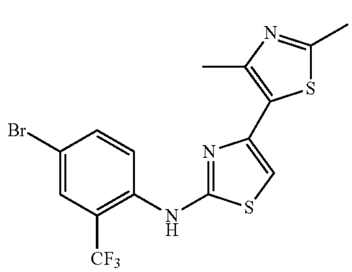 [SMILES: Cc1nc(C)c(-c2csc(Nc3ccc(Br)cc3C(F)(F)F)n2)s1] | N-[4-Bromo-2-(trifluoromethyl)phenyl]-2',4'-dimethyl-4,5'-bi-1,3-thiazol-2-amine | C | + |

-continued

| Number | Chemical structure | Compound name | EC$_{50}$ | AUC |
|---|---|---|---|---|
| 44 | 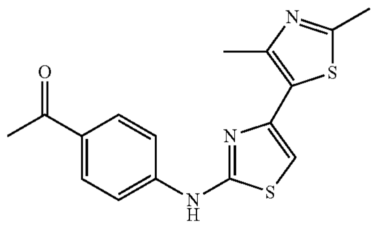 [SMILES: CC(=O)c1ccc(Nc2nc(-c3sc(C)nc3C)cs2)cc1] | 1-{4-[(2',4'-Dimethyl-4,5'-bi-1,3-thiazol-2-yl)amino]phenyl}ethanone | C | − |
| 45 | 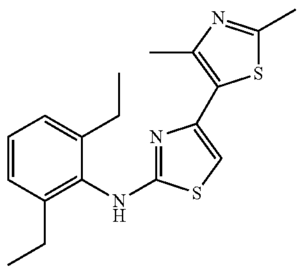 [SMILES: CCc1cccc(CC)c1Nc1nc(-c2sc(C)nc2C)cs1] | N-(2,6-Diethylphenyl)-2',4'-dimethyl-4,5'-bi-1,3-thiazol-2-amine | A | − |
| 47 | 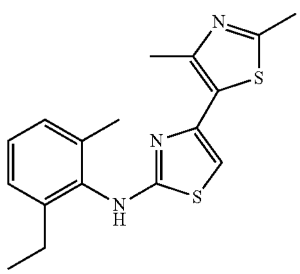 [SMILES: CCc1cccc(C)c1Nc1nc(-c2sc(C)nc2C)cs1] | N-(2-Ethyl-6-methylphenyl)-2',4'-dimethyl-4,5'-bi-1,3-thiazol-2-amine | A | + |
| 49 | 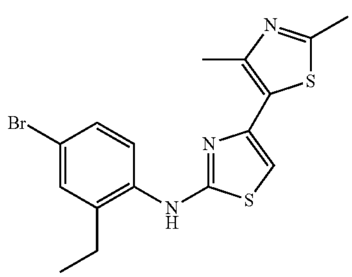 [SMILES: CCc1cc(Br)ccc1Nc1nc(-c2sc(C)nc2C)cs1] | N-(4-Bromo-2-ethylphenyl)-2',4'-dimethyl-4,5'-bi-1,3-thiazol-2-amine | B | − |
| 51 | 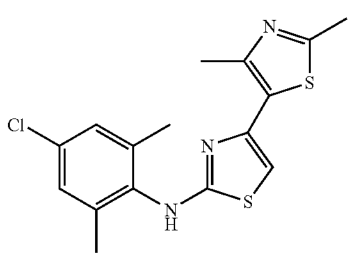 [SMILES: Cc1nc(C)c(-c2csc(Nc3c(C)cc(Cl)cc3C)n2)s1] | N-(4-Chloro-2,6-dimethylphenyl)-2',4'-dimethyl-4,5'-bi-1,3-thiazol-2-amine | C | − |
| 53 | 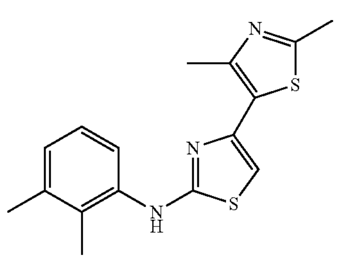 | N-(2,3-Dimethylphenyl)-2',4'-dimethyl-4,5'-bi-1,3-thiazol-2-amine | C | + |

| Number | Chemical structure | Compound name | EC$_{50}$ | AUC |
|---|---|---|---|---|
| 55 | 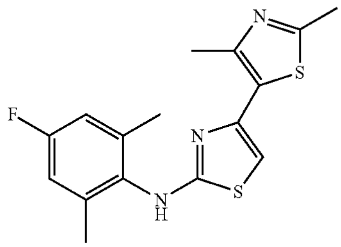 [SMILES: Cc1nc(C)c(-c2csc(Nc3c(C)cc(F)cc3C)n2)s1] | N-(4-Fluoro-2,6-dimethylphenyl)-2',4'-dimethyl-4,5'-bi-1,3-thiazol-2-amine | C | + |
| 57 | 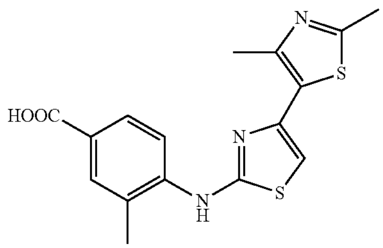 [SMILES: Cc1nc(C)c(-c2csc(Nc3ccc(C(=O)O)cc3C)n2)s1] | 4-[(2',4'-Dimethyl-4,5'-bi-1,3-thiazol-2-yl)amino]-3-methylbenzoic acid | C | − |
| 60 | 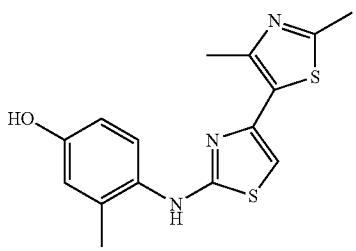 [SMILES: Cc1nc(C)c(-c2csc(Nc3ccc(O)cc3C)n2)s1] | 4-[(2',4'-Dimethyl-4,5'-bi-1,3-thiazol-2-yl)amino]-3-methylphenol | C | − |
| 62 | 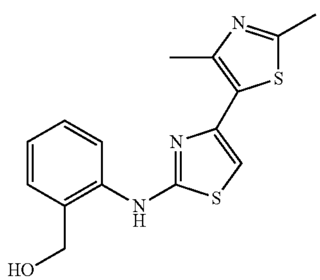 [SMILES: Cc1nc(C)c(-c2csc(Nc3ccccc3CO)n2)s1] | {2-[(2',4'-Dimethyl-4,5'-bi-1,3-thiazol-2-yl)amino]phenyl}methanol | C | − |
| 65 | 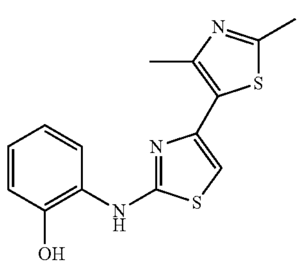 [SMILES: Cc1nc(C)c(-c2csc(Nc3ccccc3O)n2)s1] | 2-[(2',4'-Dimethyl-4,5'-bi-1,3-thiazol-2-yl)amino]phenol | C | + |
| 68 | 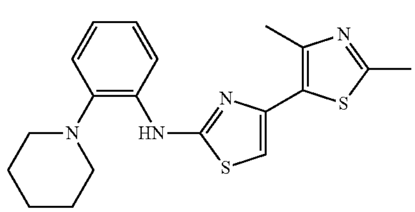 [SMILES: Cc1nc(C)c(-c2csc(Nc3ccccc3N3CCCCC3)n2)s1] | 2',4'-Dimethyl-N-[2-(1-piperidinyl)phenyl]-4,5'-bi-1,3-thiazol-2-amine | C | − |

-continued

| Number | Chemical structure | Compound name | EC$_{50}$ | AUC |
|---|---|---|---|---|
| 70 | 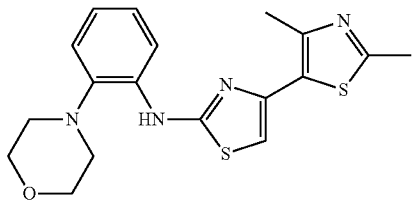 [SMILES: Cc1nc(C)c(-c2csc(Nc3ccccc3N3CCOCC3)n2)s1] | 2',4'-Dimethyl-N-[2-(4-morpholinyl)phenyl]-4,5'-bi-1,3-thiazol-2-amine | B | – |
| 72 | 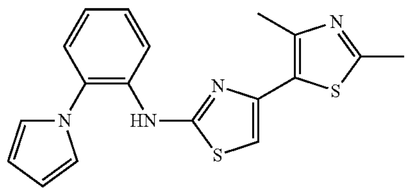 [SMILES: Cc1nc(C)c(-c2csc(Nc3ccccc3-n3cccc3)n2)s1] | 2',4'-Dimethyl-N-[2-(1H-pyrrol-1-yl)phenyl]-4,5'-bi-1,3-thiazol-2-amine | C | – |
| 75 | 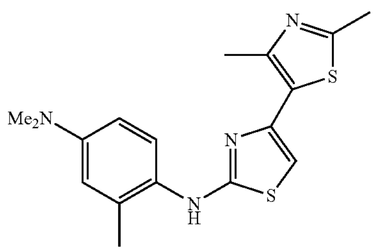 [SMILES: Cc1nc(C)c(-c2csc(Nc3ccc(N(C)C)cc3C)n2)s1] | N$^1$-(2',4'-Dimethyl-4,5'-bi-1,3-thiazol-2-yl)-N$^4$,N$^4$,2-trimethyl-1,4-benzenediamine | C | – |
| 77 | 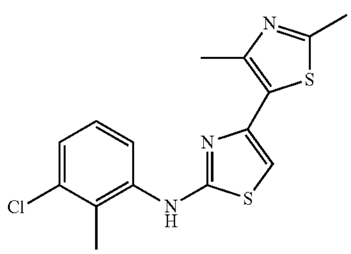 [SMILES: Cc1nc(C)c(-c2csc(Nc3cccc(Cl)c3C)n2)s1] | N-(3-Chloro-2-methylphenyl)-2',4'-dimethyl-4,5'-bi-1,3-thiazol-2-amine | C | – |
| 79 | 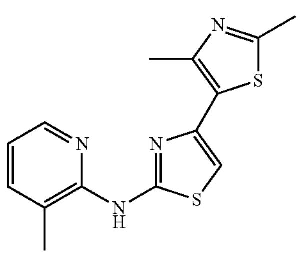 [SMILES: Cc1nc(C)c(-c2csc(Nc3ncccc3C)n2)s1] | 2',4'-Dimethyl-N-(3-methyl-2-pyridinyl)-4,5'-bi-1,3-thiazol-2-amine | C | – |
| 82 | 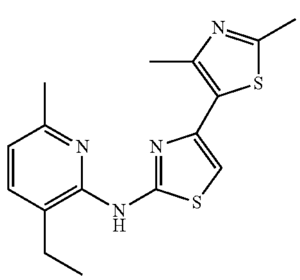 [SMILES: CCc1ccc(C)nc1Nc1nc(-c2sc(C)nc2C)cs1] | N-(3-Ethyl-6-methyl-2-pyridinyl)-2',4'-dimethyl-4,5'-bi-1,3-thiazol-2-amine | C | – |

-continued

| Number | Chemical structure | Compound name | EC$_{50}$ | AUC |
|---|---|---|---|---|
| 85 | 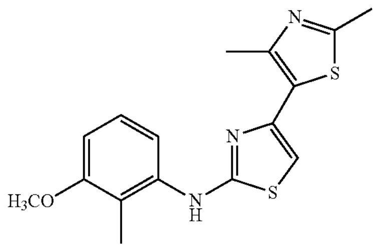 [SMILES: COc1cccc(Nc2nc(-c3sc(C)nc3C)cs2)c1C] | N-(3-Methoxy-2-methylphenyl)-2',4'-dimethyl-4,5'-bi-1,3-thiazol-2-amine | B | + |
| 87 | 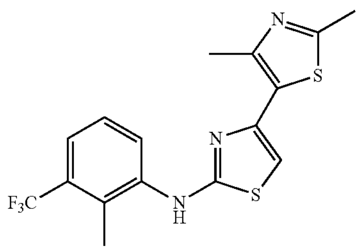 [SMILES: Cc1nc(C)c(-c2csc(Nc3cccc(O)c3C)n2)s1] | 2',4'-Dimethyl-N-[2-methyl-3-(trifluoromethyl)phenyl]-4,5'-bi-1,3-thiazol-2-amine | C | − |
| 89 | 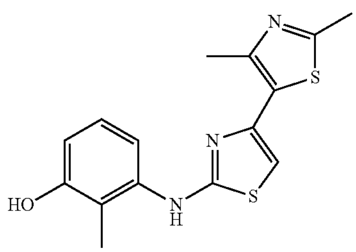 | 3-[(2',4'-Dimethyl-4,5'-bi-1,3-thiazol-2-yl)amino]-2-methylphenol | C | − |
| 92 | 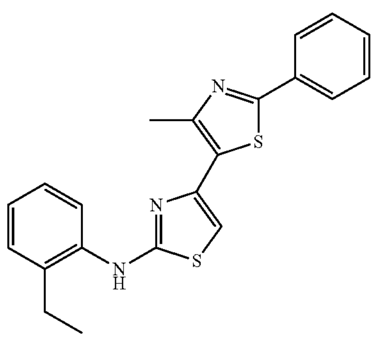 [SMILES: CCc1ccccc1Nc1nc(-c2sc(-c3ccccc3)nc2C)cs1] | N-(2-Ethylphenyl)-4'-methyl-2'-phenyl-4,5'-bi-1,3-thiazol-2-amine | C | − |
| 93 | 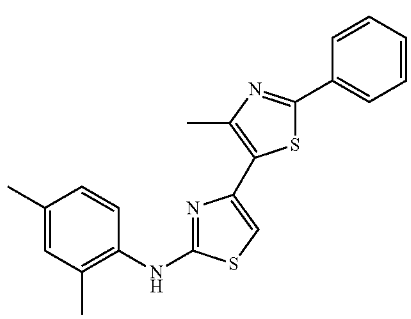 [SMILES: Cc1ccc(Nc2nc(-c3sc(-c4ccccc4)nc3C)cs2)c(C)c1] | N-(2,4-Dimethylphenyl)-4'-methyl-2'-phenyl-4,5'-bi-1,3-thiazol-2-amine | C | − |

-continued

| Number | Chemical structure | Compound name | EC$_{50}$ | AUC |
|---|---|---|---|---|
| 94 | 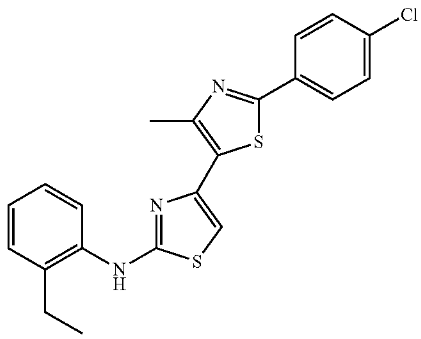 [SMILES: CCc1ccccc1Nc1nc(-c2sc(-c3ccc(Cl)cc3)nc2C)cs1] | 2'-(4-Chlorophenyl)-N-(2-ethylphenyl)-4'-methyl-4,5'-bi-1,3-thiazol-2-amine | C | − |
| 95 | 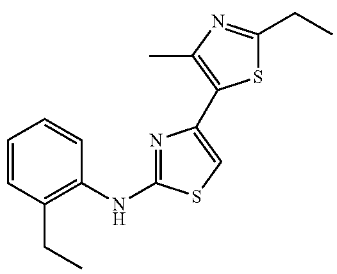 [SMILES: CCc1nc(C)c(-c2csc(Nc3ccccc3CC)n2)s1] | 2'-Ethyl-N-(2-ethylphenyl)-4'-methyl-4,5'-bi-1,3-thiazol-2-amine | B | + |
| 98 | 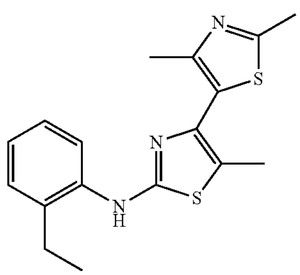 [SMILES: CCc1ccccc1Nc1nc(-c2sc(C)nc2C)c(C)s1] | N-(2-Ethylphenyl)-2',4',5-trimethyl-4,5'-bi-1,3-thiazol-2-amine | C | − |
| 100 | 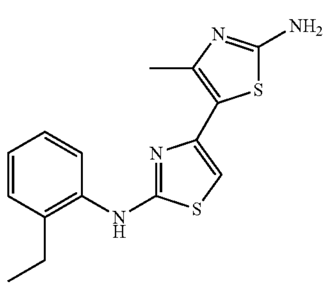 [SMILES: CCc1ccccc1Nc1nc(-c2sc(N)nc2C)cs1] | N$^2$-(2-ethylphenyl)-4'-methyl-4,5'-bi-1,3-thiazole-2,2'-diamine | C | − |
| 102 | 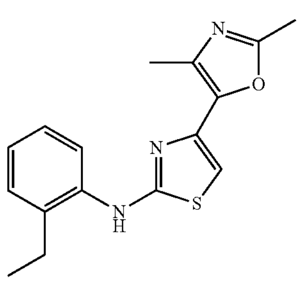 [SMILES: CCc1ccccc1Nc1nc(-c2oc(C)nc2C)cs1] | 4-(2,4-Dimethyl-1,3-oxazol-5-yl)-N-(2-ethylphenyl)-1,3-thiazol-2-amine | B | + |

-continued

| Number | Chemical structure | Compound name | EC$_{50}$ | AUC |
|---|---|---|---|---|
| 105 | 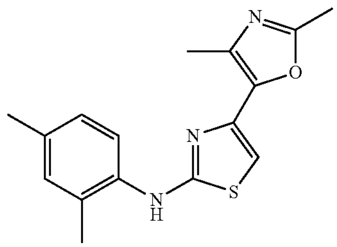 | 4-(2,4-Dimethyl-1,3-oxazol-5-yl)-N-(2,4-dimethylphenyl)-1,3-thiazol-2-amine | C | + |
| 106 | 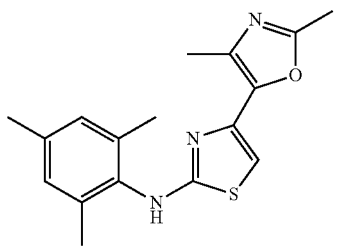 | 4-(2,4-Dimethyl-1,3-oxazol-5-yl)-N-(2,4,6-trimethylphenyl)-1,3-thiazol-2-amine | B | + |
| 107 | 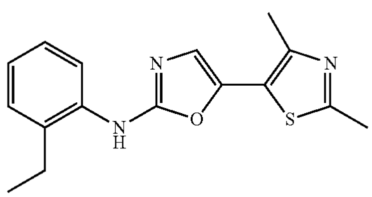 | 5-(2,4-Dimethyl-1,3-thiazol-5-yl)-N-(2-ethylphenyl)-1,3-oxazol-2-amine | C | + |
| 109 | 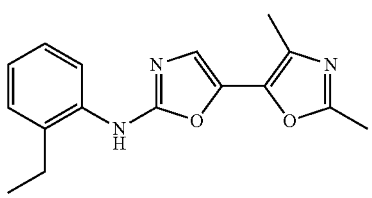 [SMILES: CCc1ccccc1Nc1ncc(-c2oc(C)nc2C)o1] | 5-(2,4-Dimethyl-1,3-oxazol-5-yl)-N-(2-ethylphenyl)-1,3-oxazol-2-amine | C | − |
| 111 | 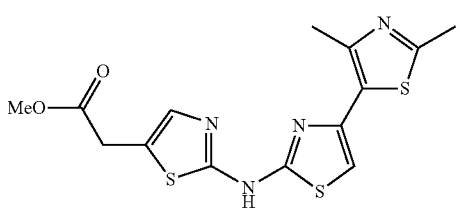 [SMILES: COC(=O)Cc1cnc(Nc2nc(-c3sc(C)nc3C)cs2)s1] | Methyl {2-[(2',4'-dimethyl-4,5'-bi-1,3-thiazol-2-yl)amino]-1,3-thiazol-5-yl}acetate | C | − |
| 114 | 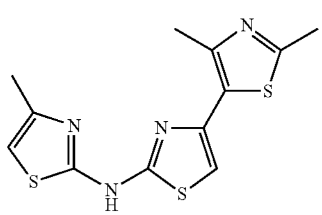 [SMILES: Cc1csc(Nc2nc(-c3sc(C)nc3C)cs2)n1] | 2',4'-Dimethyl-N-(4-methyl-1,3-thiazol-2-yl)-4,5'-bi-1,3-thiazol-2-amine | C | − |
| 117 | 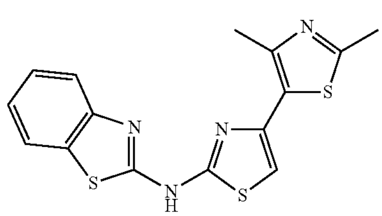 [SMILES: Cc1nc(C)c(-c2csc(Nc3nc4ccccc4s3)n2)s1] | N-(1,3-Benzothiazol-2-yl)-2',4'-dimethyl-4,5'-bi-1,3-thiazol-2-amine | C | − |

| Number | Chemical structure | Compound name | EC$_{50}$ | AUC |
|---|---|---|---|---|
| 120 | 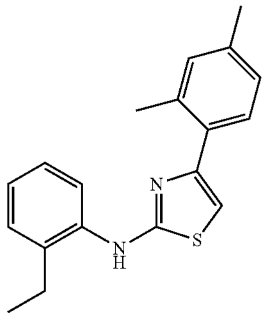 [SMILES: CCc1ccccc1Nc1nc(-c2ccc(C)cc2C)cs1] | 4-(2,4-Dimethylphenyl)-N-(2-ethylphenyl)-1,3-thiazol-2-amine | C | – |
| 121 | 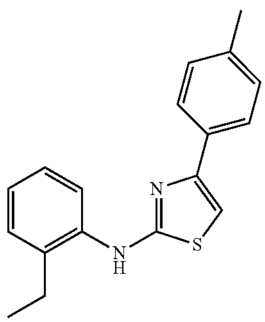 [SMILES: CCc1ccccc1Nc1nc(-c2ccc(C)cc2)cs1] | N-(2-Ethylphenyl)-4-(4-methylphenyl)-1,3-thiazol-2-amine | C | – |
| 122 | 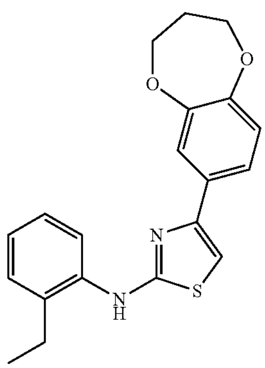 [SMILES: CCc1ccccc1Nc1nc(-c2ccc3c(c2)OCCCO3)cs1] | 4-(3,4-Dihydro-2H-1,5-benzodioxepin-7-yl)-N-(2-ethylphenyl)-1,3-thiazol-2-amine | C | – |
| 123 | 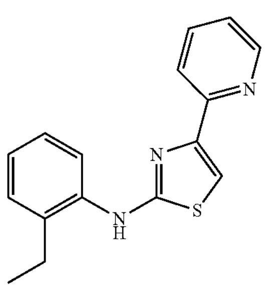 [SMILES: CCc1ccccc1Nc1nc(-c2ccccn2)cs1] | N-(2-Ethylphenyl)-4-(2-pyridinyl)-1,3-thiazol-2-amine | C | – |
| 124 | 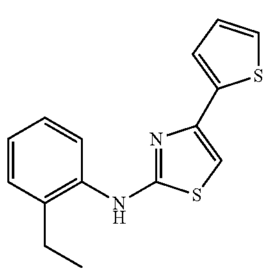 [SMILES: CCc1ccccc1Nc1nc(-c2cccs2)cs1] | N-(2-Ethylphenyl)-4-(2-thiophenyl)-1,3-thiazol-2-amine | C | – |

-continued

| Number | Chemical structure | Compound name | EC$_{50}$ | AUC |
|---|---|---|---|---|
| 126 | 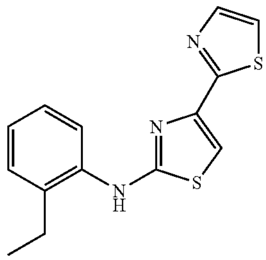 [SMILES: CCc1ccccc1Nc1nc(-c2nccs2)cs1] | N-(2-Ethylphenyl)-2,4'-bi-1,3-thiazol-2'-amine | C | – |
| 127 | 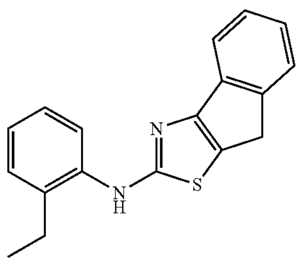 [SMILES: CCc1ccccc1Nc1nc2c(s1)Cc1ccccc1-2] | N-(2-Ethylphenyl)-8H-indeno[1,2-d][1,3]thiazol-2-amine | C | – |
| 128 | 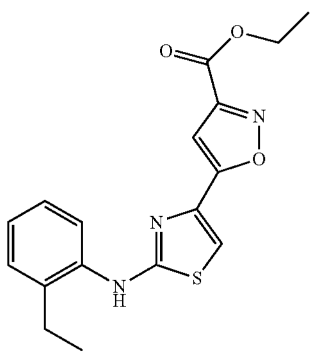 [SMILES: CCOC(=O)c1cc(-c2csc(Nc3ccccc3CC)n2)on1] | Ethyl 5-{2-[(2-ethylphenyl)amino]-1,3-thiazol-4-yl}-1,2-oxazole-3-carboxylate | C | – |
| 129 | 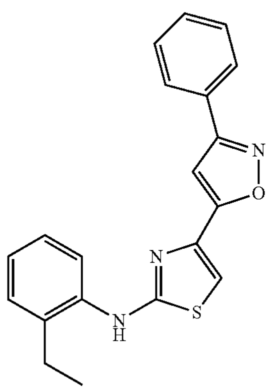 [SMILES: CCc1ccccc1Nc1nc(-c2cc(-c3ccccc3)no2)cs1] | N-(2-Ethylphenyl)-4-(3-phenyl-1,2-oxazol-5-yl)-1,3-thiazol-2-amine | C | – |
| 130 | 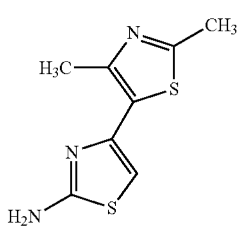 | 2',4'-Dimethyl-4,5'-bi-1,3-thiazol-2-amine | C | – |

| Number | Chemical structure | Compound name | EC$_{50}$ | AUC |
|---|---|---|---|---|
| 131 | 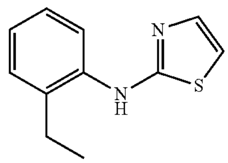 | N-(2-Ethylphenyl)-1,3-thiazol-2-amine | C | – |
| 132 | 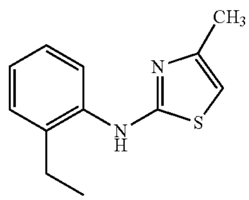 | N-(2-Ethylphenyl)-4-methyl-1,3-thiazol-2-amine | C | – |

Described below are three procedures used to synthesize intermediates of the above-described 71 compounds.

Procedure A for Preparation of N-phenylthioureas

To a solution of aniline in 1.0 N HCl$_{(aq)}$ was added ammonium thiocyanate at 100° C. The resulting mixture was stirred at 100° C. for 16 h to 24 h and then cooled to room temperature to afford a solution. The solution was diluted with cold water and neutralized with 28% ammonium hydroxide solution (pH>7) to form precipitate. The precipitate thus formed was collected by vacuum filtration and washed with water and n-hexane/diethyl ether to give the desired product. In some examples, the collected precipitate was purified by column chromatography or recrystallization to provide a pure product.

Procedure B for Preparation of Bithazole Derivatives

To a solution of 2-bromo-1-(2,4-dimethyl-thiazol-5-yl)ethanone in ethanol was added N-phenyl-thiourea. The resulting solution was stirred at room temperature for 30 minutes to overnight, followed by removal of ethanol under reduced pressure. The residue thus obtained was treated with saturated NaHCO$_{3(aq)}$ solution and extracted with CH$_2$Cl$_2$. Organic layers were combined, washed with brine, dried over MgSO$_{4(s)}$, filtered, and concentrated to afford a residue. The residue was purified by Isco Combi-Flash Companion column chromatography to give the desired product.

Procedure C for Preparation of an Intermediate for Syntheses of Carbamothioylbenzamides A solution of aniline and benzyl isothiocyanate in acetone was stirred at 60° C. for 30 to 40 minutes. The solution was poured into cold water to form precipitate. The precipitate was collected by vacuum filtration and washed with water to give the desired product which was directly used in the next step without further purification.

All chemicals and solvents were purchased from commercial suppliers and used as received. All reactions were carried out under an atmosphere of dry nitrogen. Reactions were monitored by TLC using Merck 60 F254 silica gel glass backed plates (5×10 cm); and zones were detected visually under ultraviolet irradiation (254 nm) or by spraying with phosphomolybdic acid reagent (Aldrich) followed by heating at 80° C. All flash column chromatography was performed with Merck Kieselgel 60, No. 9385, 230-400 mesh ASTM silica gel as the stationary phase. Proton ($^1$H) nuclear magnetic resonance spectra were measured on a Varian Mercury-300 or Varian Mercury-400 spectrometer. Chemical shifts were recorded in parts per million (ppm) on the delta (δ) scale relative to the resonance of the solvent peak. The following abbreviations were used to describe coupling: s=singlet; d=doublet; t=triplet; q=quartet; quin=quintet; br=broad; and m=multiplet. LCMS data were measured on an Agilent MSD-1100 ESI-MS/MS, Agilent 1200 series LC/MSD VL, and Waters Acquity UPLC-ESI-MS/MS system.

EXAMPLE 1

N-(2-Ethylphenyl)-2',4'-dimethyl-4,5'-bi-1,3-thiazol-2-amine

Compound 1

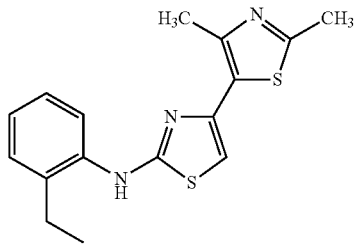

Step 1. 1-(2-Ethylphenyl)thiourea

Compound 2

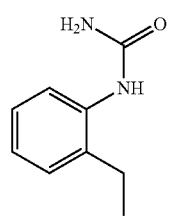

Following the procedure A, 2-ethylaniline (1.00 mL, 8.10 mmol), 1.0 N HCl$_{(aq)}$ (8.0 mL), and ammonium thiocyanate (0.620 g, 8.15 mmol) were used to carry out the reaction. After the resulting mixture was stirred for 20 hours and work-up, the crude product thus obtained was purified by Isco Combi-Flash Companion column chromatography (10-60% EtOAc in n-hexane) to give 1-(2-ethylphenyl)thiourea (0.600 g, 41%) as a white solid.

$^1$H NMR (CDCl$_3$, 400 MHz) δ 7.69 (br, 1H), 7.35-7.22 (m, 4H), 2.67 (q, 2H), 1.22 (t, 3H).

Step 2. 2-Bromo-1-(2,4-dimethyl-thiazol-5-yl)ethanone

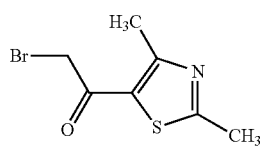

Compound 3

To a solution of 5-acetyl-2,4-dimethylthiazole (2.59 g, 16.7 mmol) in 33% of HBr in acetic acid (18 mL) was added phenyltrimethylammonium tribromide (6.59 g, 17.5 mmol) at room temperature. After the solution was stirred for overnight, it was poured into ice water (80 mL) and extracted with $CH_2Cl_2$ (3×50 mL). The combined organic layers were washed with water (2×40 mL), dried over $MgSO_{4(s)}$, filtered, and concentrated under reduced pressure to afford a residue. The residue was purified by Isco Combi-Flash Companion column chromatography (0-2% EtOAc in $CH_2Cl_2$) to give 2-bromo-1-(2,4-dimethyl-thiazol-5-yl)ethanone (2.23 g, 57%) as a yellow oil.

$^1$H NMR (CDCl$_3$, 400 MHz) δ 4.21 (s, 2H), 2.72 (s, 6H).

Step 3. N-(2-Ethylphenyl)-2',4'-dimethyl-4,5'-bi-1,3-thiazol-2-amine

Following the procedure B, 2-bromo-1-(2,4-dimethyl-thiazol-5-yl)ethanone (72.1 mg, 0.308 mmol), ethanol (3.0 mL), and 1-(2-ethylphenyl)thiourea (50.5 mg, 0.280 mmol) were used to carry out the reaction. After the solution was stirred for 30 min and then worked up, the residue was purified by Isco Combi-Flash Companion column chromatography (20-40% EtOAc in n-hexane) to give N-(2-ethylphenyl)-2',4'-dimethyl-4,5'-bi-1,3-thiazol-2-amine (59.2 mg, 67%) as a yellow solid.

$^1$H NMR (CDCl$_3$, 300 MHz) δ 7.61 (d, 1H), 7.29-7.25 (m, 2H), 7.17 (dd, 1H), 6.98 (br s, 1H), 6.52 (s, 1H), 2.72-2.64 (m, 5H), 2.58 (s, 3H), 1.25 (t, 3H); LC-MS (ESI) m/z: 316.1 [M+H]$^+$.

EXAMPLE 2

N-(2-Methoxy-6-methylphenyl)-2',4'-dimethyl-4,5'-bi-1,3-thiazol-2-amine

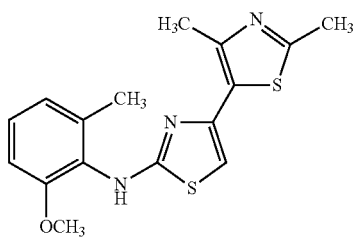

Compound 4

Step 1. 1-(2-Methoxy-6-methylphenyl)thiourea

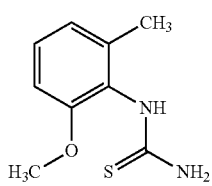

Compound 5

Following the procedure A, 2-methoxy-6-methylaniline (1.00 g, 7.29 mmol), 1.0 N HCl$_{(aq)}$ (7.0 mL), and ammonium thiocyanate (0.610 g, 8.01 mmol) were used to carry out the reaction. After the reaction was stirred for 18 hours and work-up, 1-(2-methoxy-6-methyl-phenyl)thiourea (0.860 g, 60%) was afforded as a pink solid.

$^1$H NMR (CDCl$_3$, 300 MHz) δ 7.38 (br s, 1H), 7.27-7.22 (m, 1H), 6.88 (d, 1H), 6.82 (d, 1H), 3.84 (s, 3H), 2.31 (s, 3H).

Step 2. N-(2-Methoxy-6-methylphenyl)-2',4'-dimethyl-4,5'-bi-1,3-thiazol-2-amine

Following the procedure B, 2-bromo-1-(2,4-dimethyl-thiazol-5-yl)ethanone (114 mg, 0.489 mmol), ethanol (6.0 mL), and 1-(2-methoxy-6-methylphenyl)thiourea (87.3 mg, 0.445 mmol) were used to carry out the reaction. After the solution was stirred for 30 min and work-up, the residue was purified by Isco Combi-Flash Companion column chromatography (20-40% EtOAc in n-hexane) to give N-(2-methoxy-6-methylphenyl)-2',4'-dimethyl-4,5'-bi-1,3-thiazol-2-amine (105 mg, 71%) as a lightly green solid.

$^1$H NMR (CDCl$_3$, 400 MHz) δ 7.20 (dd, 1H), 6.90 (d, 1H), 6.81 (d, 1H), 6.73 (br s, 1H) 6.47 (s, 1H), 3.81 (s, 3H), 2.65 (s, 3H), 2.56 (s, 3H), 2.35 (s, 3H); LC-MS (ESI) m/z: 332.0 [M+H]$^+$.

EXAMPLE 3

N-(2-Phenoxyphenyl)-2',4'-dimethyl-4,5'-bi-1,3-thiazol-2-amine

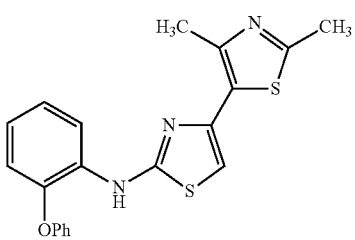

Compound 6

Step 1. 1-(2-Phenoxyphenyl)thiourea

Compound 7

Following the procedure A, 2-phenoxyaniline (0.851 g, 4.59 mmol), 1.0 N HCl$_{(aq)}$ (7.0 mL), and ammonium thiocyanate (0.384 g, 5.05 mmol) were used to carry out the reaction. After the reaction was stirred for 16 h and work-up, 1-(2-phenoxyphenyl)thiourea (0.520 g, 46%) was afforded as a white solid.

$^1$H NMR (CDCl$_3$, 400 MHz) δ 7.78 (br s, 1H), 7.45 (d, 1H), 7.38-7.34 (m, 2H), 7.26-7.13 (m, 3H), 7.03-6.94 (m, 3H), 6.18 (br s, 2H).

Step 2. N-(2-Phenoxyphenyl)-2',4'-dimethyl-4,5'-bi-1,3-thiazol-2-amine

Following the procedure B, 2-bromo-1-(2,4-dimethyl-thiazol-5-yl)ethanone (118 mg, 0.503 mmol), ethanol (3.0 mL), and 1-(2-phenoxyphenyl)thiourea (123 mg, 0.502 mmol) were used to carry out the reaction. After the solution was stirred for 30 min and work-up, the residue was purified by Isco Combi-Flash Companion column chromatography (15-30% EtOAc in n-hexane) to give N-(2-phenoxyphenyl)-2',4'-dimethyl-4,5'-bi-1,3-thiazol-2-amine (91.4 mg, 48%) as a white solid.

$^1$H NMR (CDCl$_3$, 300 MHz) δ 8.23 (d, 1H), 7.75 (br s, 1H), 7.37 (dd, 2H), 7.23-7.10 (m, 2H), 7.05 (d, 2H), 6.96 (t, 1H), 6.88 (d, 1H), 6.62 (s, 1H), 2.67 (s, 3H), 2.61 (s, 3H); LC-MS (ESI) m/z: 380.0 [M+H]$^+$.

EXAMPLE 4

N-(2-Chlorophenyl)-2',4'-dimethyl-4,5'-bi-1,3-thiazol-2-amine

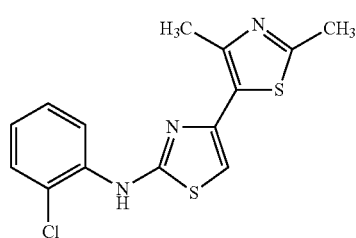

Compound 8

Following the procedure B, 2-bromo-1-(2,4-dimethyl-thiazol-5-yl)ethanone (126 mg, 0.537 mmol), ethanol (3.0 mL), and 1-(2-chlorophenyl)thiourea (100 mg, 0.537 mmol) were used to carry out the reaction. After the solution was stirred for 1 d and work-up, the crude product was purified by recystallization with CH$_2$Cl$_2$/diethyl ether to give N-(2-chlorophenyl)-2',4'-dimethyl-4,5'-bi-1,3-thiazol-2-amine (135 mg, 78%) as a lightly yellow solid.

$^1$H NMR (CDCl$_3$, 300 MHz) δ 8.22 (d, 1H), 7.58 (br s, 1H), 7.41 (d, 1H), 7.32 (dd, 1H), 6.99 (dd, 1H), 6.66 (s, 1H), 2.68 (s, 3H), 2.62 (s, 3H); LC-MS (ESI) m/z: 322.2 [M+H]$^+$.

EXAMPLE 5

N-(2-Fluorophenyl)-2',4'-dimethyl-4,5'-bi-1,3-thiazol-2-amine

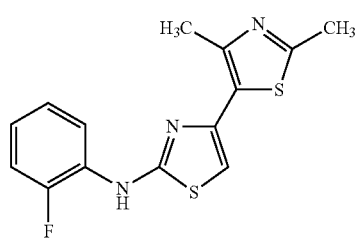

Compound 9

Following the procedure B, 2-bromo-1-(2,4-dimethyl-thiazol-5-yl)ethanone (138 mg, 0.591 mmol), ethanol (3.0 mL), and 1-(2-fluorophenyl)thiourea (101 mg, 0.591 mmol) were used to carry out the reaction. After the solution was stirred for 1 d and work-up, the crude product was purified by recystallization with CH$_2$Cl$_2$/diethyl ether to give N-(2-fluorophenyl)-2',4'-dimethyl-4,5'-bi-1,3-thiazol-2-amine (121 mg, 67%) as a yellow solid. 1H NMR (CDCl$_3$, 300 MHz) δ 8.15 (dd, 1H), 7.32 (br s, 1H), 7.21-7.09 (m, 2H), 7.04-6.98 (m, 1H), 6.64 (s, 1H), 2.68 (s, 3H), 2.61 (s, 3H); LC-MS (ESI) m/z: 306.2 [M+H]$^+$.

EXAMPLE 6

N-(5-Fluoro-2-methylphenyl)-2',4'-dimethyl-4,5'-bi-1,3-thiazol-2-amine

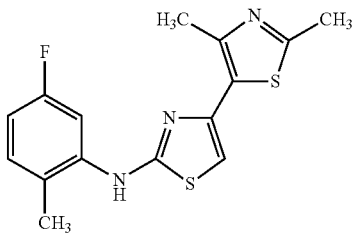

Compound 10

Step 1. 1-(5-Fluoro-2-methylphenyl)thiourea

Compound 11

Following the procedure A, 5-fluoro-2-methylaniline (0.650 g, 5.19 mmol), 1.0 N HCl$_{(aq)}$ (6.0 mL), and ammonium thiocyanate (0.435 g, 5.73 mmol) were used to carry out the reaction. After the reaction was stirred for overnight and work-up, 1-(5-fluoro-2-methylphenyl)thiourea (0.520 g, 46%) was afforded as a gray solid.

$^1$H NMR (DMSO-d$_6$, 400 MHz) δ 9.24 (s, 1H), 7.26-7.09 (m, 2H), 7.02-6.94 (m, 1H), 2.14 (s, 3H).

Step 2. N-(5-Fluoro-2-methylphenyl)-2',4'-dimethyl-4,5'-bi-1,3-thiazol-2-amine

Following the procedure B, 2-bromo-1-(2,4-dimethyl-thiazol-5-yl)ethanone (114 mg, 0.486 mmol), ethanol (3.0 mL), and 1-(5-fluoro-2-methylphenyl)thiourea (89.6 mg, 0.486 mmol) were used to carry out the reaction. After the solution was stirred for 1 h and work-up, the crude product was purified by recystallization with CH$_2$Cl$_2$/diethyl ether to give N-(5-fluoro-2-methylphenyl)-2',4'-dimethyl-4,5'-bi-1,3-thiazol-2-amine (101 mg, 65%) as a yellow solid.

$^1$H NMR (CDCl$_3$, 400 MHz) δ 7.65 (dd, 1H), 7.16 (dd, 1H), 6.96 (br s, 1H), 6.74 (td, 1H), 6.62 (s, 1H), 2.68 (s, 3H), 2.60 (s, 3H), 2.29 (s, 3H); LC-MS (ESI) m/z: 320.0 [M+H]$^+$.

EXAMPLE 7

N-(5-Methoxy-2-methylphenyl)-2',4'-dimethyl-4,5'-bi-1,3-thiazol-2-amine

Compound 12

Step 1. 1-(5-Methoxy-2-methylphenyl)thiourea

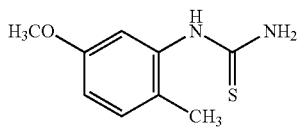

Compound 13

Following the procedure A, 5-methoxy-2-methylaniline (0.700 g, 5.10 mmol), 1.0 N HCl$_{(aq)}$ (6.0 mL), and ammonium thiocyanate (0.427 g, 5.61 mmol) were used to carry out the reaction. After the reaction was stirred for overnight and work-up, 1-(5-methoxy-2-methylphenyl)thiourea (0.425 g, 42%) was afforded as a gray solid.

$^1$H NMR (DMSO-d$_6$, 400 MHz) δ 9.18 (br s, 1H), 7.12 (d, 1H), 6.81 (d, 1H), 6.74 (dd, 1H), 3.70 (s, 3H), 2.09 (s, 3H).

Step 2. N-(5-Methoxy-2-methylphenyl)-2',4'-dimethyl-4,5'-bi-1,3-thiazol-2-amine Following the procedure B, 2-bromo-1-(2,4-dimethylthiazol-5-yl)ethanone (113 mg, 0.481 mmol), ethanol (3.0 mL), and 1-(5-methoxy-2-methylphenyl)thiourea (94.5 mg, 0.481 mmol) were used to carry out the reaction. After the solution was stirred for 1 h and work-up, the crude product was purified by recrystallization with CH$_2$Cl$_2$/diethyl ether to give N-(5-methoxy-2-methylphenyl)-2',4'-dimethyl-4,5'-bi-1,3-thiazol-2-amine (88.7 mg, 56%) as a lightly yellow solid.

$^1$H NMR (CDCl$_3$, 400 MHz) δ 7.38 (d, 1H), 7.13 (d, 1H), 6.96 (br s, 1H), 6.62 (dd, 1H), 6.58 (s, 1H), 3.83 (s, 3H), 2.67 (s, 3H), 2.59 (s, 3H), 2.26 (s, 3H); LC-MS (ESI) m/z: 332.2 [M+H]$^+$.

EXAMPLE 8

N-(2,4-Dimethoxyphenyl)-2',4'-dimethyl-4,5'-bi-1,3-thiazol-2-amine

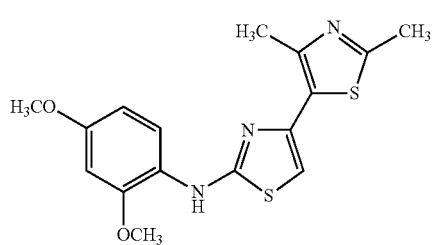

Compound 14

Following the procedure B, 2-bromo-1-(2,4-dimethylthiazol-5-yl)ethanone (109 mg, 0.466 mmol), ethanol (3.0 mL), and 1-(2,4-dimethoxyphenyl)thiourea (98.9 mg, 0.466 mmol) were used to carry out the reaction. After the solution was stirred for 1.5 h and work-up, the residue was purified by Isco Combi-Flash Companion column chromatography (5-60% EtOAc in n-hexane) to give N-(2,4-dimethoxyphenyl)-2',4'-dimethyl-4,5'-bi-1,3-thiazol-2-amine (85.3 mg, 53%) as a white solid.

$^1$H NMR (CDCl$_3$, 400 MHz) δ 7.87 (d, 1H), 7.41 (br s, 1H), 6.58-6.53 (m, 3H), 3.88 (s, 3H), 3.82 (s, 3H), 2.67 (s, 3H), 2.60 (s, 3H); LC-MS (ESI) m/z: 348.1 [M+H]$^+$.

EXAMPLE 9

N-(5-Chloro-2-methylphenyl)-2',4'-dimethyl-4,5'-bi-1,3-thiazol-2-amine

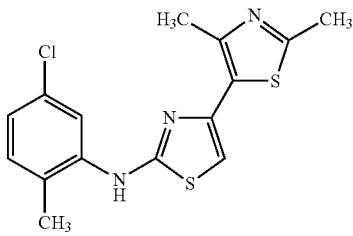

Compound 15

Step 1. 1-(5-Chloro-2-methylphenyl)thiourea

Compound 16

Following the procedure A, 5-chloro-2-methylaniline (0.760 g, 5.37 mmol), 1.0 N HCl$_{(aq)}$ (6.0 mL), and ammonium thiocyanate (0.450 g, 5.90 mmol) were used to carry out the reaction. After the reaction was stirred for 20 h and work-up, the crude product was purified by Isco Combi-Flash Companion column chromatography (20-60% EtOAc in n-hexane) to give 1-(5-chloro-2-methylphenyl)thiourea (0.460 g, 43%) as a white solid.

$^1$H NMR (CDCl$_3$, 300 MHz) δ 7.63 (br s, 1H), 7.26-7.23 (m overlapped with s at 7.26, 3H), 5.90 (br s, 2H), 2.29 (s, 3H).

Step 2. N-(5-Chloro-2-methylphenyl)-2',4'-dimethyl-4,5'-bi-1,3-thiazol-2-amine Following the procedure B, 2-bromo-1-(2,4-dimethylthiazol-5-yl)ethanone (103 mg, 0.440 mmol), ethanol (3.0 mL), and 1-(5-chloro-2-methylphenyl)thiourea (88.4 mg, 0.440 mmol) were used to carry out the reaction. After the solution was stirred for 2 h and work-up, the crude product was purified by recrystallization with CH$_2$Cl$_2$/diethyl ether to give N-(5-chloro-2-methylphenyl)-2',4'-dimethyl-4,5'-bi-1,3-thiazol-2-amine (92.3 mg, 62%) as a lightly yellow solid.

$^1$H NMR (CDCl$_3$, 400 MHz) δ 7.87 (s, 1H), 7.15 (d, 1H), 7.02 (d, 1H), 6.91 (br s, 1H), 6.61 (s, 1H), 2.68 (s, 3H), 2.61 (s, 3H), 2.29 (s, 3H); LC-MS (ESI) m/z: 336.0 [M+H]$^+$.

EXAMPLE 10

2',4'-Dimethyl-N-(2,4,6-trimethylphenyl)-4,5'-bi-1,3-thiazol-2-amine

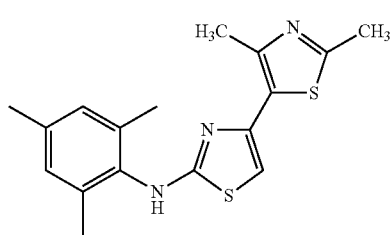

Compound 17

Step 1. 1-(2,4,6-Trimethylphenyl)thiourea

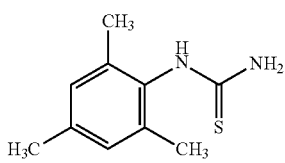

Compound 18

Following the procedure A, 2,4,6-trimethylaniline (0.700 mL, 4.99 mmol), 1.0 N HCl$_{(aq)}$ (6.0 mL), and ammonium thiocyanate (0.418 g, 5.48 mmol) were used to carry out the reaction. After the reaction was stirred for 20 h and work-up, 1-(2,4,6-trimethyl-phenyl)thiourea (0.720 g, 74%) was obtained as a white solid.

$^1$H NMR (CDCl$_3$, 400 MHz) δ 7.40 (br s, 1H), 6.95 (s, 2H,), 6.00 (br s, 1H), 5.35 (br s, 1H), 2.29 (s, 3H), 2.25 (s, 6H).

Step 2. 2',4'-Dimethyl-N-(2,4,6-trimethylphenyl)-4,5'-bi-1,3-thiazol-2-amine

Following the procedure B, 2-bromo-1-(2,4-dimethyl-thiazol-5-yl)ethanone (96.9 mg, 0.414 mmol), ethanol (3.0 mL), and 1-(2,4,6-trimethylphenyl)thiourea (80.5 mg, 0.414 mmol) were used to carry out the reaction. After the solution was stirred for 2 h and work-up, the residue was purified by Isco Combi-Flash Companion column chromatography (15-45% EtOAc in n-hexane) to give 2',4'-dimethyl-N-(2,4,6-trimethylphenyl)-4,5'-bi-1,3-thiazol-2-amine (113 mg, 83%) as a white solid.

$^1$H NMR (CDCl$_3$, 400 MHz) δ 6.97 (s, 2H), 6.65 (br s, 1H), 6.41 (s, 1H), 2.65 (s, 3H), 2.56 (s, 3H), 2.32 (s, 3H), 2.27 (s, 6H); LC-MS (ESI) m/z: 330.1 [M+H]$^+$.

EXAMPLE 11

N-(5-Bromo-2-methylphenyl)-2',4'-dimethyl-4,5'-bi-1,3-thiazol-2-amine

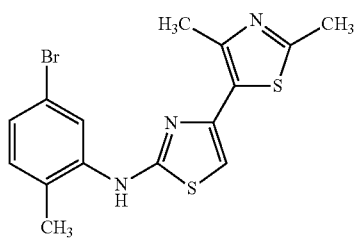

Compound 19

Step 1. 1-(5-Bromo-2-methylphenyl)thiourea

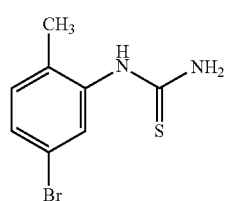

Compound 20

Following the procedure A, 5-bromo-2-methylaniline (0.500 g, 2.69 mmol), 1.0 N HCl$_{(aq)}$ (5.0 mL), and ammonium thiocyanate (0.230 g, 2.96 mmol) were used to carry out the reaction. After the reaction was stirred for overnight and work-up, 1-(5-bromo-2-methylphenyl)thiourea (0.213 g, 32%) was obtained as a white solid.

$^1$H NMR (CDCl$_3$, 400 MHz) δ 7.93 (br s, 1H), 7.43-7.40 (m, 2H,), 7.19 (d, 1H), 5.97 (br s, 2H), 2.28 (s, 3H).

Step 2. N-(5-Bromo-2-methylphenyl)-2',4'-dimethyl-4,5'-bi-1,3-thiazol-2-amine

Following the procedure B, 2-bromo-1-(2,4-dimethyl-thiazol-5-yl)ethanone (103 mg, 0.442 mmol), ethanol (3.0 mL), and 1-(5-bromo-2-methylphenyl)thiourea (108 mg, 0.442 mmol) were used to carry out the reaction. After the solution was stirred for 2 h and work-up, the residue was purified by Isco Combi-Flash Companion column chromatography (20-40% EtOAc in n-hexane) to give N-(5-bromo-2-methylphenyl)-2',4'-dimethyl-4,5'-bi-1,3-thiazol-2-amine (138 mg, 82%) as a yellow solid.

$^1$H NMR (CDCl$_3$, 300 MHz) δ 8.02 (d, 1H), 7.18 (dd, 1H), 7.09 (d, 1H), 6.91 (br s, 1H), 6.61 (s, 1H), 2.67 (s, 3H), 2.61 (s, 3H), 2.28 (s, 3H); LC-MS (ESI) m/z: 379.9 [M+H]$^+$.

EXAMPLE 12

N-(3-Fluoro-2-methylphenyl)-2',4'-dimethyl-4,5'-bi-1,3-thiazol-2-amine

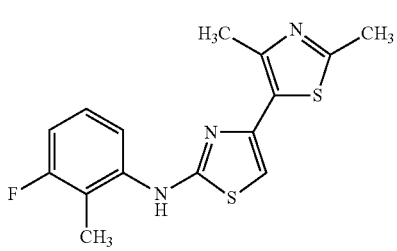

Compound 21

Step 1. 1-(3-Fluoro-2-methylphenyl)thiourea

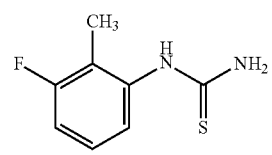

Compound 22

Following the procedure A, 3-fluoro-2-methylaniline (0.520 g, 4.16 mmol), 1.0 N HCl$_{(aq)}$ (6.0 mL), and ammonium thiocyanate (0.350 g, 4.60 mmol) were used to carry out the reaction. After the reaction was stirred for 18 h and work-up, 1-(3-fluoro-2-methylphenyl)thiourea (0.260 g, 34%) was obtained as a white solid.

$^1$H NMR (CDCl$_3$, 400 MHz) δ 7.94 (br s, 1H), 7.27-7.22 (m, 1H), 7.09-7.00 (m, 2H), 5.98 (br s, 2H), 2.25 (s, 3H).

Step 2. N-(3-Fluoro-2-methylphenyl)-2',4'-dimethyl-4,5'-bi-1,3-thiazol-2-amine

Following the procedure B, 2-bromo-1-(2,4-dimethyl-thiazol-5-yl)ethanone (109 mg, 0.464 mmol), ethanol (3.0 mL), and 1-(3-fluoro-2-methylphenyl)thiourea (109 mg, 0.464 mmol) were used to carry out the reaction. After the solution was stirred for 2 h and work-up, the residue was purified by Isco Combi-Flash Companion column chromatography (20-40% EtOAc in n-hexane) to give N-(3-fluoro-2-methylphenyl)-2',4'-dimethyl-4,5'-bi-1,3-thiazol-2-amine (127 mg, 86%) as a yellow solid.

$^1$H NMR (CDCl$_3$, 400 MHz) δ 7.49 (d, 1H), 7.24-7.18 (m, 1H), 6.99 (br s, 1H), 6.87 (dd, 1H), 6.59 (s, 1H), 2.67 (s, 3H), 2.59 (s, 3H), 2.24 (s, 3H); LC-MS (ESI) m/z: 320.2 [M+H]$^+$.

EXAMPLE 13

N-(2,6-Diisopropylphenyl)-2',4'-dimethyl-4,5'-bi-1,3-thiazol-2-amine

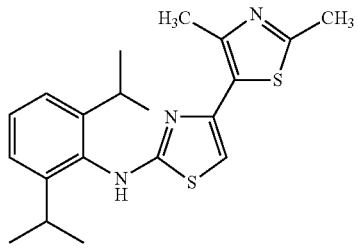

Compound 23

Step 1. 1-(2,6-Diisopropylphenyl)thiourea

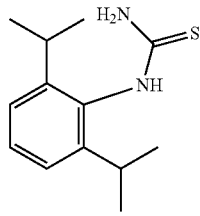

Compound 24

Following the procedure A, 2,6-diisopropylaniline (0.600 mL, 3.18 mmol), 1.0 N HCl$_{(aq)}$ (6.0 mL), and ammonium thiocyanate (0.270 g, 3.55 mmol) were used to carry out the reaction. After the reaction was stirred for 20 h and work-up, 1-(2,6-diisopropyl-phenyl)thiourea (0.280 g, 37%) was obtained as a brown solid.

$^1$H NMR (CDCl$_3$, 300 MHz) δ 7.47 (br s, 1H), 7.38 (dd, 1H), 7.24 (d, 2H), 6.20-5.80 (br s, 1H), 5.60-5.10 (br s, 1H), 3.16 (septet, 2H), 1.24 (d, 6H), 1.18 (d, 6H).

Step 2. N-(2,6-Diisopropylphenyl)-2',4'-dimethyl-4,5'-bi-1,3-thiazol-2-amine

Following the procedure B, 2-bromo-1-(2,4-dimethyl-thiazol-5-yl)ethanone (79.6 mg, 0.340 mmol), ethanol (3.0 mL), and 1-(2,6-diisopropylphenyl)thiourea (80.3 mg, 0.340 mmol) were used to carry out the reaction. After the solution was stirred for 4 h and work-up, the residue was purified by Isco Combi-Flash Companion column chromatography (10-40% EtOAc in n-hexane) to give N-(2,6-diisopropylphenyl)-2',4'-dimethyl-4,5'-bi-1,3-thiazol-2-amine (106 mg, 84%) as a yellow solid.

$^1$H NMR (CDCl$_3$, 400 MHz) δ 7.38 (dd, 1H), 7.25 (d overlapped with solvent peak, 2H), 6.73 (br s, 1H), 6.41 (s, 1H), 3.27 (septet, 2H), 2.72 (s, 3H), 2.57 (s, 3H), 1.20 (d, 12H); LC-MS (ESI) m/z: 372.1 [M+H]$^+$.

EXAMPLE 14

N-(2,5-Dimethylphenyl)-2',4'-dimethyl-4,5'-bi-1,3-thiazol-2-amine

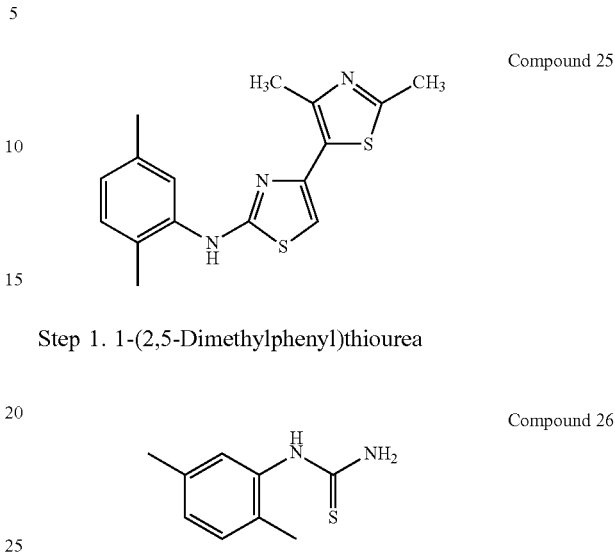

Compound 25

Step 1. 1-(2,5-Dimethylphenyl)thiourea

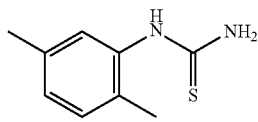

Compound 26

Following the procedure A, 2,5-dimethylaniline (0.500 mL, 4.01 mmol), 1.0 N HCl$_{(aq)}$ (6.0 mL), and ammonium thiocyanate (0.340 g, 4.47 mmol) were used to carry out the reaction. After the reaction was stirred for 20 h and work-up, the crude product was purified by Isco Combi-Flash Companion column chromatography (20-60% EtOAc in n-hexane) to give 1-(2,5-dimethylphenyl)thiourea (0.300 g, 42%) as a white solid.

$^1$H NMR (CDCl$_3$, 300 MHz) δ 7.76 (br s, 1H), 7.34 (br s, 1H), 7.27 (d, 1H), 7.17 (d, 1H), 7.12 (s, 1H), 6.30-5.60 (br s, 2H), 2.40 (s, 3H), 2.35 (s, 3H).

Step 2. N-(2,5-Dimethylphenyl)-2',4'-dimethyl-4,5'-bi-1,3-thiazol-2-amine

Following the procedure B, 2-bromo-1-(2,4-dimethyl-thiazol-5-yl)ethanone (108 mg, 0.459 mmol), ethanol (3.0 mL), and 1-(2,5-dimethylphenyl)thiourea (82.8 mg, 459 mmol) were used to carry out the reaction. After the solution was stirred for 2 h and work-up, the residue was purified by Isco Combi-Flash Companion column chromatography (10-40% EtOAc in n-hexane) to give N-(2,5-dimethylphenyl)-2',4'-dimethyl-4,5'-bi-1,3-thiazol-2-amine (106 mg, 84%) as a yellow solid.

$^1$H NMR (CDCl$_3$, 300 MHz) δ 7.46 (s, 1H), 7.13 (d, 1H), 6.93 (br s, 1H), 6.92 (d overlapped with br s at 6.93, 1H), 6.54 (s, 1H), 2.67 (s, 3H), 2.59 (s, 3H), 2.35 (s, 3H), 2.28 (s, 3H); LC-MS (ESI) m/z: 316.1 [M+H]$^+$.

EXAMPLE 15

N-(4,5-Dimethoxy-2-methylphenyl)-2',4'-dimethyl-4,5'-bi-1,3-thiazol-2-amine

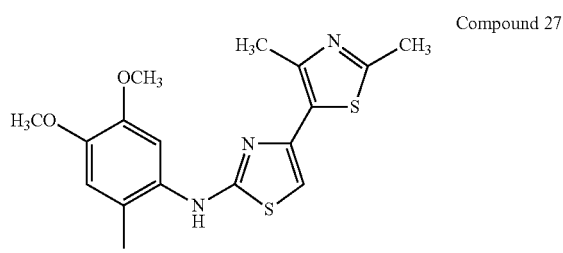 [SMILES: COc1cc(C)c(Nc2nc(-c3sc(C)nc3C)cs2)cc1OC]

Compound 27

Step 1. 1-(4,5-Dimethoxy-2-methylphenyl)thiourea

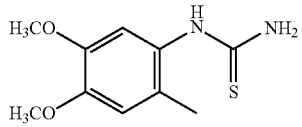

Compound 28

Following the procedure A, 4,5-dimethoxy-2-methylaniline (0.370 g, 2.21 mmol), 1.0 N HCl$_{(aq)}$ (3.0 mL), and ammonium thiocyanate (0.200 g, 2.63 mmol) were used to carry out the reaction. After the reaction was stirred for 20 h and work-up, 1-(4,5-dimethoxy-2-methylphenyl)thiourea (0.210 g, 42%) was afforded as a white solid.

$^1$H NMR (DMSO-d$_6$, 400 MHz) δ 9.09 (br s, 1H), 6.81 (s, 1H,), 6.70 (br s, 1H), 3.73 (s, 3H), 3.69 (s, 3H), 2.08 (s, 3H).

Step 2. N-(4,5-Dimethoxy-2-methylphenyl)-2',4'-dimethyl-4,5'-bi-1,3-thiazol-2-amine Following the procedure B, 2-bromo-1-(2,4-dimethyl-thiazol-5-yl)ethanone (83.6 mg, 0.357 mmol), ethanol (3.0 mL), and 1-(4,5-dimethoxy-2-methylphenyl)thiourea (80.8 mg, 0.357 mmol) were used to carry out the reaction. After the solution was stirred for 2 h and work-up, the residue was purified by Isco Combi-Flash Companion column chromatography (15-50% EtOAc in n-hexane) to give N-(4,5-dimethoxy-2-methylphenyl)-2',4'-dimethyl-4,5'-bi-1,3-thiazol-2-amine (89.2 mg, 69%) as a gray solid.

$^1$H NMR (CDCl$_3$, 400 MHz) δ 7.14 (s, 1H), 6.81 (br s, 1H), 6.75 (s, 1H), 6.48 (s, 1H), 3.89 (s, 3H), 3.87 (s, 3H), 2.66 (s, 3H), 2.57 (s, 3H), 2.26 (s, 3H); LC-MS (ESI) m/z: 362.1 [M+H]$^+$.

EXAMPLE 16

N-(2,4-Dimethylphenyl)-2',4'-dimethyl-4,5'-bi-1,3-thiazol-2-amine

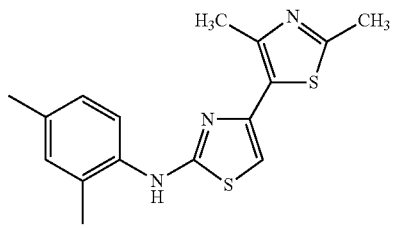

Compound 29

Step 1. 1-(2,4-Dimethylphenyl)thiourea

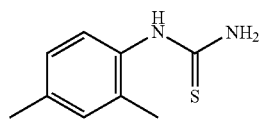

Compound 30

Following the procedure A, 2,4-dimethylphenylaniline (0.720 g, 5.94 mmol), 1.0 N HCl$_{(aq)}$ (7.0 mL), and ammonium thiocyanate (0.540 g, 7.09 mmol) were used to carry out the reaction. After the reaction was stirred for 20 h and work-up, 1-(2,4-dimethylphenyl)thiourea (0.270 g, 25%) was afforded as a white solid.

$^1$H NMR (CDCl$_3$, 400 MHz) δ 7.52 (br s, 1H), 7.18-7.05 (m, 3H), 6.20-5.40 (br s, 2H), 2.33 (s, 3H), 2.27 (s, 3H).

Step 2. N-(2,4-Dimethylphenyl)-2',4'-dimethyl-4,5'-bi-1,3-thiazol-2-amine

Following the procedure B, 2-bromo-1-(2,4-dimethyl-thiazol-5-yl)ethanone (106 mg, 0.452 mmol), ethanol (3.0 mL), and 1-(2,4-dimethylphenyl)thiourea (81.4 mg, 0.452 mmol) were used to carry out the reaction. After the solution was stirred for 2 h and work-up, the residue was purified by column chromatography (40% EtOAc in n-hexane) to give N-(2,4-dimethylphenyl)-2',4'-dimethyl-4,5'-bi-1,3-thiazol-2-amine (126 mg, 88%) as a red brown solid.

$^1$H NMR (CDCl$_3$, 300 MHz) δ 7.44 (d, 1H), 7.08-7.05 (m, 2H), 6.90 (br s, 1H), 6.50 (s, 1H), 2.66 (s, 3H), 2.57 (s, 3H), 2.33 (s, 3H), 2.29 (s, 3H); LC-MS (APCI) m/z: 316.1 [M+H]$^+$.

EXAMPLE 17

N-(4-Fluoro-2-methylphenyl)-2',4'-dimethyl-4,5'-bi-1,3-thiazol-2-amine

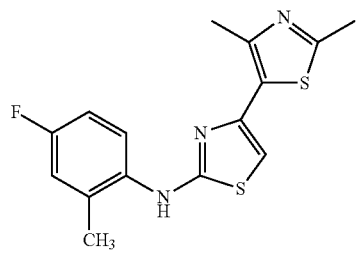

Compound 31

Step 1. 1-(4-Fluoro-2-methylphenyl)thiourea

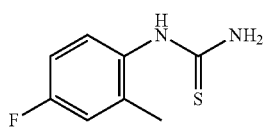

Compound 32

Following the procedure A, 4-fluoro-2-methylaniline (0.370 g, 4.08 mmol), 1.0 N HCl$_{(aq)}$ (6.0 mL), and ammonium thiocyanate (0.340 g, 4.48 mmol) were used to carry out the reaction. After the reaction was stirred for 20 h and work-up, 1-(4-fluoro-2-methylphenyl)thiourea (0.157 g, 21%) was afforded as a purple solid.

$^1$H NMR (CDCl$_3$, 300 MHz) δ 7.63 (br s, 1H), 7.24-7.19 (m, 1H), 7.05-6.97 (m, 2H), 6.20-5.40 (br s, 2H), 2.32 (s, 3H).

Step 2. N-(4-Fluoro-2-methylphenyl)-2',4'-dimethyl-4,5'-bi-1,3-thiazol-2-amine

Following the procedure B, 2-bromo-1-(2,4-dimethyl-thiazol-5-yl)ethanone (83.6 mg, 0.435 mmol), ethanol (3.0 mL), and 1-(4-fluoro-2-methylphenyl)thiourea (80.8 mg, 0.435 mmol) were used to carry out the reaction. After the solution was stirred for 3 h and work-up, the residue was purified by Isco Combi-Flash Companion column chromatography (10-50% EtOAc in n-hexane) to give N-(4-fluoro-2-methylphenyl)-2',4'-dimethyl-4,5'-bi-1,3-thiazol-2-amine (127 mg, 92%) as a dark brown solid.

$^1$H NMR (CDCl$_3$, 400 MHz) δ 7.52 (dd, 1H), 7.05-6.95 (m, 3H), 6.52 (s, 1H), 2.69 (s, 3H), 2.58 (s, 3H), 2.33 (s, 3H); LC-MS (APCI) m/z: 320.1 [M+H]$^+$.

EXAMPLE 18

N-(2-Fluoro-6-methylphenyl)-2',4'-dimethyl-4,5'-bi-1,3-thiazol-2-amine

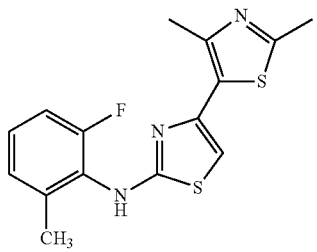

Compound 33

Step 1. 1-(2-Fluoro-6-methylphenyl)thiourea

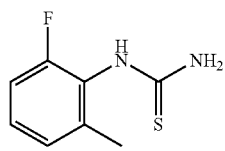

Compound 34

Following the procedure A, 2-fluoro-6-methylaniline (0.440 g, 3.51 mmol), 1.0 N $HCl_{(aq)}$ (5.0 mL), and ammonium thiocyanate (0.294 g, 3.87 mmol) were used to carry out the reaction. After the reaction was stirred for 16 h and work-up, 1-(2-fluoro-6-methylphenyl)thiourea (0.266 g, 41%) was afforded as a white solid.

$^1$H NMR (CDCl$_3$, 300 MHz) δ 7.52 (br s, 1H), 7.38-7.23 (m, 1H), 7.10 (d, 1H), 7.04 (t, 1H), 6.30-5.60 (br s, 1H), 2.35 (s, 3H).

Step 2. N-(2-Fluoro-6-methylphenyl)-2',4'-dimethyl-4,5'-bi-1,3-thiazol-2-amine

Following the procedure B, 2-bromo-1-(2,4-dimethylthiazol-5-yl)ethanone (105 mg, 0.447 mmol), ethanol (3.0 mL), and 1-(2-fluoro-6-methylphenyl)thiourea (82.4 mg, 0.447 mmol) were used to carry out the reaction. After the solution was stirred for 3 h and work-up, the residue was purified by Isco Combi-Flash Companion column chromatography (10-35% EtOAc in n-hexane) to give N-(2-fluoro-6-methylphenyl)-2',4'-dimethyl-4,5'-bi-1,3-thiazol-2-amine (105 mg, 74%) as a beige solid.

$^1$H NMR (CDCl$_3$, 400 MHz) δ 7.24-7.19 (m, 1H), 7.09 (d, 1H), 7.03 (dd, 1H), 6.68 (br s, 1H), 6.52 (s, 1H), 2.65 (s, 3H), 2.56 (s, 3H), 2.37 (s, 3H); LC-MS (APCI) m/z: 320.1 [M+H]$^+$.

EXAMPLE 19

N-(4-Methoxy-2-methylphenyl)-2',4'-dimethyl-4,5'-bi-1,3-thiazol-2-amine

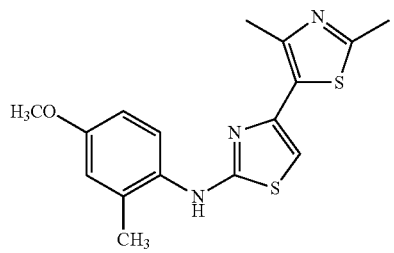

Compound 35

Step 1. 1-(4-Methoxy-2-methylphenyl)thiourea

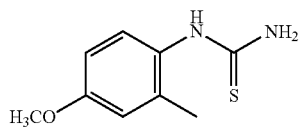

Compound 36

Following the procedure A, 4-methoxy-2-methylaniline (0.830 g, 6.05 mmol), 1.0 N $HCl_{(aq)}$ (7.0 mL), and ammonium thiocyanate (0.510 g, 6.66 mmol) were used to carry out the reaction. After the reaction was stirred for 20 h and work-up, 1-(4-methoxy-2-methylphenyl)thiourea (0.450 g, 38%) was afforded as a purple solid.

$^1$H NMR (DMSO-d$_6$, 400 MHz) δ 9.06 (br s, 1H), 7.02 (d, 1H), 6.81 (d, 1H), 6.73 (dd, 1H), 3.72 (s, 3H), 2.13 (s, 3H).

Step 2. N-(4-Methoxy-2-methylphenyl)-2',4'-dimethyl-4,5'-bi-1,3-thiazol-2-amine

Following the procedure B, 2-bromo-1-(2,4-dimethylthiazol-5-yl)ethanone (101 mg, 0.431 mmol), ethanol (3.0 mL), and 1-(4-methoxy-2-methylphenyl)thiourea (84.5 mg, 0.431 mmol) were used to carry out the reaction. After the solution was stirred for 1 h and work-up, the residue was purified by Isco Combi-Flash Companion column chromatography (10-50% EtOAc in n-hexane) to give N-(4-methoxy-2-methylphenyl)-2',4'-dimethyl-4,5'-bi-1,3-thiazol-2-amine (117 mg, 82%) as a brown solid.

$^1$H NMR (CDCl$_3$, 400 MHz) δ 7.39 (d, 1H), 6.83-6.77 (m, 2H), 6.72 (br s, 1H), 6.47 (s, 1H), 3.82 (s, 3H), 2.66 (s, 3H), 2.57 (s, 3H), 2.31 (s, 3H); LC-MS (APCI) m/z: 332.1 [M+H]$^+$.

EXAMPLE 20

2',4'-Dimethyl-N-(3,4,5-trimethoxyphenyl)-4,5'-bi-1,3-thiazol-2-amine

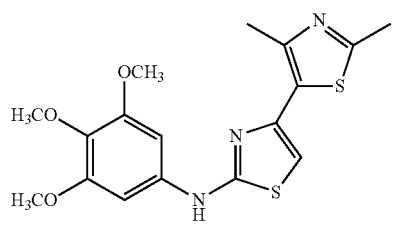

Compound 37

Step 1. 1-(3,4,5-Trimethoxyphenyl)thiourea

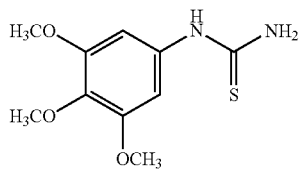

Compound 38

Following the procedure A, 3,4,5-trimethoxyaniline (0.730 g, 3.98 mmol), 1.0 N $HCl_{(aq)}$ (5.0 mL), and ammonium thiocyanate (0.330 g, 4.33 mmol) were used to carry out the reaction. After the reaction was stirred for 20 h and work-up, 1-(3,4,5-trimethoxy-phenyl)thiourea (0.630 g, 66%) was afforded as a gray solid.

$^1$H NMR (DMSO-$d_6$, 400 MHz) δ 9.56 (br s, 1H), 6.68 (s, 2H), 3.73 (s, 6H), 3.62 (s, 3H).

Step 2. 2',4'-Dimethyl-N-(3,4,5-trimethoxyphenyl)-4,5'-bi-1,3-thiazol-2-amine

Following the procedure B, 2-bromo-1-(2,4-dimethyl-thiazol-5-yl)ethanone (96.2 mg, 0.411 mmol), ethanol (3.0 mL), and 1-(3,4,5-trimethoxyphenyl)thiourea (99.6 mg, 0.411 mmol) were used to carry out the reaction. After the solution was stirred for 3 h and work-up, the residue was purified by Isco Combi-Flash Companion column chromatography (15-80% EtOAc in n-hexane) to give 2',4'-dimethyl-N-(3,4,5-trimethoxyphenyl)-4,5'-bi-1,3-thiazol-2-amine (136 mg, 88%) as a pink solid.

$^1$H NMR (CDCl$_3$, 300 MHz) δ 7.08 (br s, 1H), 6.73 (s, 2H), 6.57 (s, 1H), 3.89 (s, 6H), 3.84 (s, 3H), 2.67 (s, 3H), 2.60 (s, 3H); LC-MS (ESI) m/z: 378.1 [M+H]$^+$.

EXAMPLE 21

N-(3,5-Dimethylphenyl)-2',4'-dimethyl-4,5'-bi-1,3-thiazol-2-amine

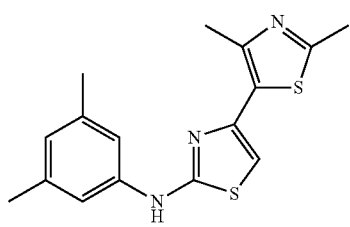

Compound 39

Step 1. 1-(3,5-Dimethylphenyl)thiourea

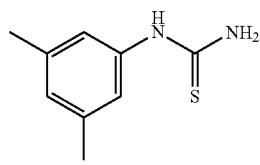

Compound 40

Following the procedure A, 3,5-dimethylaniline (0.701 g, 5.78 mmol), 1.0 N HCl$_{(aq)}$ (7.0 mL), and ammonium thiocyanate (0.480 g, 6.35 mmol) were used to carry out the reaction. After the reaction was stirred for 20 h and work-up, 1-(3,5-dimethylphenyl)thiourea (0.410 g, 39%) was afforded as a white solid.

$^1$H NMR (CDCl$_3$, 300 MHz) δ 7.82 (br s, 1H), 6.95 (s, 1H), 6.83 (s, 2H), 6.09 (br s, 2H), 2.32 (s, 6H).

Step 2. N-(3,5-Dimethylphenyl)-2',4'-dimethyl-4,5'-bi-1,3-thiazol-2-amine

Following the procedure B, 2-bromo-1-(2,4-dimethyl-thiazol-5-yl)ethanone (91.6 mg, 0.447 mmol), ethanol (3.0 mL), and 1-(3,5-dimethylphenyl)thiourea (70.5 mg, 0.447 mmol) were used to carry out the reaction. After the solution was stirred for 2 h and work-up, the residue was purified by Isco Combi-Flash Companion column chromatography (10-40% EtOAc in n-hexane) to give N-(3,5-dimethylphenyl)-2',4'-dimethyl-4,5'-bi-1,3-thiazol-2-amine (119 mg, 85%) as a yellow solid.

$^1$H NMR (CDCl$_3$, 400 MHz) δ 7.19 (br s, 1H), 6.98 (s, 2H), 6.74 (s, 1H), 6.56 (s, 1H), 2.67 (s, 3H), 2.60 (s, 3H), 2.33 (s, 6H); LC-MS (ESI) m/z: 316.0 [M+H]$^+$.

EXAMPLE 22

N-(2,6-Dimethylphenyl)-2',4'-dimethyl-4,5'-bi-1,3-thiazol-2-amine

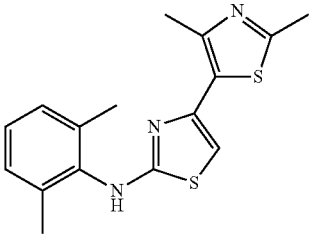

Compound 41

Following the procedure B, 2-bromo-1-(2,4-dimethyl-thiazol-5-yl)ethanone (116 mg, 0.496 mmol), ethanol (3.0 mL), and 1-(2,6-dimethylphenyl)thiourea (89.5 mg, 0.496 mmol) were used to carry out the reaction. After the solution was stirred for 3 h and work-up, the crude product was purified by recrystallization with CH$_2$Cl$_2$/diethyl ether to give N-(2,6-dimethyl-phenyl)-2',4'-dimethyl-4,5'-bi-1,3-thiazol-2-amine (116 mg, 74%) as a yellow solid.

$^1$H NMR (CDCl$_3$, 400 MHz) δ 7.21-7.10 (m, 3H), 6.69 (br s, 1H), 6.43 (s, 1H), 2.66 (s, 3H), 2.56 (s, 3H), 2.32 (s, 6H); LC-MS (ESI) m/z: 316.0 [M+H]$^+$.

EXAMPLE 23

N-(4-Bromo-2-methylphenyl)-2',4'-dimethyl-4,5'-bi-1,3-thiazol-2-amine

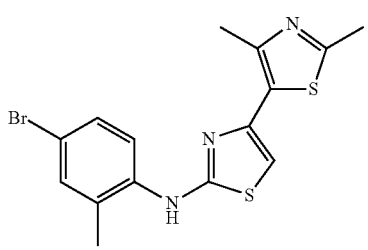

Compound 42

Following the procedure B, 2-bromo-1-(2,4-dimethyl-thiazol-5-yl)ethanone (130 mg, 0.556 mmol), ethanol (3.0 mL), and 1-(4-bromo-2-methylphenyl)thiourea (136 mg, 0.556 mmol) were used to carry out the reaction. After the solution was stirred for 3 h and work-up, the residue was purified by Isco Combi-Flash Companion column chromatography (10-40% EtOAc in n-hexane) to give N-(4-bromo-2-methylphenyl)-2',4'-dimethyl-4,5'-bi-1,3-thiazol-2-amine (191 mg, 90%) as a beige solid.

$^1$H NMR (CDCl$_3$, 400 MHz) δ 7.61 (d, 1H), 7.42-7.37 (m, 2H), 6.91 (br s, 1H), 6.58 (s, 1H), 2.67 (s, 3H), 2.58 (s, 3H), 2.31 (s, 3H); LC-MS (ESI) m/z: 380.0 [M+H]$^+$.

EXAMPLE 24

N-[4-Bromo-2-(trifluoromethyl)phenyl]-2',4'-dimethyl-4,5'-bi-1,3-thiazol-2-amine Compound 43

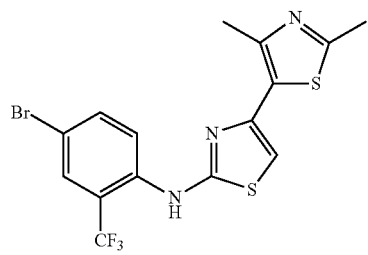

Following the procedure B, 2-bromo-1-(2,4-dimethyl-thiazol-5-yl)ethanone (69.2 mg, 0.296 mmol), ethanol (3.0 mL), and 4-bromo-2-(trifluoromethyl)phenylthiourea (88.4 mg, 0.296 mmol) were used to carry out the reaction. After the solution was stirred for 2 hours and work-up, the residue was purified by Isco Combi-Flash Companion column chromatography (10-50% EtOAc in n-hexane) to give N-[4-bromo-2-(trifluoromethyl)phenyl]-2',4'-dimethyl-4,5'-bi-1,3-thiazol-2-amine (104 mg, 81%) as a yellow solid.

$^1$H NMR (CDCl$_3$, 400 MHz) δ 8.20 (d, 1H), 7.74 (d, 1H), 7.68 (dd, 1H), 7.25 (br s, 1H), 6.68 (s, 1H), 2.67 (s, 3H), 2.60 (s, 3H); LC-MS (APCI) m/z: 434.0 [M+H]$^+$.

EXAMPLE 25

1-{4-[(2',4'-Dimethyl-4,5'-bi-1,3-thiazol-2-yl)amino]phenyl}ethanone

Compound 44

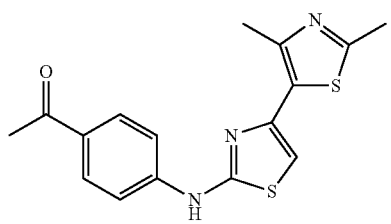

Following the procedure B, 2-bromo-1-(2,4-dimethyl-thiazol-5-yl)ethanone (78.1 mg, 0.402 mmol), ethanol (3.0 mL), and 1-(4-acetylphenyl)thiourea (94.1 mg, 0.402 mmol) were used to carry out the reaction. After the solution was stirred for overnight and work-up, the crude product was washed with ethyl acetate and CH$_2$Cl$_2$ to give N-(4-acetyl-phenyl)-2',4'-dimethyl-4,5'-bi-1,3-thiazol-2-amine (64.8 mg, 49%) as a yellow solid.

$^1$H NMR (DMSO-d$_6$, 400 MHz) δ 10.78 (s, 1H), 7.94 (d, 2H), 7.75 (d, 2H), 7.08 (s, 1H), 2.60 (s, 3H), 2.53 (s, 3H), 2.51 (s, 3H); LC-MS (APCI) m/z: 330.1 [M+H]$^+$.

EXAMPLE 26

N-(2,6-Diethylphenyl)-2',4'-dimethyl-4,5'-bi-1,3-thiazol-2-amine

Compound 45

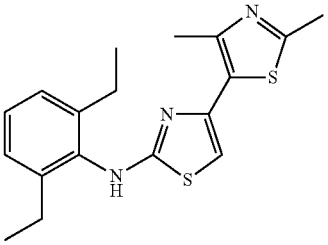

Step 1. 1-(2,6-Diethylphenyl)thiourea

Compound 46

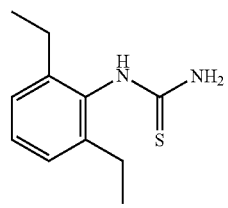

Following the procedure A, 2,6-diethylaniline (0.860 g, 5.76 mmol), 1.0 N HCl$_{(aq)}$ (7.0 mL), and ammonium thiocyanate (0.530 g, 6.94 mmol) were used to carry out the reaction. After the reaction was stirred for 20 h and work-up, 1-(2,6-diethylphenyl)thiourea (0.470 g, 39%) was afforded as a white solid.

$^1$H NMR (CDCl$_3$, 400 MHz) δ 7.52 (br s, 1H), 7.31 (t, 1H), 7.19 (d, 2H), 6.07 (br s, 1H), 5.34 (br s, 1H), 2.76-2.56 (m, 4H), 1.22 (t, 6H).

Step 2. N-(2,6-Diethylphenyl)-2',4'-dimethyl-4,5'-bi-1,3-thiazol-2-amine

Following the procedure B, 2-bromo-1-(2,4-dimethyl-thiazol-5-yl)ethanone (106 mg, 0.453 mmol), ethanol (3.0 mL), and 1-(2,6-diethylphenyl)thiourea (94.3 mg, 0.453 mmol) were used to carry out the reaction. After the solution was stirred for 3 h and work-up, the residue was purified by Isco Combi-Flash Companion column chromatography (10-50% EtOAc in n-hexane) to give N-(2,6-diethylphenyl)-2',4'-dimethyl-4,5'-bi-1,3-thiazol-2-amine (125 mg, 80%) as a yellow solid.

$^1$H NMR (CDCl$_3$, 400 MHz) δ 7.31 (dd, 1H), 7.20 (d, 2H), 6.77 (br s, 1H), 6.41 (s, 1H), 2.68 (q, 4H), 2.65 (s, 3H), 2.55 (s, 3H), 1.20 (t, 6H); LC-MS (APCI) m/z: 344.1 [M+H]$^+$.

EXAMPLE 27

N-(2-Ethyl-6-methylphenyl)-2',4'-dimethyl-4,5'-bi-1,3-thiazol-2-amine

Compound 47

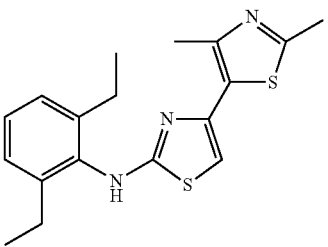

Step 1. 1-(2-Ethyl-6-methylphenyl)thiourea

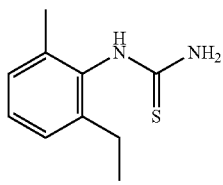

Compound 48

Following the procedure A, 2-ethyl-6-methylaniline (0.860 g, 5.76 mmol), 1.0 N HCl$_{(aq)}$ (7.0 mL), and ammonium thiocyanate (0.530 g, 6.94 mmol) were used to carry out the reaction. After the reaction was stirred for 20 h and work-up, 1-(2-ethyl-6-methyl-phenyl)thiourea (0.470 g, 39%) was afforded as a white solid.

$^1$H NMR (CDCl$_3$, 400 MHz) δ 7.78 (br s, 1H), 7.27-7.23 (m overlapped with s at 7.26, 1H), 7.18-7.14 (m, 2H), 6.40-6.10 (br s, 1H), 5.45-5.20 (br s, 1H), 2.68-2.60 (m, 2H), 2.31 (s, 3H), 1.21 (t, 3H).

Step 2. N-(2-Ethyl-6-methylphenyl)-2',4'-dimethyl-4,5'-bi-1,3-thiazol-2-amine

Following the procedure B, 2-bromo-1-(2,4-dimethylthiazol-5-yl)ethanone (109 mg, 0.466 mmol), ethanol (3.0 mL), and 1-(2-ethyl-6-methylphenyl)thiourea (90.6 mg, 0.466 mmol) were used to carry out the reaction. After the solution was stirred for 3 h and work-up, the residue was purified by Isco Combi-Flash Companion column chromatography (10-40% EtOAc in n-hexane) to give N-(2-ethyl-6-methylphenyl)-2',4'-dimethyl-4,5'-bi-1,3-thiazol-2-amine (92.6 mg, 60%) as a yellow solid.

$^1$H NMR (CDCl$_3$, 400 MHz) δ 7.25-7.16 (m, 3H), 6.82 (br s, 1H), 6.41 (s, 1H), 2.68 (q, 2H), 2.64 (s, 3H), 2.55 (s, 3H), 2.32 (s, 3H), 1.19 (t, 3H); LC-MS (APCI) m/z: 330.1 [M+H]$^+$.

EXAMPLE 28

N-(4-Bromo-2-ethylphenyl)-2',4'-dimethyl-4,5'-bi-1,3-thiazol-2-amine

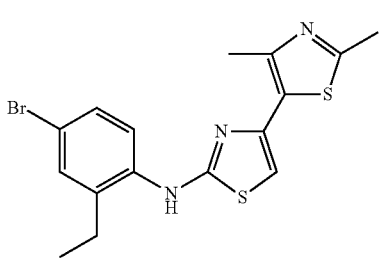

Compound 49

Step 1. 1-(4-Bromo-2-ethylphenyl)thiourea

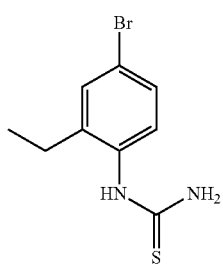

Compound 50

Following the procedure A, 4-bromo-2-ethylaniline (0.840 g, 4.20 mmol), 1.0 N HCl$_{(aq)}$ (5.0 mL), and ammonium thiocyanate (0.380 g, 4.99 mmol) were used to carry out the reaction. After the reaction was stirred for 20 h and work-up, 1-(4-bromo-2-ethylphenyl) thiourea (0.130 g, 12%) was afforded as a white solid.

$^1$H NMR (CDCl$_3$, 300 MHz) δ 7.54 (br s, 1H), 7.49 (d, 1H), 7.42 (dd, 1H), 7.12 (d, 1H), 6.10-5.60 (br s, 2H), 2.64 (q, 2H), 1.22 (t, 3H).

Step 2. N-(4-Bromo-2-ethylphenyl)-2',4'-dimethyl-4,5'-bi-1,3-thiazol-2-amine

Following the procedure B, 2-bromo-1-(2,4-dimethylthiazol-5-yl)ethanone (72.4 mg, 0.309 mmol), ethanol (3.0 mL), and 1-(4-bromo-2-ethylphenyl) thiourea (80.1 mg, 0.309 mmol) were used to carry out the reaction. After the solution was stirred for 2 h and work-up, the residue was purified by Isco Combi-Flash Companion column chromatography (10-40% EtOAc in n-hexane) to give N-(4-bromo-2-ethylphenyl)-2',4'-dimethyl-4,5'-bi-1,3-thiazol-2-amine (99.8 mg, 82%) as a brown gum.

$^1$H NMR (CDCl$_3$, 400 MHz) δ 7.57 (d, 1H), 7.42-7.36 (m, 2H), 6.93 (br s, 1H), 6.55 (s, 1H), 2.66 (s overlapped with q at 2.64, 3H), 2.64 (q overlapped with s at 2.66, 2H), 2.58 (s, 3H), 1.25 (t, 3H); LC-MS (APCI) m/z: 394.1 [M+H]$^+$.

EXAMPLE 29

N-(4-Chloro-2,6-dimethylphenyl)-2',4'-dimethyl-4,5'-bi-1,3-thiazol-2-amine

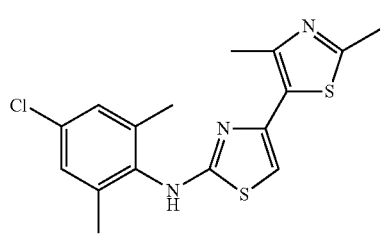

Compound 51

Step 1. 1-(4-Chloro-2,6-dimethylphenyl)thiourea

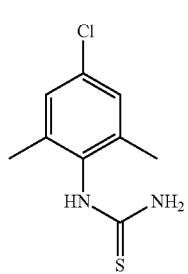

Compound 52

Following the procedure A, 4-chloro-2,6-dimethylaniline (0.810 g, 5.20 mmol), 1.0 N HCl$_{(aq)}$ (5.0 mL), and ammonium thiocyanate (0.480 g, 6.31 mmol) were used to carry out the reaction. After the reaction was stirred for 20 h and work-up, 1-(4-chloro-2,6-dimethylphenyl)thiourea (0.717 g, 64%) was afforded as a white solid.

$^1$H NMR (CDCl$_3$, 400 MHz) δ 7.43 (br s, 1H), 7.15 (s, 2H), 6.20-5.90 (br s, 1H), 5.50-5.10 (br s, 1H), 2.28 (s, 6H).

Step 2. N-(4-Chloro-2,6-dimethylphenyl)-2',4'-dimethyl-4,5'-bi-1,3-thiazol-2-amine Following the procedure B, 2-bromo-1-(2,4-dimethylthiazol-5-yl)ethanone (98.8 mg, 0.422 mmol), ethanol (3.0 mL), and 1-(4-chloro-2,6-dimethylphenyl)thiourea (90.6 mg, 0.422 mmol) were used to carry out the reaction. After the solution was stirred for 3 h and work-up, the residue was purified by Isco Combi-Flash Companion column chromatography (10-40% EtOAc in n-hexane) to give N-(4-chloro-2,6-dimethylphenyl)-2',4'-dimethyl-4,5'-bi-1,3-thiazol-2-amine (111 mg, 75%) as a yellow solid.

$^1$H NMR (CDCl$_3$, 400 MHz) δ 7.15 (s, 2H), 6.85-6.70 (m, 1H), 6.44 (s, 1H), 2.64 (s, 3H), 2.55 (s, 3H), 2.29 (s, 6H); LC-MS (ESI) m/z: 350.0 [M+H]$^+$.

EXAMPLE 30

N-(2,3-Dimethylphenyl)-2',4'-dimethyl-4,5'-bi-1,3-thiazol-2-amine

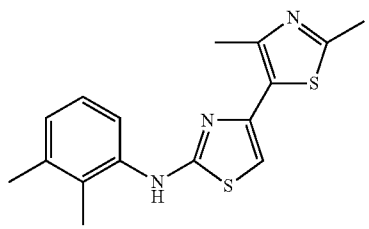

Compound 53

Step 1. 1-(2,3-Dimethylphenyl)thiourea

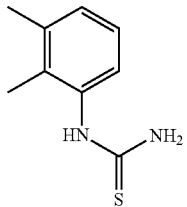

Compound 54

Following the procedure A, 2,3-dimethylaniline (0.700 g, 5.78 mmol), 1.0 N HCl$_{(aq)}$ (7.0 mL), and ammonium thiocyanate (0.530 g, 6.96 mmol) were used to carry out the reaction. After the reaction was stirred for 20 h and work-up, 1-(2,3-dimethylphenyl)thiourea (0.438 g, 42%) was afforded as a white solid.

$^1$H NMR (CDCl$_3$, 400 MHz) δ 7.65 (br s, 1H), 7.22-7.14 (m, 2H), 7.08 (d, 1H), 2.32 (s, 3H), 2.22 (s, 3H).

Step 2. N-(2,3-Dimethylphenyl)-2',4'-dimethyl-4,5'-bi-1,3-thiazol-2-amine

Following the procedure B, 2-bromo-1-(2,4-dimethylthiazol-5-yl)ethanone (104 mg, 0.446 mmol), ethanol (3.0 mL), and 1-(2,3-dimethylphenyl)thiourea (80.4 mg, 0.446 mmol) were used to carry out the reaction. After the solution was stirred for 1 h and work-up, the residue was purified by Isco Combi-Flash Companion column chromatography (0-40% EtOAc in n-hexane) to give N-(2,3-dimethylphenyl)-2',4'-dimethyl-4,5'-bi-1,3-thiazol-2-amine (118 mg, 83%) as a yellow solid.

$^1$H NMR (CDCl$_3$, 400 MHz) δ 7.40 (d, 1H), 7.15 (dd, 1H), 7.05 (d, 1H), 6.94 (br s, 1H), 6.51 (s, 1H), 2.67 (s, 3H), 2.58 (s, 3H), 2.34 (s, 3H), 2.24 (s, 3H); LC-MS (ESI) m/z: 316.0 [M+H]$^+$.

EXAMPLE 31

N-(4-Fluoro-2,6-dimethylphenyl)-2',4'-dimethyl-4,5'-bi-1,3-thiazol-2-amine

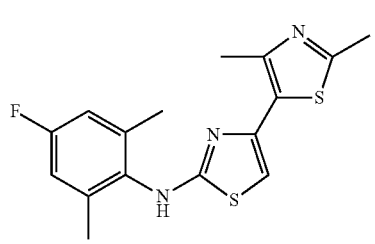

Compound 55

Step 1. 1-(4-Fluoro-2,6-dimethylphenyl)thiourea

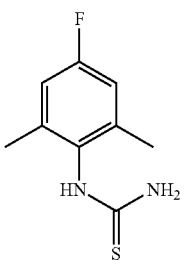

Compound 56

Following the procedure A, 4-fluoro-2,6-dimethylaniline (0.620 g, 4.45 mmol), 1.0 N HCl$_{(aq)}$ (5.0 mL), and ammonium thiocyanate (0.410 g, 5.39 mmol) were used to carry out the reaction. After the reaction was stirred for 20 h and work-up, 1-(4-fluoro-2,6-dimethylphenyl)thiourea (0.220 g, 25%) was afforded as a white solid.

$^1$H NMR (CDCl$_3$, 400 MHz) δ 7.40 (br s, 1H), 6.86 (d, 2H), 6.20-5.80 (br s, 1H), 5.50-5.10 (br s, 1H), 2.30 (s, 6H).

Step 2. N-(4-Fluoro-2,6-dimethylphenyl)-2',4'-dimethyl-4,5'-bi-1,3-thiazol-2-amine Following the procedure B, 2-bromo-1-(2,4-dimethylthiazol-5-yl)ethanone (99.1 mg, 0.423 mmol), ethanol (3.0 mL), and 1-(4-fluoro-2,6-dimethylphenyl)thiourea (83.9 mg, 0.423 mmol) were used to carry out the reaction. After the solution was stirred for 4 h and work-up, the residue was purified by Isco Combi-Flash Companion column chromatography (0-40% EtOAc in n-hexane) to give N-(4-fluoro-2,6-dimethylphenyl)-2',4'-dimethyl-4,5'-bi-1,3-thiazol-2-amine (119 mg, 84%) as a yellow solid.

$^1$H NMR (CDCl$_3$, 400 MHz) δ 6.86 (d, 2H), 6.75 (br s, 1H), 6.43 (s, 1H), 2.64 (s, 3H), 2.55 (s, 3H), 2.31 (s, 6H); LC-MS (ESI) m/z: 334.0 [M+H]$^+$.

EXAMPLE 32

4-[(2',4'-Dimethyl-4,5'-bi-1,3-thiazol-2-yl)amino]-3-methylbenzoic acid

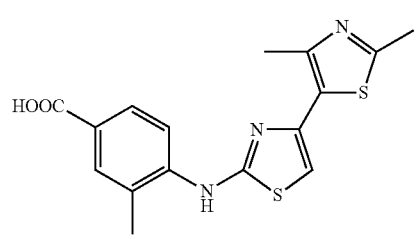

Compound 57

Step 1. 4-[(Benzoylcarbamothioyl)amino]-3-methylbenzoic acid

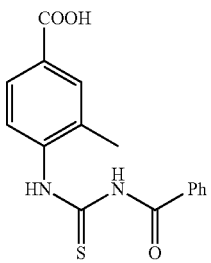

Compound 58

Following the procedure C, 4-amino-3-methylbenzoic acid (0.690 g, 4.56 mmol), benzoyl isothiocyante (0.680 mL, 5.06 mmol), and acetone (10 mL) were used to carry out the reaction. After the reaction was stirred for 40 min and work-up, 4-[(benzoylcarbamothioyl)amino]-3-methylbenzoic acid (1.43 g, 100%) was afforded as a white solid.

$^1$H NMR (DMSO-$d_6$, 300 MHz) δ 12.45 (s, 1H), 11.71 (s, 1H), 7.98 (d, 2H), 7.92-7.78 (m, 3H), 7.66 (dd, 1H), 7.53 (dd, 2H), 2.32 (s, 3H).

Step 2. 4-(Carbamothioylamino)-3-methylbenzoic acid

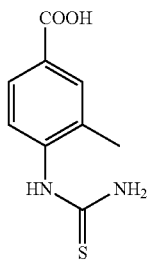

Compound 59

A solution of 4-[(benzoylcarbamothioyl)amino]-3-methylbenzoic acid (0.570 g, 1.81 mmol) and NaOMe (0.294 g, 5.44 mmol) in methanol (20 mL) was stirred at room temperature for 3 h. The solution was concentrated. The residue was treated with saturated NH$_4$Cl$_{(aq)}$ and extracted with CH$_2$Cl$_2$. The combined organic layers were dried over MgSO$_{4(s)}$, filtered, and concentrated. The crude product was washed with ethyl acetate/n-hexane to give 4-(carbamothioylamino)-3-methylbenzoic acid (0.145 g, 38%) as a lightly yellow solid.

$^1$H NMR (DMSO-$d_6$, 300 MHz) δ 13.00-12.70 (br s, 1H), 9.31 (s, 1H), 7.80 (s, 1H), 7.73 (d, 1H), 7.47 (d, 1H), 2.23 (s, 3H).

Step 3. 4-[(2',4'-Dimethyl-4,5'-bi-1,3-thiazol-2-yl)amino]-3-methylbenzoic acid

Following the procedure B, 2-bromo-1-(2,4-dimethylthiazol-5-yl)ethanone (90.0 mg, 0.384 mmol), ethanol (3.0 mL), and 4-(carbamothioylamino)-3-methylbenzoic acid (80.8 mg, 0.384 mmol) were used to carry out the reaction. After the solution was stirred for overnight and work-up, the crude product was washed with n-hexane/diethyl ether to give 4-[(2',4'-dimethyl-4,5'-bi-1,3-thiazol-2-yl)amino]-3-methylbenzoic acid (43.7 mg, 33%) as a solid.

$^1$H NMR (DMSO-$d_6$, 400 MHz) δ 9.62 (s, 1H), 8.31 (d, 1H), 7.78-7.74 (m, 2H), 7.03 (s, 1H), 2.58 (s, 3H), 2.50 (s overlapped with m at 2.55-2.47, 3H), 2.33 (s, 3H); LC-MS (ESI) m/z: 346.0 [M+H]$^+$.

EXAMPLE 33

4-[(2',4'-Dimethyl-4,5'-bi-1,3-thiazol-2-yl)amino]-3-methylphenol

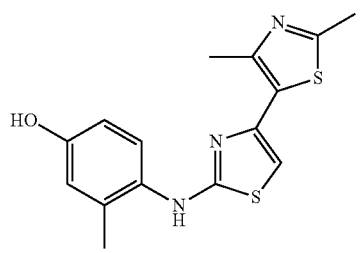

Compound 60

Step 1. 1-(4-Hydroxy-2-methylphenyl)thiourea

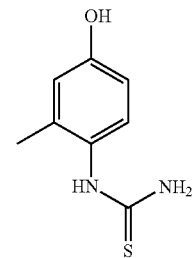

Compound 61

Following the procedure A, 4-amino-m-cresol (0.560 g, 4.55 mmol), 1.0 N HCl$_{(aq)}$ (6.0 mL), and ammonium thiocyanate (0.420 g, 5.52 mmol) were used to carry out the reaction. After the reaction was stirred for 17 h and work-up, 1-(4-hydroxy-2-methylphenyl)thiourea (0.230 g, 28%) was afforded as a lightly brown solid.

$^1$H NMR (DMSO-$d_6$, 400 MHz) δ 9.36 (br s, 1H), 8.99 (br s, 1H), 7.70-7.30 (br s, 1H), 6.88 (d, 1H), 6.61 (d, 1H), 6.55 (dd, 1H), 2.06 (s, 3H).

Step 2. 4-[(2',4'-Dimethyl-4,5'-bi-1,3-thiazol-2-yl)amino]-3-methylphenol

Following the procedure B, 2-bromo-1-(2,4-dimethylthiazol-5-yl)ethanone (113 mg, 0.484 mmol), ethanol (3.0 mL), and 1-(4-hydroxy-2-methylphenyl)thiourea (80.2 mg, 0.440 mmol) were used to carry out the reaction. After the solution was stirred for 3 h and work-up, the residue was purified by Isco Combi-Flash Companion column chromatography (0-10% MeOH in CH$_2$Cl$_2$) to give 4-[(2',4'-dimethyl-4,5'-bi-1,3-thiazol-2-yl)amino]-3-methylphenol (86.5 mg, 62%) as a brown solid. 1H NMR (DMSO-$d_6$, 300 MHz) δ 9.33 (s, 1H), 9.21 (s, 1H), 7.25 (d, 1H), 6.72 (s, 1H), 6.65 (d, 1H), 6.59 (dd, 1H), 2.55 (s, 3H), 2.45 (s, 3H), 2.14 (s, 3H); LC-MS (ESI) m/z: 318.0 [M+H]$^+$.

EXAMPLE 34

{2-[(2',4'-Dimethyl-4,5'-bi-1,3-thiazol-2-yl)amino]phenyl}methanol

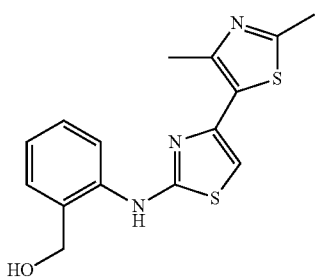

Compound 62

Step 1. N-{[2-(Hydroxymethyl)phenyl]carbamothioyl}benzamide

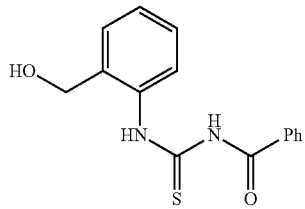

Compound 63

Following the procedure C, 2-aminobenzyl alcohol (0.720 g, 5.85 mmol), benzoyl isothiocyante (0.860 mL, 6.40 mmol), and acetone (12 mL) were used to carry out the reaction. After the reaction was stirred for 40 min and work-up, N-{[2-(hydroxymethyl)-phenyl]carbamothioyl}benzamide (1.73 g, 100%) was afforded as a gray solid.

$^1$H NMR (CDCl$_3$, 400 MHz) δ 12.38 (br s, 1H), 9.22 (br s, 1H), 7.92 (d, 2H), 7.76 (d, 1H), 7.73-7.34 (m, 6H), 4.73 (s, 2H), 2.17 (br s, 1H).

Step 2. 1-[2-(Hydroxymethyl)phenyl]thiourea

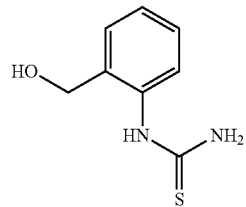

Compound 64

A solution of N-{[2-(hydroxymethyl)phenyl]carbamothioyl}benzamide (1.02 g, 3.56 mmol) in 5% NaOH$_{(aq)}$ (9.0 mL) was stirred at 70° C. for 1.5 h. After the solution was poured into cooled 5% HCl$_{(aq)}$, benzoic acid was removed by filtration. The filtrate was neutralized with saturated NaHCO$_{3(aq)}$ and extracted with CH$_2$Cl$_2$. The combined organic layers were dried over MgSO$_{4(s)}$, filtered, and concentrated to give 1-[2-(hydroxymethyl)-phenyl]thiourea (0.151 g, 23%) as a solid.

$^1$H NMR (DMSO-d$_6$, 300 MHz) δ 9.11 (br s, 1H), 7.43 (dd, 1H), 7.30-7.19 (m, 3H), 5.20 (t, 1H), 4.43 (d, 2H).

Step 3. {2-[(2',4'-Dimethyl-4,5'-bi-1,3-thiazol-2-yl)amino]phenyl}methanol

Following the procedure B, 2-bromo-1-(2,4-dimethyl-thiazol-5-yl)ethanone (108 mg, 0.461 mmol), ethanol (3.0 mL), and 1-[2-(hydroxymethyl)phenyl]thiourea (76.4 mg, 0.461 mmol) were used to carry out the reaction. After the solution was stirred for 3 h and work-up, the crude product was washed with n-hexane/diethyl ether to give {2-[(2',4'-dimethyl-4,5'-bi-1,3-thiazol-2-yl)amino]phenyl}methanol (24.2 mg, 18%) as a green solid.

$^1$H NMR (DMSO-d$_6$, 300 MHz) δ 9.40 (br s, 1H), 7.87 (d, 1H), 7.43 (d, 1H), 7.27 (dd, 1H), 7.10 (dd, 1H), 6.92 (s, 1H), 4.57 (s, 2H), 2.59 (s, 3H); LC-MS (ESI) m/z: 340.0 [M+Na]$^+$.

EXAMPLE 35

2-[(2',4'-Dimethyl-4,5'-bi-1,3-thiazol-2-yl)amino]phenol

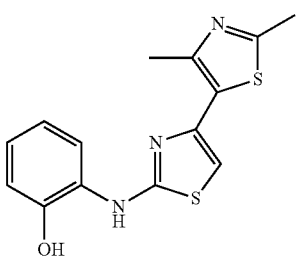

Compound 65

Step 1. N-[(2-hydroxyphenyl)carbamothioyl]benzamide

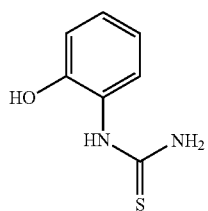

Compound 66

Following the procedure C, 2-aminophenol (0.680 g, 6.23 mmol), benzoyl isothiocyante (0.880 mL, 6.55 mmol), and acetone (12 mL) were used to carry out the reaction. After the reaction was stirred for 30 min and work-up, N-[(2-hydroxyphenyl)carbamothioyl]-benzamide (1.60 g, 95%) was afforded as a solid.

$^1$H NMR (CDCl$_3$, 400 MHz) δ 12.62 (br s, 1H), 9.18 (br s, 1H), 7.91 (d, 2H), 7.69 (t, 1H), 7.57 (dd, 2H), 7.42 (d, 1H), 7.30 (dd, 1H), 7.11 (d, 1H), 7.04 (dd, 1H), 6.44 (br s, 1H).

Step 2. 1-(2-hydroxyphenyl)thiourea

Compound 67

A solution of N-[(2-hydroxyphenyl)carbamothioyl]benzamide (0.90 g, 3.30 mmol) in 5% NaOH$_{(aq)}$ (9.0 mL) was stirred at 70° C. for 3 h. After the solution was diluted with saturated NH$_4$Cl$_{(aq)}$ and extracted with ethyl acetate. The combined organic layers were washed with saturated NaHCO$_{3(aq)}$, dried over MgSO$_{4(s)}$, filtered, and concentrated to give 1-(2-hydroxyphenyl)thiourea (0.316 g, 57%) as a solid.

$^1$H NMR (DMSO-d$_6$, 300 MHz) δ 9.74 (br s, 1H), 8.97 (br s, 1H), 7.82-7.70 (m, 1H), 6.96 (dd, 1H), 6.85 (d, 1H), 6.74 (dd, 1H).

Step 3. 2-[(2',4'-Dimethyl-4,5'-bi-1,3-thiazol-2-yl)amino]phenol

Following the procedure B, 2-bromo-1-(2,4-dimethylthiazol-5-yl)ethanone (113 mg, 0.485 mmol), ethanol (3.0 mL), and 1-(2-hydroxyphenyl)thiourea (74.1 mg, 0.440 mmol) were used to carry out the reaction. After the solution was stirred for 3 h and work-up, the residue was purified by Isco Combi-Flash Companion column chromatography (0-60% EtOAc in n-hexane) to give 2-[(2',4'-dimethyl-4,5'-bi-1,3-thiazol-2-yl)amino]phenol (106 mg, 79%) as a white solid.

$^1$H NMR (MeOD-d$_4$, 400 MHz) δ 7.95 (dd, 1H), 6.95-6.82 (m, 3H), 6.79 (s, 1H), 2.65 (s, 3H), 2.56 (s, 3H); LC-MS (ESI) m/z: 304.0 [M+H]$^+$.

EXAMPLE 36

2',4'-Dimethyl-N-[2-(1-piperidinyl)phenyl]-4,5'-bi-1,3-thiazol-2-amine

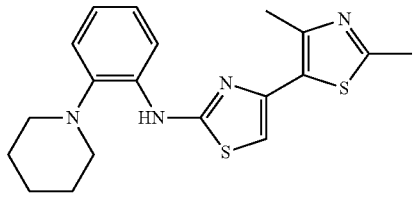

Compound 68

Step 1. 1-[2-(1-piperidinyl)phenyl]thiourea

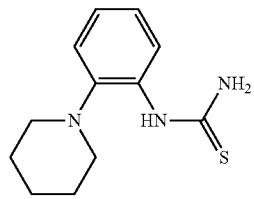

Compound 69

Following the procedure A, 2-(1-piperidinyl)aniline (0.700 g, 3.97 mmol), 1.0 N HCl$_{(aq)}$ (9.6 mL), and ammonium thiocyanate (0.360 g, 4.77 mmol) were used to carry out the reaction. After the reaction was stirred for 20 h and work-up, 1-[2-(1-piperidinyl)phenyl]-thiourea (0.410 g, 44%) was afforded as a white solid.

$^1$H NMR (CDCl$_3$, 400 MHz) δ 7.98 (br s, 1H), 7.25-7.18 (m, 2H), 7.11-7.05 (m, 2H), 6.58 (br s, 2H), 2.89-2.86 (m, 4H), 1.79-1.73 (m, 4H), 1.62-1.57 (m, 2H).

Step 2. 2',4'-Dimethyl-N-[2-(1-piperidinyl)phenyl]-4,5'-bi-1,3-thiazol-2-amine

Following the procedure B, 2-bromo-1-(2,4-dimethylthiazol-5-yl)ethanone (90.5 mg, 0.389 mmol), ethanol (6.0 mL), and 1-[2-(1-piperidinyl)phenyl]thiourea (82.7 mg, 0.351 mmol) were used to carry out the reaction. After the solution was stirred for 4 h and work-up, the residue was purified by Isco Combi-Flash Companion column chromatography (15-50% EtOAc in n-hexane) to give 2',4'-dimethyl-N-[2-(1-piperidinyl)phenyl]-4,5'-bi-1,3-thiazol-2-amine (128 mg, 91%) as a brown solid.

$^1$H NMR (CDCl$_3$, 400 MHz) δ 8.49 (br s, 1H), 8.04 (d, 1H), 7.22-7.16 (m, 2H), 7.00 (dd, 1H), 6.60 (s, 1H), 2.90-2.80 (m, 4H), 2.68 (s, 3H), 2.62 (s, 3H), 1.83-1.56 (m, 6H); LC-MS (ESI) m/z: 371.1 [M+H]$^+$.

EXAMPLE 37

2',4'-Dimethyl-N-[2-(4-morpholinyl)phenyl]-4,5'-bi-1,3-thiazol-2-amine

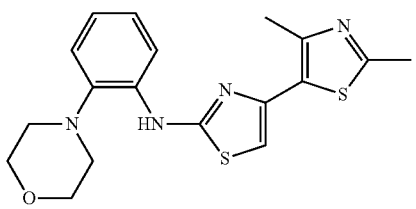

Compound 70

Step 1. 1-[2-(4-Morpholinyl)phenyl)]thiourea

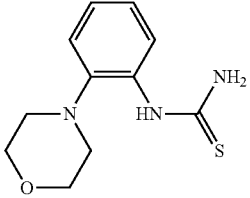

Compound 71

Following the procedure A, 2-(4-morpholinyl)aniline (0.880 g, 4.94 mmol), 1.0 N HCl$_{(aq)}$ (12 mL), and ammonium thiocyanate (0.450 g, 5.92 mmol) were used to carry out the reaction. After the reaction was stirred for 20 h and work-up, 1-[2-(4-morpholinyl)phenyl)]thiourea (0.100 g, 9%) was afforded as a solid.

$^1$H NMR (DMSO-d$_6$, 400 MHz) δ 8.84 (br s, 1H), 7.65 (d, 1H), 7.15-6.99 (m, 3H), 3.76-3.74 (m, 4H), 2.82-2.80 (m, 4H).

Step 2. 2',4'-Dimethyl-N-[2-(4-morpholinyl)phenyl]-4,5'-bi-1,3-thiazol-2-amine

Following the procedure B, 2-bromo-1-(2,4-dimethylthiazol-5-yl)ethanone (98.5 mg, 0.421 mmol), ethanol (6.0 mL), and 1-[2-(4-morpholinyl)phenyl)]thiourea (90.8 mg, 0.383 mmol) were used to carry out the reaction. After the solution was stirred for 3 h and work-up, the residue was purified by Isco Combi-Flash Companion column chromatography (10-50% EtOAc in n-hexane) to give 2',4'-dimethyl-N-[2-(4-morpholinyl)phenyl)]-4,5'-bi-1,3-thiazol-2-amine (114 mg, 80%) as an orange solid.

$^1$H NMR (CDCl$_3$, 400 MHz) δ 8.41 (br s, 1H), 8.04 (d, 1H), 7.24-7.20 (m, 2H), 7.04 (dd, 1H), 6.62 (s, 1H), 3.92-3.90 (m, 4H), 2.92-2.90 (m, 4H), 2.68 (s, 3H), 2.62 (s, 3H); LC-MS (ESI) m/z: 373.1 [M+H]$^+$.

EXAMPLE 38

2',4'-Dimethyl-N-[2-(1H-pyrrol-1-yl)phenyl]-4,5'-bi-1,3-thiazol-2-amine

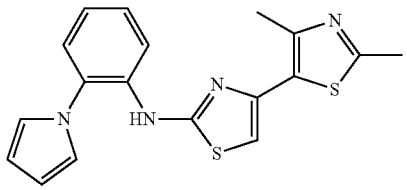

Compound 72

Step 1. N-{[2-(1H-Pyrrol-1-yl)phenyl]carbamothioyl}benzamide

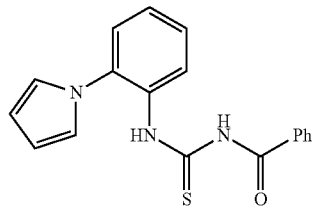

Compound 73

Following the procedure C, 1-(2-aminophenyl)pyrrole (0.510 g, 3.22 mmol), benzoyl isothiocyante (0.450 mL, 3.42 mmol), and acetone (6.0 mL) were used to carry out the reaction. After the reaction was stirred for 40 min and work-up, N-{[2-(1H-pyrrol-1-yl)phenyl]-carbamothioyl}benzamide (1.05 g, 102%) was afforded as an orange solid.

$^1$H NMR (DMSO-d$_6$, 300 MHz) δ 12.15 (br s, 1H), 11.66 (br s, 1H), 7.92 (d, 2H), 7.68-7.60 (m, 2H), 7.51 (dd, 2H), 7.50-7.40 (m, 3H), 7.03-6.99 (m, 2H), 6.21-6.17 (m, 2H).

Step 2. 1-[2-(1H-Pyrrol-1-yl)phenyl]thiourea

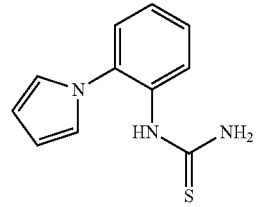

Compound 74

A solution of N-{[2-(1H-pyrrol-1-yl)phenyl]carbamothioyl}benzamide (0.830 g, 2.58 mmol) in 5% NaOH$_{(aq)}$ (10 mL) was stirred at 70° C. for 3 h. After the solution was cooled to room temperature, the reaction was quenched with 5% HCl$_{(aq)}$ and then extracted with CH$_2$Cl$_2$. The combined organic layers were washed with saturated NaHCO$_{3(aq)}$, dried over MgSO$_{4(s)}$, filtered, and concentrated to give 1-[2-(1H-pyrrol-1-yl)phenyl]thiourea. (0.502 g, 90%) as a yellow solid.

$^1$H NMR (DMSO-d$_6$, 400 MHz) δ 9.13 (br s, 1H), 7.43-7.31 (m, 4H), 7.01-6.98 (m, 2H), 6.24-6.20 (m, 2H).

Step 3. 2',4'-Dimethyl-N-[2-(1H-pyrrol-1-yl)phenyl]-4,5'-bi-1,3-thiazol-2-amine

Following the procedure B, 2-bromo-1-(2,4-dimethyl-thiazol-5-yl)ethanone (108 mg, 0.462 mmol), ethanol (3.0 mL), and 1-[2-(1H-pyrrol-1-yl)phenyl]thiourea (91.3 mg, 0.420 mmol) were used to carry out the reaction. After the solution was stirred for 3 h and work-up, the residue was purified by Isco Combi-Flash Companion column chromatography (5-40% EtOAc in n-hexane) to give 2',4'-dimethyl-N-[2-(1H-pyrrol-1-yl)phenyl]-4,5'-bi-1,3-thiazol-2-amine (87.7 mg, 59%) as a white solid.

$^1$H NMR (CDCl$_3$, 300 MHz) δ 8.26 (d, 1H), 7.43 (dd, 1H), 7.29 (d, 1H), 7.11 (dd, 1H), 6.99 (br s, 1H), 6.84-6.80 (m, 2H), 6.61 (s, 1H), 6.43-6.39 (m, 2H), 2.67 (s, 3H), 2.59 (s, 3H); LC-MS (ESI) m/z: 353.1 [M+H]$^+$.

EXAMPLE 39

$N^1$-(2',4'-Dimethyl-4,5'-bi-1,3-thiazol-2-yl)-$N^4$,$N^4$,2-trimethyl-1,4-benzenediamine

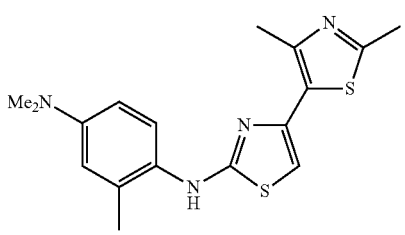

Compound 75

Step 1. 1-[4-(Dimethylamino)-2-methylphenyl]thiourea

Compound 76

Following the procedure A, 4-dimethylamino-2-methylaniline (0.570 g, 3.79 mmol), 1.0 N HCl$_{(aq)}$ (10 mL), and ammonium thiocyanate (0.350 g, 4.55 mmol) were used to carry out the reaction. After the reaction was stirred for 18 h and work-up, 1-[4-(dimethylamino)-2-methylphenyl]thiourea (0.139 g, 18%) was afforded as a gray solid.

$^1$H NMR (DMSO-d$_6$, 400 MHz) δ 8.98 (br s, 1H), 6.89 (d, 1H), 6.58 (d, 1H), 6.53 (dd, 1H), 2.86 (s, 6H), 2.10 (s, 3H).

Step 2. $N^1$-(2',4'-Dimethyl-4,5'-bi-1,3-thiazol-2-yl)-$N^4$,$N^4$,2-trimethyl-1,4-benzenediamine Following the procedure B, 2-bromo-1-(2,4-dimethyl-thiazol-5-yl)ethanone (101 mg, 0.430 mmol), ethanol (3.0 mL), and 1-[4-(dimethylamino)-2-methylphenyl]thiourea (81.8 mg, 0.391 mmol) were used to carry out the reaction. After the solution was stirred for overnight and work-up, the residue was purified by Isco Combi-Flash Companion column chromatography (5-70% EtOAc in n-hexane) to give $N^1$-(2',4'-dimethyl-4,5'-bi-1,3-thiazol-2-yl)-$N^4$,$N^4$,2-trimethyl-1,4-benzenediamine (32.9 mg, 24%) as a green solid.

$^1$H NMR (DMSO-d$_6$, 400 MHz) δ 9.19 (br s, 1H), 7.24 (d, 1H), 6.69 (s, 1H), 6.62 (d, 1H), 6.57 (dd, 1H), 2.87 (s, 6H), 2.56 (s, 3H), 2.45 (s, 3H), 2.18 (s, 3H); LC-MS (ESI) m/z: 345.1 [M+H]$^+$.

EXAMPLE 40

N-(3-Chloro-2-methylphenyl)-2',4'-dimethyl-4,5'-bi-1,3-thiazol-2-amine

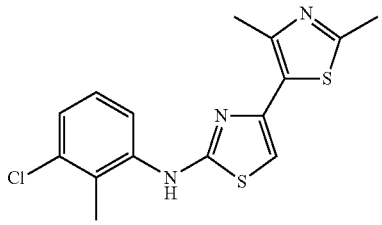

Compound 77

Step 1. 1-(3-Chloro-2-methylphenyl)thiourea

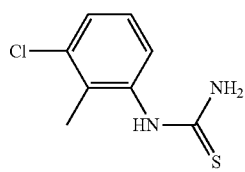

Compound 78

Following the procedure A, 3-chloro-2-methylaniline (1.00 mL, 8.40 mmol), 1.0 N HCl$_{(aq)}$ (10 mL), and ammonium thiocyanate (0.770 g, 10.1 mmol) were used to carry out the reaction. After the reaction was stirred for overnight and work-up, 1-(3-chloro-2-methylphenyl)thiourea (0.780 g, 46%) was afforded as a purple solid.

$^1$H NMR (CDCl$_3$, 400 MHz) δ 7.95 (br s, 1H), 7.41 (dd, 1H), 7.24-7.17 (m, 2H), 2.37 (s, 3H).

Step 2. N-(3-Chloro-2-methylphenyl)-2',4'-dimethyl-4,5'-bi-1,3-thiazol-2-amine

Following the procedure B, 2-bromo-1-(2,4-dimethyl-thiazol-5-yl)ethanone (106 mg, 0.452 mmol), ethanol (3.0 mL), and 1-(3-chloro-2-methylphenyl)thiourea (82.4 mg, 0.452 mmol) were used to carry out the reaction. After the solution was stirred for 3 h and work-up, the residue was purified by Isco Combi-Flash Companion column chromatography (5-40% EtOAc in n-hexane) to give N-(3-chloro-2-methylphenyl)-2',4'-dimethyl-4,5'-bi-1,3-thiazol-2-amine (115 mg, 83%) as a yellow solid.

$^1$H NMR (CDCl$_3$, 300 MHz) δ 7.57 (d, 1H), 7.26-7.18 (m, 2H), 7.10 (br s, 1H), 6.56 (s, 1H), 2.67 (s, 3H), 2.58 (s, 3H), 2.39 (s, 3H); LC-MS (ESI) m/z: 336.0 [M+H]$^+$.

EXAMPLE 41

2',4'-Dimethyl-N-(3-methyl-2-pyridinyl)-4,5'-bi-1,3-thiazol-2-amine

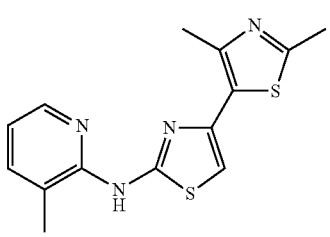

Compound 79

Step 1. N-[(3-Methyl-2-pyridinyl)carbamothioyl]benzamide

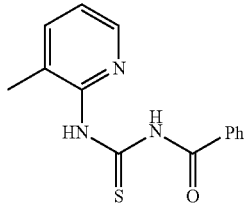

Compound 80

Following the procedure C, 2-methyl-3-picoline (0.600 mL, 5.95 mmol), benzoyl isothiocyante (0.880 mL, 6.55 mmol), and acetone (12 mL) were used to carry out the reaction. After the reaction was stirred for 40 min and work-up, N-[(3-methyl-2-pyridinyl)carbamothioyl]benzamide (1.24 g, 77%) was afforded as an orange solid.

$^1$H NMR (CDCl$_3$, 300 MHz) δ 9.22 (br s, 1H), 8.43 (br s, 1H), 7.91 (d, 2H), 7.75-7.52 (m, 5H), 2.41 (s, 3H).

Step 2. 1-(3-Methyl-2-pyridinyl)thiourea

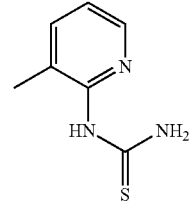

Compound 81

A solution of N-[(3-methyl-2-pyridinyl)carbamothioyl]benzamide (0.650 g, 2.40 mmol) in 5% NaOH$_{(aq)}$ (9.0 mL) was stirred at 70° C. for 1.5 h. After the solution was cooled to room temperature, it was quenched with 5% HCl$_{(aq)}$ and then extracted with CH$_2$Cl$_2$. The combined organic layers were washed with saturated NaHCO$_{3(aq)}$, dried over MgSO$_{4(s)}$, filtered, and concentrated to give 1-(3-methyl-2-pyridinyl)thiourea (0.330 g, 80%) as a yellow solid.

$^1$H NMR (CDCl$_3$, 400 MHz) δ 11.26 (br s, 1H), 8.08 (d, 1H), 7.97 (br s, 1H), 7.50 (d, 1H), 7.00 (br s, 1H), 6.94 (dd, 1H), 2.30 (s, 3H).

Step 3. 2',4'-Dimethyl-N-(3-methyl-2-pyridinyl)-4,5'-bi-1,3-thiazol-2-amine

Following the procedure B, 2-bromo-1-(2,4-dimethyl-thiazol-5-yl)ethanone (126 mg, 0.537 mmol), ethanol (3.0 mL), and 1-(3-methyl-2-pyridinyl)thiourea (81.6 mg, 0.488 mmol) were used to carry out the reaction. After the solution was stirred for 4 h and work-up, the crude product was washed with n-hexane/diethyl ether to give 2',4'-dimethyl-N-(3-methyl-2-pyridinyl)-4,5'-bi-1,3-thiazol-2-amine (125 mg, 84%) as a yellow solid.

$^1$H NMR (CDCl$_3$, 400 MHz) δ 8.24 (d, 1H), 8.04 (br s, 1H), 7.45 (d, 1H), 6.87 (dd, 1H), 6.80 (s, 1H), 2.68 (s, 3H), 2.60 (s, 3H), 2.33 (s, 3H); LC-MS (ESI) m/z: 303.0 [M+H]$^+$.

EXAMPLE 42

N-(3-Ethyl-6-methyl-2-pyridinyl)-2',4'-dimethyl-4,5'-bi-1,3-thiazol-2-amine

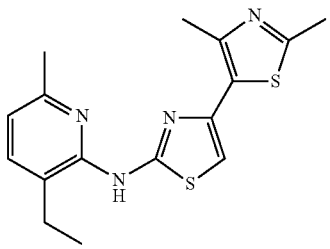

Compound 82

Step 1. N-[(3-Ethyl-6-methyl-2-pyridinyl)carbamothioyl]benzamide

Compound 83

Following the procedure C, 2-amino-3-ethyl-6-methyl-pyridine (0.520 g, 3.67 mmol), benzoyl isothiocyante (0.540 mL, 4.02 mmol), and acetone (6.0 mL) were used to carry out the reaction. After the reaction was stirred for 40 min and work-up, N-[(3-ethyl-6-methyl-2-pyridinyl)carbamothioyl]benzamide (0.890 g, 81%) was afforded as an orange solid.

$^1$H NMR (CDCl$_3$, 300 MHz) δ 9.25 (br s, 1H), 7.90 (d, 2H), 7.73-7.48 (m, 5H), 7.16 (d, 1H), 2.71 (q, 2H), 2.56 (s, 3H), 1.26 (t, 3H).

Step 2. 1-(3-Ethyl-6-methyl-2-pyridinyl)thiourea

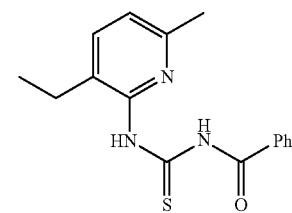

Compound 84

A solution of N-[(3-ethyl-6-methyl-2-pyridinyl)carbamothioyl]benzamide (0.560 g, 1.87 mmol) in 5% NaOH$_{(aq)}$ (8.0 mL) was stirred at 70° C. for 1.5 h. After the solution was cooled to room temperature, it was quenched with 5% HCl$_{(aq)}$ and then extracted with CH$_2$Cl$_2$. The combined organic layers were washed with saturated NaHCO$_{3(aq)}$, dried over MgSO$_{4(s)}$, filtered, and concentrated to give 1-(3-ethyl-6-methyl-2-pyridinyl)thiourea (0.180 g, 49%) as a white solid.

$^1$H NMR (CDCl$_3$, 300 MHz) δ 11.43 (br s, 1H), 8.00 (br s, 1H), 7.41 (d, 1H), 6.91 (br s, 1H), 6.82 (d, 1H), 2.58 (q, 2H), 2.44 (s, 3H), 1.27 (t, 3H).

Step 3. N-(3-Ethyl-6-methyl-2-pyridinyl)-2',4'-dimethyl-4,5'-bi-1,3-thiazol-2-amine Following the procedure B, 2-bromo-1-(2,4-dimethylthiazol-5-yl)ethanone (106 mg, 0.453 mmol), ethanol (3.0 mL), and 1-(3-ethyl-6-methyl-2-pyridinyl)thiourea (80.4 mg, 0.453 mmol) were used to carry out the reaction. After the solution was stirred for 4 h and work-up, the residue was purified by Isco Combi-Flash Companion column chromatography (5-50% EtOAc in n-hexane) to give N-(3-ethyl-6-methyl-2-pyridinyl)-2',4'-dimethyl-4,5'-bi-1,3-thiazol-2-amine (127 mg, 93%) as a yellow solid.

$^1$H NMR (CDCl$_3$, 400 MHz) δ 8.09 (br s, 1H), 7.35 (d, 1H), 6.78 (s, 1H), 6.74 (d, 1H), 2.68 (s, 3H), 2.60 (q overlapped with s at 2.59, 2H), 2.59 (s overlapped with q at 2.60, 3H), 2.54 (s, 3H), 1.30 (t, 3H); LC-MS (ESI) m/z: 331.1 [M+H]$^+$.

EXAMPLE 43

N-(3-Methoxy-2-methylphenyl)-2',4'-dimethyl-4,5'-bi-1,3-thiazol-2-amine

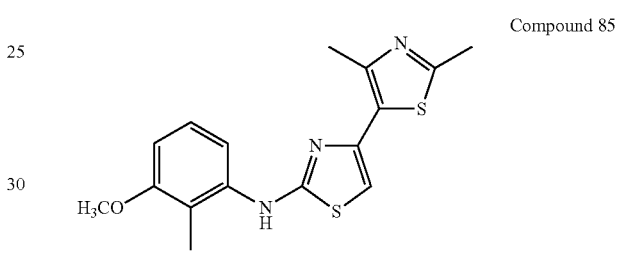

Compound 85

Step 1. 1-(3-Methoxy-2-methylphenyl)thiourea

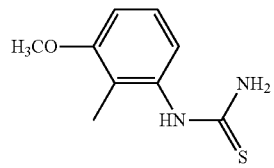

Compound 86

Following the procedure A, 3-methoxy-2-methylphenylaniline (0.320 g, 2.60 mmol), 1.0 N HCl$_{(aq)}$ (4.5 mL), and ammonium thiocyanate (0.240 g, 3.15 mmol) were used to carry out the reaction. After the reaction was stirred for 20 h and work-up, 1-(3-methoxy-2-methylphenyl)thiourea (0.133 g, 26%) was afforded as a purple solid.

$^1$H NMR (CDCl$_3$+MeOD, 400 MHz) δ 7.16 (dd, 1H), 6.81 (d, 1H), 6.78 (d, 1H), 3.81 (s, 3H), 2.08 (s, 3H).

Step 2. N-(3-Methoxy-2-methylphenyl)-2',4'-dimethyl-4,5'-bi-1,3-thiazol-2-amine Following the procedure B, 2-bromo-1-(2,4-dimethylthiazol-5-yl)ethanone (116 mg, 0.494 mmol), ethanol (3.0 mL), and 1-(3-methoxy-2-methylphenyl)-2-thiourea (80.8 mg, 0.412 mmol) were used to carry out the reaction. After the solution was stirred for 4 h and work-up, the residue was purified by Isco Combi-Flash Companion column chromatography (0-50% EtOAc in n-hexane) to give N-(3-methoxy-2-methylphenyl)-2',4'-dimethyl-4,5'-bi-1,3-thiazol-2-amine (105 mg, 77%) as a solid.

$^1$H NMR (CDCl$_3$, 300 MHz) δ 7.25-7.20 (m, 2H), 6.97 (br s, 1H), 6.73 (d, 1H), 6.53 (s, 1H), 3.85 (s, 3H), 2.66 (s, 3H), 2.58 (s, 3H), 2.19 (s, 3H); LC-MS (ESI) m/z: 332.1 [M+H]$^+$.

EXAMPLE 44

2',4'-Dimethyl-N-[2-methyl-3-(trifluoromethyl)phenyl]-4,5'-bi-1,3-thiazol-2-amine

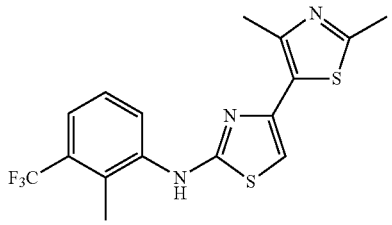

Compound 87

Step 1. 1-[2-Methyl-3-(trifluoromethyl)phenyl]thiourea

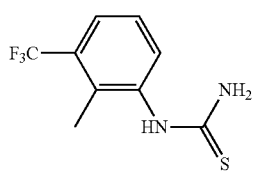

Compound 88

Following the procedure A, 2-methyl-3-(trifluoromethyl)aniline (0.310 g, 1.77 mmol), 1.0 N HCl$_{(aq)}$ (3.5 mL), and ammonium thiocyanate (0.160 g, 2.10 mmol) were used to carry out the reaction. After the reaction was stirred for 20 h and work-up, 1-[2-methyl-3-(trifluoromethyl)phenyl]thiourea (0.248 g, 60%) was afforded as a white solid.

$^1$H NMR (CDCl$_3$, 400 MHz) δ 7.90-7.70 (m, 1H), 7.69 (d, 1H), 7.47 (d, 1H), 7.40 (dd, 1H), 2.44 (s, 3H).

Step 2. 2',4'-Dimethyl-N-[2-methyl-3-(trifluoromethyl)phenyl]-4,5'-bi-1,3-thiazol-2-amine Following the procedure B, 2-bromo-1-(2,4-dimethylthiazol-5-yl)ethanone (99.8 mg, 0.426 mmol), ethanol (3.0 mL), and 1-[2-methyl-3-(trifluoromethyl)phenyl]thiourea (90.8 mg, 0.388 mmol) were used to carry out the reaction. After the solution was stirred for overnight and work-up, the residue was purified by Isco Combi-Flash Companion column chromatography (0-50% EtOAc in n-hexane). The collected solid was washed with diethyl ether to give 2',4'-dimethyl-N-[2-methyl-3-(trifluoromethyl)phenyl]-4,5'-bi-1,3-thiazol-2-amine (35.6 mg, 25%) as a green solid.

$^1$H NMR (DMSO-d$_6$, 400 MHz) δ 9.67 (br s, 1H), 8.17 (d, 1H), 7.47-7.38 (m, 2H), 6.95 (s, 1H), 2.56 (s, 3H), 2.47 (s, 3H), 2.35 (s, 3H); LC-MS (APCI) m/z: 370.1 [M+H]$^+$.

EXAMPLE 45

3-[(2',4'-Dimethyl-4,5'-bi-1,3-thiazol-2-yl)amino]-2-methylphenol

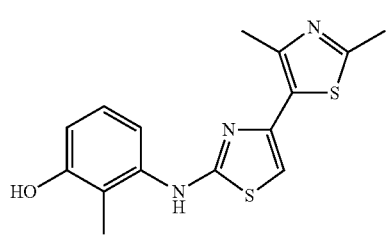

Compound 89

Step 1. N-[(3-hydroxy-2-methylphenyl)carbamothioyl]benzamide

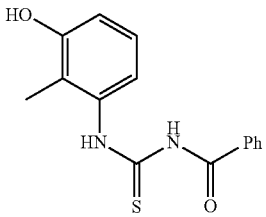

Compound 90

Following the procedure C, 3-amino-2-methylphenol (0.590 g, 4.79 mmol), benzoyl isothiocyante (0.710 mL, 5.27 mmol), and acetone (12 mL) were used to carry out the reaction. After the reaction was stirred for 40 min and work-up, N-[(3-hydroxy-2-methylphenyl)carbamothioyl]benzamide (1.16 g, 85%) was afforded as a beige solid.

$^1$H NMR (CDCl$_3$, 400 MHz) δ 12.19 (br s, 1H), 9.18 (br s, 1H), 7.92 (d, 2H), 7.67 (t, 1H), 7.56 (dd, 2H), 7.26 (d overlapped with solvent peak, 1H), 7.15 (dd, 1H), 6.79 (d, 1H), 4.96 (br s, 1H), 2.24 (s, 3H).

Step 2. 1-(3-Hydroxy-2-methylphenyl)thiourea

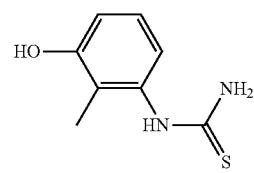

Compound 91

A solution of N-[(3-hydroxy-2-methylphenyl)carbamothioyl]benzamide (0.480 g, 1.68 mmol) in 5% NaOH$_{(aq)}$ (8.0 mL) was stirred at 70° C. for 3 h. After the solution was cooled to room temperature, it was quenched with 5% HCl$_{(aq)}$. The precipitation was collected by filtration to give 1-(3-hydroxy-2-methylphenyl)thiourea (0.128 g, 42%) as a beige solid.

$^1$H NMR (DMSO-d$_6$, 300 MHz) δ 9.60-9.30 (br s, 1H), 9.24 (br s, 1H), 7.14 (br s, 2H), 6.95 (dd, 1H), 6.72 (d, 1H), 6.60 (d, 1H), 1.95 (s, 3H).

Step 3. 3-[(2',4'-Dimethyl-4,5'-bi-1,3-thiazol-2-yl)amino]-2-methylphenol

Following the procedure B, 2-bromo-1-(2,4-dimethylthiazol-5-yl)ethanone (113 mg, 0.481 mmol), ethanol (3.0 mL), and 1-(3-hydroxy-2-methylphenyl)thiourea (79.7 mg, 0.437 mmol) were used to carry out the reaction. After the solution was stirred for overnight and work-up, the residue was purified by Isco Combi-Flash Companion column chromatography (0-60% EtOAc in n-hexane) to give 3-[(2',4'-dimethyl-4,5'-bi-1,3-thiazol-2-yl)amino]-2-methylphenol (14.1 mg, 10%) as a yellow solid.

$^1$H NMR (DMSO-d$_6$, 300 MHz) δ 9.40 (s, 1H), 9.38 (s, 1H), 7.17 (d, 1H), 6.97 (dd, 1H), 6.82 (s, 1H), 6.62 (s, 1H), 2.56 (s, 3H), 2.47 (s, 3H), 2.05 (s, 3H); LC-MS (APCI) m/z: 318.1 [M+H]$^+$.

EXAMPLE 46

N-(2-Ethylphenyl)-4'-methyl-2'-phenyl-4,5'-bi-1,3-thiazol-2-amine

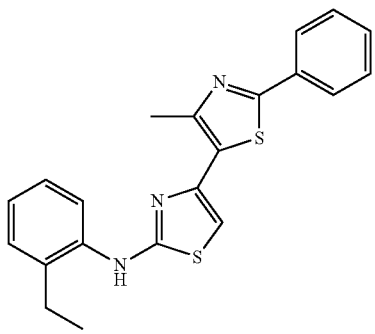

Compound 92

Following the procedure B, 2-bromo-1-(4-methyl-2-phenyl-1,3-thiazol-5-yl)-1-ethanone (73.4 mg, 0.248 mmol), ethanol (2.0 mL), and 1-(2-ethylphenyl)thiourea (44.7 mg, 0.248 mmol) were used to carry out the reaction. After the solution was stirred for overnight and work-up, the residue was purified by column chromatography (20% EtOAc in n-hexane) to give N-(2-ethylphenyl)-4'-methyl-2'-phenyl-4,5'-bi-1,3-thiazol-2-amine (81.4 mg, 87%) as a brown gum.

$^1$H NMR (CDCl$_3$, 400 MHz) δ 7.95 (d, 2H), 7.61 (d, 1H), 7.50-7.27 (m, 5H), 7.22 (dd, 1H), 6.61 (s, 1H), 2.78-2.68 (m, 5H), 1.26 (t, 3H); LC-MS (APCI) m/z: 378.2 [M+H]$^+$.

EXAMPLE 47

N-(2,4-Dimethylphenyl)-4'-methyl-2'-phenyl-4,5'-bi-1,3-thiazol-2-amine

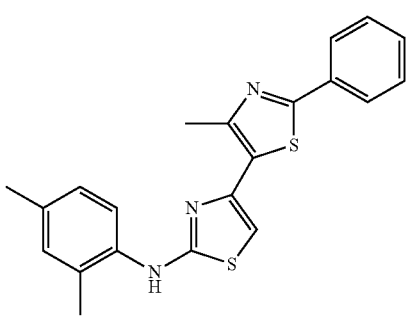

Compound 93

Following the procedure B, 2-bromo-1-(4-methyl-2-phenyl-1,3-thiazol-5-yl)-1-ethanone (73.4 mg, 0.248 mmol), ethanol (2.0 mL), and 1-(2,4-dimethylphenyl)thiourea (44.7 mg, 0.248 mmol) were used to carry out the reaction. After the solution was stirred for 6 hours and work-up, the residue was purified by column chromatography (20% EtOAc in n-hexane) to give N-(2,4-dimethylphenyl)-4'-methyl-2'-phenyl-4,5'-bi-1,3-thiazol-2-amine (60.9 mg, 65%) as an orange solid.

$^1$H NMR (CDCl$_3$, 400 MHz) δ 7.95 (d, 2H), 7.50-7.40 (m, 4H), 7.40-7.20 (br s, 1H), 7.09-7.05 (m, 2H), 6.59 (s, 1H), 2.69 (s, 3H), 2.34 (s, 3H), 2.31 (s, 3H); LC-MS (APCI) m/z: 378.1 [M+H]$^+$.

EXAMPLE 48

2'-(4-Chlorophenyl)-N-(2-ethylphenyl)-4'-methyl-4,5'-bi-1,3-thiazol-2-amine

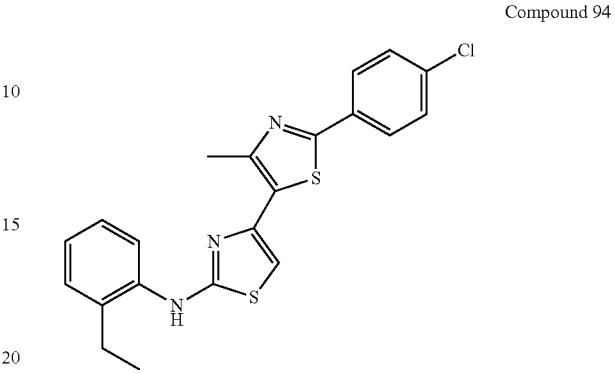

Compound 94

Following the procedure B, 2-bromo-1-[2-(4-chlorophenyl)-4-methyl-1,3-thiazol-5-yl]-1-ethanone (90.2 mg, 0.273 mmol), ethanol (2.0 mL), and 1-(2-ethylphenyl)thiourea (49.2 mg, 0.273 mmol) were used to carry out the reaction. After the solution was stirred for 5 h and work-up, the residue was purified by Isco Combi-Flash Companion column chromatography (0-20% EtOAc in n-hexane) to give 2'-(4-chlorophenyl)-N-(2-ethylphenyl)-4'-methyl-4,5'-bi-1,3-thiazol-2-amine (91.3 mg, 81%) as an orange solid.

$^1$H NMR (CDCl$_3$, 300 MHz) δ 7.88 (d, 2H), 7.60 (d, 1H), 7.39 (d, 2H), 7.38-7.17 (m, 3H), 6.61 (s, 1H), 2.78-2.62 (m, 5H), 1.25 (t, 3H); LC-MS (ESI) m/z: 412.0 [M+H]$^+$.

EXAMPLE 49

2'-Ethyl-N-(2-ethylphenyl)-4'-methyl-4,5'-bi-1,3-thiazol-2-amine

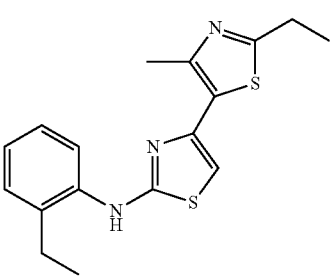

Compound 95

Step 1. 5-Acetyl-2-ethyl-4-dimethylthiazole

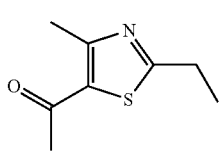

Compound 96

A solution of thiopropionate (0.890 g, 9.98 mmol) and 3-chloro-penta-2,4-dione (1.48 g, 11.0 mmol) in ethanol (30 mL) was stirred at reflux for 24 h. After the solution was cooled to room temperature and concentrated, it was treated with saturated NaHCO$_{3(aq)}$ and extracted with CH$_2$Cl$_2$. The combined organic layers were dried over MgSO$_{4(s)}$, filtered, concentrated, and dried under high vacuum to give 5-acetyl-2-ethyl-4-dimethylthiazole (1.41 g, 83%) as a brown liquid.

$^1$H NMR (CDCl$_3$, 400 MHz) δ2.99 (q, 2H), 2.69 (s, 3H), 2.50 (s, 3H), 1.38 (t 3H).

Step 2. 2-Bromo1-(2-ethyl-4-methyl-thiazol-5-yl)-ethanone

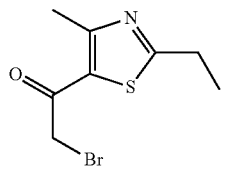

Compound 97

To a solution of 5-acetyl-2-ethyl-4-dimethylthiazole (0.801 g, 4.73 mmol) in 33% of HBr in acetic acid (6.0 mL) was added phenyltrimethylammonium tribromide (1.87 g, 4.97 mmol) at room temperature. After the solution was stirred for overnight, it was poured into ice water and extracted with CH$_2$Cl$_2$. The combined organic layers were washed with water, dried over MgSO$_{4(s)}$, filtered, and concentrated under reduced pressure to afford a residue. The residue was purified by Isco Combi-Flash Companion column chromatography (0-5% EtOAc in CH$_2$Cl$_2$) to give 2-bromo-1-(2-ethyl-4-dimethyl-thiazol-5-yl)ethanone (0.710 g, 61%) as a brown solid.

$^1$H NMR (CDCl$_3$, 400 MHz) δ 4.23 (s, 2H), 3.03 (q, 2H), 2.73 (s, 3H), 1.41 (t, 3H).

Step 3. 2'-Ethyl-N-(2-ethylphenyl)-4'-methyl-4,5'-bi-1,3-thiazol-2-amine

Following the procedure B, 2-bromo-1-(2-ethyl-4-dimethyl-thiazol-5-yl)-ethanone (110 mg, 0.445 mmol), ethanol (3.0 mL), and 1-(2-ethylphenyl)thiourea (80.3 mg, 0.445 mmol) were used to carry out the reaction. After the solution was stirred for 2 h and work-up, the residue was purified by Isco Combi-Flash Companion column chromatography (0-30% EtOAc in n-hexane) to give 2'-ethyl-N-(2-ethylphenyl)-4'-methyl-4,5'-bi-1,3-thiazol-2-amine (90.6 mg, 63%) as a beige solid.

$^1$H NMR (CDCl$_3$, 400 MHz) δ 7.60 (d, 1H), 7.30-7.25 (m, 2H), 7.18 (dd overlapped with br s at 7.16, 1H), 7.16 (br s overlapped with dd at 7.18, 1H), 6.53 (s, 1H), 3.00 (q, 2H), 2.68 (q, 2H), 2.59 (s, 3H), 1.40 (t, 3H), 1.25 (t, 3H); LC-MS (ESI) m/z: 330.1 [M+H]$^+$.

EXAMPLE 50

N-(2-Ethylphenyl)-2',4',5-trimethyl-4,5'-bi-1,3-thiazol-2-amine

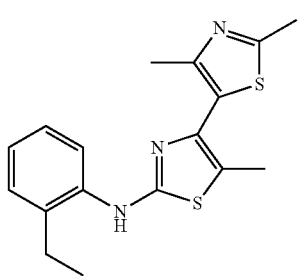

Compound 98

Step 1. 2-Bromo1-(2,4-dimethyl-thiazol-5-yl)propan-1-one

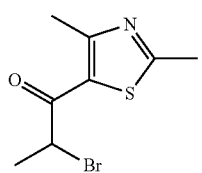

Compound 99

To a solution of 1-(2,4-dimethylthiazol-5-yl)propan-1-one (0.101 g, 0.599 mmol) in 33% of HBr in acetic acid (0.80 mL) was added phenyltrimethylammonium tribromide (0.246 g, 0.658 mmol) at room temperature. After the solution was stirred for 36 h, it was poured into ice water and extracted with CH$_2$Cl$_2$. The combined organic layers were dried over MgSO$_{4(s)}$, filtered, and concentrated under reduced pressure to afford a residue. The residue was purified by column chromatography (5% EtOAc in CH$_2$Cl$_2$) to give 2-bromo1-(2,4-dimethyl-thiazol-5-yl)propan-1-one (0.130 g, 88%) as a yellow liquid.

$^1$H NMR (CDCl$_3$, 400 MHz) δ 4.81 (q, 1H), 2.73 (s, 3H), 2.72 (s, 3H), 1.86 (d, 3H).

Step 2. N-(2-Ethylphenyl)-2',4',5-trimethyl-4,5'-bi-1,3-thiazol-2-amine

Following the procedure B, 2-bromo1-(2,4-dimethyl-thiazol-5-yl)propan-1-one (126 mg, 0.506 mmol), ethanol (3.0 mL), and 1-(2-ethylphenyl)thiourea (91.2 mg, 0.506 mmol) were used to carry out the reaction. After the solution was stirred for overnight and work-up, the residue was purified by Isco Combi-Flash Companion column chromatography (0-30% EtOAc in n-hexane) to give N-(2-ethylphenyl)-2',4',5-trimethyl-4,5'-bi-1,3-thiazol-2-amine (120 mg, 72%) as a yellow solid.

$^1$H NMR (CDCl$_3$, 400 MHz) δ 7.55 (d, 1H), 7.26-7.20 (m, 2H), 7.13 (dd, 1H), 2.78-2.60 (m, 5H), 2.36 (s, 3H), 2.22 (s, 3H), 1.23 (t, 3H); LC-MS (ESI) m/z: 330.1 [M+H]$^+$.

EXAMPLE 51

N$^2$-(2-ethylphenyl)-4'-methyl-4,5'-bi-1,3-thiazole-2,2'-diamine

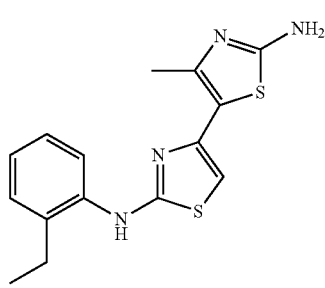

Compound 100

Step 1. 1-(2-Amino-4-methyl-1,3-thiazol-5-yl)-2-bromoethanone hydrobromide

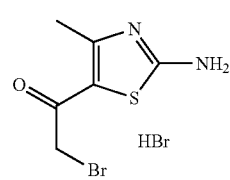

Compound 101

A solution of 5-acetyl-2-amino-4-methylthiazole (0.101 g, 0.599 mmol) and phenyltrimethylammonium tribromide (0.246 g, 0.658 mmol) in 33% of HBr in acetic acid was stirred at room temperature for overnight. The solution was poured into ice water and CH$_2$Cl$_2$. The undissolved solid was collected from the organic layer and washed with diethyl ether to give 1-(2-amino-4-methyl-1,3-thiazol-5-yl)-2-bromoethanone hydrobromide (0.680 g, 47%) as a white solid.

$^1$H NMR (DMSO-d$_6$, 300 MHz) δ 8.90-8.40 (br, 2H), 4.53 (s, 2H), 2.46 (s, 3H).

Step 2. N$^2$-(2-ethylphenyl)-4'-methyl-4,5'-bi-1,3-thiazole-2,2'-diamine

Following the procedure B, 1-(2-amino-4-methyl-1,3-thiazol-5-yl)-2-bromoethanone hydrobromide (122 mg, 0.387 mmol), ethanol (3.0 mL), and 1-(2-ethylphenyl)thiourea (69.8 mg, 0.387 mmol) were used to carry out the reaction. After the solution was stirred for overnight and work-up, the residue was purified by Isco Combi-Flash Companion column chromatography (0-90% EtOAc in n-hexane) to give N$^2$-(2-ethylphenyl)-4'-methyl-4,5'-bi-1,3-thiazole-2,2'-diamine (88.6 mg, 72%) as a red solid.

$^1$H NMR (CDCl$_3$, 400 MHz) δ 7.59 (d, 1H), 7.29-7.24 (m, 2H), 7.16 (dd, 1H), 7.15-7.00 (br s, 1H), 6.38 (s, 1H), 5.40-5.10 (br s, 2H), 2.67 (q, 2H), 2.53 (s, 3H), 1.24 (t, 3H); LC-MS (ESI) m/z: 317.0 [M+H]$^+$.

EXAMPLE 52

4-(2,4-Dimethyl-1,3-oxazol-5-yl)-N-(2-ethylphenyl)-1,3-thiazol-2-amine

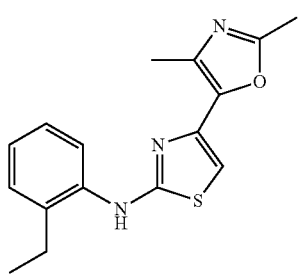

Compound 102

Step 1. 5-Acetyl-2,4-dimethyloxazole

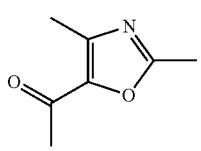

Compound 103

A solution of 3-chloropentan-2,4-dione (6.32 g, 0.470 mol) and ammonium acetate (10.86 g, 1.409 mol) in acetic acid (30 mL) was stirred at reflux for 6.0 h and cooled to room temperature. After the reaction mixture was poured into ice water, the solution was neutralized with 30% NaOH$_{(aq)}$ (to pH>5) and extracted with CHCl$_3$. The combined organic layers were dried over MgSO$_{4(s)}$, filtered, and concentrated under reduced pressure to afford a residue. The residue was purified by flash column chromatography (30% EtOAc in n-hexanes) to give 5-acetyl-2,4-dimethyloxazole (2.77 g, 42%) as a brown oil.

$^1$H NMR (CDCl$_3$, 400 MHz) δ 2.50 (s, 3H), 2.45 (s, 6H).

Step 1. 2-Bromo-1-(2,4-dimethyl-oxazol-5-yl)ethanone

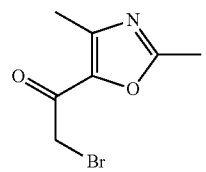

Compound 104

To a solution of 5-acetyl-2,4-dimethyloxazole (0.360 g, 2.59 mmol) in 33% of HBr in acetic acid (4.0 mL) was added phenyltrimethylammonium tribromide (0.971 g, 2.59 mmol) at room temperature. After the solution was stirred for overnight, it was poured into ice water and extracted with CH$_2$Cl$_2$. The combined organic layers were washed with water, dried over MgSO$_{4(s)}$, filtered, and concentrated under reduced pressure to afford a residue. The residue was purified by Isco Combi-Flash Companion column chromatography (0-3% EtOAc in CH$_2$Cl$_2$) to give 2-bromo-1-(2,4-dimethyl-oxazol-5-yl)ethanone (0.160 g, 30%) as a brown oil.

$^1$H NMR (CDCl$_3$, 400 MHz) δ 4.27 (s, 2H), 2.54 (s, 3H), 2.49 (s, 3H).

Step 3. 4-(2,4-Dimethyl-1,3-oxazol-5-yl)-N-(2-ethylphenyl)-1,3-thiazol-2-amine

Following the procedure B, 2-bromo-1-(2,4-dimethyl-oxazol-5-yl)ethanone (99.6 mg, 0.457 mmol), ethanol (3.0 mL), and 1-(2-ethylphenyl)thiourea (73.9 mg, 0.410 mmol) were used to carry out the reaction. After the solution was stirred for 4 h and work-up, the residue was purified by Isco Combi-Flash Companion column chromatography (5-40% EtOAc in n-hexane) to give 4-(2,4-dimethyl-1,3-oxazol-5-yl)-N-(2-ethylphenyl)-1,3-thiazol-2-amine (74.2 mg, 60%) as a orange solid.

$^1$H NMR (CDCl$_3$, 300 MHz) δ 7.62 (d, 1H), 7.30-7.24 (m, 2H), 7.16 (dd, 1H) 7.01 (br s, 1H), 6.61 (s, 1H), 2.68 (q, 2H), 2.48 (s, 3H), 2.43 (s, 3H), 1.24 (t, 3H); LC-MS (ESI) m/z: 300.1 [M+H]$^+$.

EXAMPLE 53

4-(2,4-Dimethyl-1,3-oxazol-5-yl)-N-(2,4-dimethylphenyl)-1,3-thiazol-2-amine

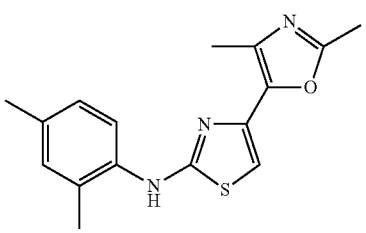

Compound 105

Following the procedure B, 2-bromo-1-(2,4-dimethyl-oxazol-5-yl)ethanone (76.5 mg, 0.351 mmol), ethanol (3.0 mL), and 1-(2,4-dimethylphenyl)thiourea (63.2 mg, 0.351 mmol) were used to carry out the reaction. After the solution was stirred for 3 h and work-up, the residue was purified by Isco Combi-Flash Companion column chromatography (0-40% EtOAc in n-hexane) to give 4-(2,4-dimethyl-1,3- oxazol-5-yl)-N-(2,4-dimethylphenyl)-1,3-thiazol-2-amine (91.6 mg, 87%) as a red brown solid.

$^1$H NMR (CDCl$_3$, 400 MHz) δ 7.44 (d, 1H), 7.08-7.06 (m, 2H), 6.58 (s, 1H), 2.47 (s, 3H,), 2.43 (s, 3H), 2.33 (s, 3H), 2.30 (s, 3H); LC-MS (ESI) m/z: 300.1 [M+H]$^+$.

EXAMPLE 54

4-(2,4-Dimethyl-1,3-oxazol-5-yl)-N-(2,4,6-trimethylphenyl)-1,3-thiazol-2-amine

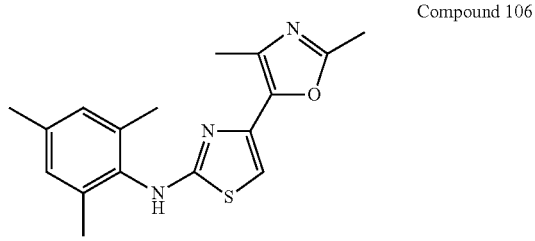

Compound 106

Following the procedure B, 2-bromo-1-(2,4-dimethyl-oxazol-5-yl)ethanone (78.3 mg, 0.359 mmol), ethanol (3.0 mL), and 1-(2,4,6-trimethylphenyl)thiourea (69.8 mg, 0.359 mmol) were used to carry out the reaction. After the solution was stirred for 3 h and work-up, the residue was purified by Isco Combi-Flash Companion column chromatography (0-20% EtOAc in n-hexane) to give 4-(2,4-dimethyl-1,3-oxazol-5-yl)-N-(2,4,6-trimethylphenyl)-1,3-thiazol-2-amine (82.7 mg, 74%) as a beige solid.

$^1$H NMR (CDCl$_3$, 300 MHz) δ 6.97 (s, 2H), 6.49 (s, 1H), 2.46 (s, 3H), 2.41 (s, 3H), 2.32 (s, 3H), 2.27 (s, 6H); LC-MS (ESI) m/z: 314.1 [M+H]$^+$.

EXAMPLE 55

5-(2,4-Dimethyl-1,3-thiazol-5-yl)-N-(2-ethylphenyl)-1,3-oxazol-2-amine

Compound 107

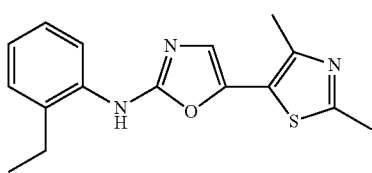

Step 1. 2-Azido-1-(2,4-dimethyl-thiazol-5-yl)ethanone

Compound 108

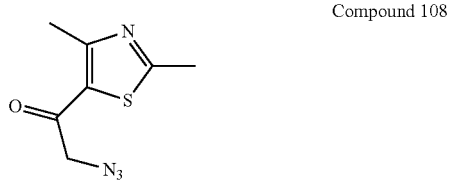

To a solution of 2-bromo-1-(2,4-dimethyl-thiazol-5-yl)ethanone (301 mg, 1.28 mmol) in dimethylformamide (3.0 mL) was added sodium azide (100 mg, 1.54 mmol) at room temperature and it was stirred for 40 min. The reaction solution was quenched with water and extracted with EtOAc. The combined organic layers were dried over MgSO$_{4(s)}$, filtered, concentrated, and dried under high vacuum to give 2-azido-1-(2,4-dimethyl-thiazol-5-yl)ethanone (238 mg, 93%) as a brown solid.

$^1$H NMR (CDCl$_3$, 400 MHz) δ 4.26 (s, 2H), 2.73 (s, 6H).

Step 2. 5-(2,4-Dimethyl-1,3-thiazol-5-yl)-N-(2-ethylphenyl)-1,3-oxazol-2-amine

To a solution of 2-azido-1-(2,4-dimethyl-thiazol-5-yl)ethanone (108 mg, 0.552 mmol) and triphenylphosphine (217 mg, 0.828 mmol) in THF (5.0 mL) was added 2-ethylphenyl isocyanate (86.0 µL, 0.610 mmol) at room temperature. After stirred at room temperature for 4 hours, the mixture was quenched by added saturated NaHCO$_{3(aq)}$, and extracted with CH$_2$Cl$_2$. The combined organic layers were dried over MgSO$_{4(s)}$, filtered, and concentrated to afford a residue. The residue was purified by Isco Combi-Flash Companion column chromatography (5-60% EtOAc in n-hexane) to give an oil. The resultant oil were recrystallized with a mixture of CH$_2$Cl$_2$ and ether to give 5-(2,4-dimethyl-1,3-thiazol-5-yl)-N-(2-ethylphenyl)-1,3-oxazol-2-amine (5.1 mg, 3%).

$^1$H NMR (CDCl$_3$, 400 MHz) δ 7.96 (d, 1H), 7.29-7.22 (m, 2H), 7.06 (dd, 1H), 6.90 (s, 1H), 6.67 (br s, 1H), 2.69 (s overlapped with q at 2.68, 3H), 2.68 (q overlapped with s at 2.69, 2H), 2.49 (s, 3H), 1.30 (t, 3H); LC-MS (ESI) m/z: 300.1 [M+H]$^+$.

EXAMPLE 56

5-(2,4-Dimethyl-1,3-oxazol-5-yl)-N-(2-ethylphenyl)-1,3-oxazol-2-amine

Compound 109

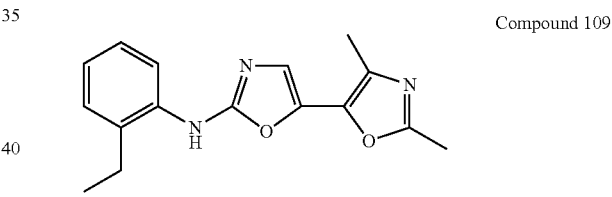

Step 1. 2-Azido-1-(2,4-dimethyl-oxazol-5-yl)ethanone

Compound 110

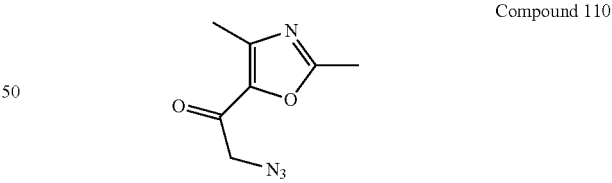

To a solution of 2-bromo-1-(2,4-dimethyl-oxazol-5-yl)ethanone (1.10 g, 5.04 mmol) in dimethylformamide (10 mL) was added sodium azide (0.393 g, 6.05 mmol) at room temperature and it was stirred for 1.5 h. The reaction solution was quenched with water and extracted with EtOAc. The combined organic layers were dried over MgSO$_{4(s)}$, filtered, concentrated. The residue was purified by column chromatography (40% EtOAc in n-hexane) to give 2-azido-1-(2,4-dimethyl-oxazol-5-yl)ethanone (0.720 g, 79%) as a brown oil.

$^1$H NMR (CDCl$_3$, 300 MHz) δ 4.32 (s, 2H), 2.51 (s, 3H), 2.49 (s, 3H).

Step 2. 5-(2,4-Dimethyl-1,3-oxazol-5-yl)-N-(2-ethylphenyl)-1,3-oxazol-2-amine

A solution of 2-azido-1-(2,4-dimethyl-thiazol-5-yl)ethanone (135 mg, 0.752 mmol), 2-ethylphenyl isothiocyanate (102 mg, 0.626 mmol) and triphenylphosphine (97.1 mg, 0.752 mmol) in 1,4-dioxane (3.0 mL) was stirred at 65° C. for 2 h. After the solvent was removed under reduced pressure, the residue was purified by Isco Combi-Flash Companion column chromatography (0-40% EtOAc in n-hexane) and (0-20% EtOAc in n-hexane) to give 5-(2,4-dimethyl-1,3-oxazol-5-yl)-N-(2-ethylphenyl)-1,3-oxazol-2-amine (5.1 mg, 3%) as a yellow solid $^1$H NMR (CDCl$_3$, 400 MHz) δ 7.91 (d, 1H), 7.27-7.23 (m, 2H), 7.09 (dd, 1H), 6.98 (s, 1H), 2.68 (q, 2H), 2.47 (s, 3H), 2.27 (s, 3H), 1.29 (t, 3H); LC-MS (APCI) m/z: 284.2 [M+H]$^+$.

EXAMPLE 57

Methyl {2-[(2',4'-dimethyl-4,5'-bi-1,3-thiazol-2-yl)amino]-1,3-thiazol-5-yl}acetate

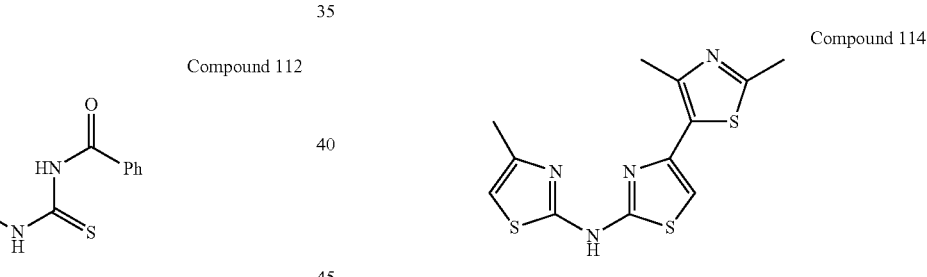

Step 1. Methyl {2-[(benzoylcarbamothioyl)amino]-1,3-thiazol-5-yl}acetate

Compound 112

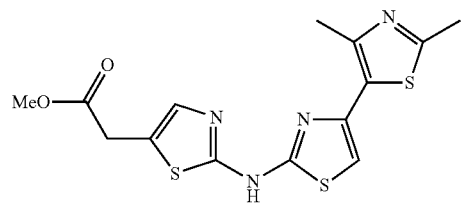 [SMILES: COC(=O)Cc1cnc(Nc2nc(-c3sc(C)nc3C)cs2)s1]

Following the procedure C, (2-amino-thiazol-5-yl)-acetic acid methyl ether (0.590 g, 3.43 mmol), benzoyl isothiocyante (0.510 mL, 3.77 mmol), and acetone (10 mL) were used to carry out the reaction. After the reaction was stirred for 40 min and work-up, methyl {2-[(benzoylcarbamothioyl)amino]-1,3-thiazol-5-yl}acetate (0.750 g, 65%) was afforded as a yellow solid.

$^1$H NMR (CDCl$_3$, 400 MHz) δ 9.12 (br s, 1H), 7.91 (d, 2H), 7.67 (dd, 1H), 7.56 (dd, 2H), 6.91 (s, 1H), 3.78 (s, 2H), 3.75 (s, 3H).
Step 2. Methyl [2-(carbamothioylamino)-1,3-thiazol-5-yl]acetate Compound 113

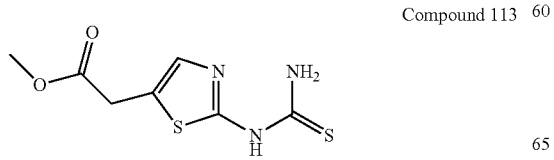

A solution of methyl {2-[(benzoylcarbamothioyl)amino]-1,3-thiazol-5-yl}acetate (285 mg, 0.850 mmol) and NaOMe (68.9 mg, 1.28 mmol) in methanol (5.0 mL) was stirred at room temperature for 3 h. To the reaction mixture was added another 1.5 eq of NaOMe and it was stirred for overnight. After the solution was quenched with saturated NH$_4$Cl$_{(aq)}$ and extracted with CH$_2$Cl$_2$. The combined organic layers were dried over MgSO$_{4(s)}$, filtered, and concentrated to give methyl [2-(carbamothioylamino)-1,3-thiazol-5-yl]acetate (0.128 g, 65%) as an orange solid. 1H NMR (CDCl$_3$+ MeOD, 400 MHz) δ 6.66 (s, 1H), 3.66 (s, 3H), 3.61 (s, 2H).

Step 3. Methyl {2-[(2',4'-dimethyl-4,5'-bi-1,3-thiazol-2-yl)amino]-1,3-thiazol-5-yl}acetate Following the procedure B, 2-bromo-1-(2,4-dimethyl-thiazol-5-yl)ethanone (116 mg, 0.495 mmol), ethanol (3.0 mL), and methyl [2-(carbamothioylamino)-1,3-thiazol-5-yl]acetate (95.4 mg, 0.412 mmol) were used to carry out the reaction. After the solution was stirred for 5 h and work-up, the residue was purified by Isco Combi-Flash Companion column chromatography (0-60% EtOAc in n-hexane) to give methyl {2-[(2',4'-dimethyl-4,5'-bi-1,3-thiazol-2-yl)amino]-1,3-thiazol-5-yl}acetate (100 mg, 66%) as a solid.

$^1$H NMR (CDCl$_3$, 300 MHz) δ 6.75 (s, 1H), 6.67 (s, 1H), 3.75 (s, 3H), 3.73 (s, 2H), 2.68 (s, 3H), 2.62 (s, 3H); LC-MS (APCI) m/z: 367.1 [M+H]$^+$.

EXAMPLE 58

2',4'-Dimethyl-N-(4-methyl-1,3-thiazol-2-yl)-4,5'-bi-1,3-thiazol-2-amine

Compound 114

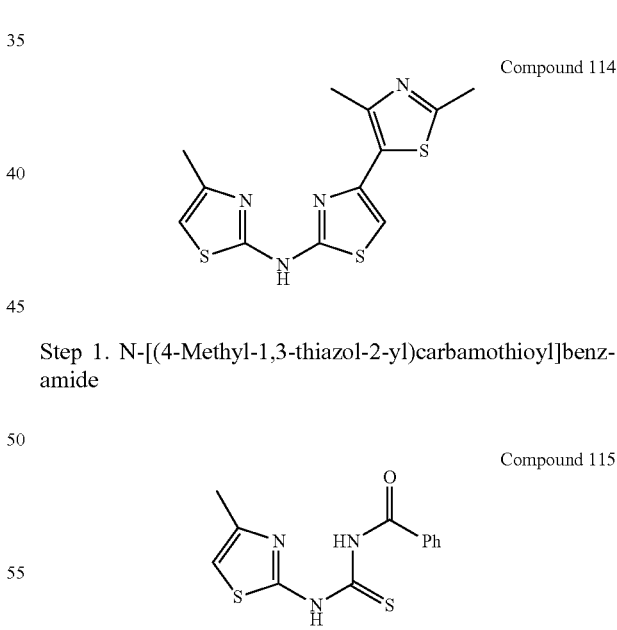

Step 1. N-[(4-Methyl-1,3-thiazol-2-yl)carbamothioyl]benzamide

Compound 115

Following the procedure C, 2-amino-4-methylthiazole (0.400 g, 3.50 mmol), benzoyl isothiocyante (0.520 mL, 3.87 mmol), and acetone (12 mL) were used to carry out the reaction. After the reaction was stirred for 40 min and work-up, N-[(4-methyl-1,3-thiazol-2-yl)carbamothioyl]benzamide (0.790 g, 81%) was afforded as an orange solid.

$^1$H NMR (CDCl$_3$, 400 MHz) δ 9.10 (br s, 1H), 7.91 (d, 2H), 7.65 (dd, 1H), 7.56 (dd, 2H), 6.62 (s, 1H), 2.41 (s, 3H).

Step 2. 1-(4-Methyl-1,3-thiazol-2-yl)thiourea

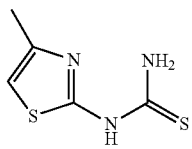

A solution of N-[(4-methyl-1,3-thiazol-2-yl)carbamothioyl]benzamide (0.420 g, 1.51 mmol) and NaOMe (0.245 g, 4.53 mmol) in methanol (10 mL) was stirred at room temperature for 16 h. The solvent was removed and quenched with saturated $NH_4Cl_{(aq)}$ and extracted with $CH_2Cl_2$. The combined organic layers were dried over $MgSO_{4(s)}$, filtered, and concentrated to give 1-(4-methyl-1,3-thiazol-2-yl)thiourea (79.8 mg, 31%) as an orange solid.
$^1$H NMR (DMSO-$d_6$, 300 MHz) δ 11.48 (br s, 1H), 8.80 (br s, 2H), 6.66 (s, 1H), 2.21 (s, 3H).

Step 3. 2',4'-Dimethyl-N-(4-methyl-1,3-thiazol-2-yl)-4,5'-bi-1,3-thiazol-2-amine Following the procedure B, 2-bromo-1-(2,4-dimethylthiazol-5-yl)ethanone (102 mg, 0.437 mmol), ethanol (3.0 mL), and 1-(4-methyl-1,3-thiazol-2-yl)thiourea (68.8 mg, 0.397 mmol) were used to carry out the reaction. After the solution was stirred for overnight and work-up, the residue was purified by Isco Combi-Flash Companion column chromatography (0-60% EtOAc in n-hexane) to give 2',4'-dimethyl-N-(4-methyl-1,3-thiazol-2-yl)-4,5'-bi-1,3-thiazol-2-amine (95.6 mg, 79%) as a beige solid.
$^1$H NMR (CDCl$_3$, 300 MHz) δ 6.76 (s, 1H), 6.27 (br s, 1H), 2.69 (s, 3H), 2.63 (s, 3H), 2.34 (s, 3H); LC-MS (APCI) m/z: 309.1 [M+H]$^+$.

EXAMPLE 59

N-(1,3-Benzothiazol-2-yl)-2',4'-dimethyl-4,5'-bi-1,3-thiazol-2-amine

Compound 117

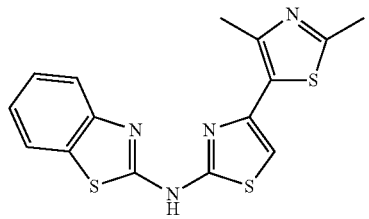

Step 1. N-(1,3-Benzothiazol-2-ylcarbamothioyl)benzamide

Compound 118

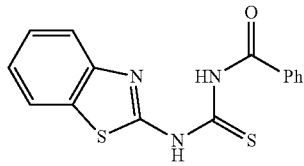

Following the procedure C, 2-amino-benzothiazole (0.320 g, 2.13 mmol), benzoyl isothiocyante (0.300 mL, 2.22 mmol), and acetone (10 mL) were used to carry out the reaction. After the reaction was stirred for 50 min and work-up, N-(1,3-benzothiazol-2-ylcarbamothioyl)benzamide (0.330 g, 49%) was afforded as a yellow solid.
$^1$H NMR (DMSO-$d_6$, 300 MHz) δ 12.87 (br s, 1H), 12.27 (br s, 1H), 8.13 (d, 1H), 8.06-7.99 (m, 2H), 7.80 (t, 1H), 7.71-7.31 (m, 5H).

Step 2. 1-(1,3-Benzothiazol-2-yl)thiourea

Compound 118

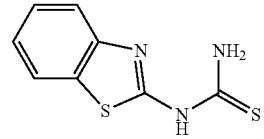

A solution of N-(1,3-benzothiazol-2-ylcarbamothioyl)benzamide (0.320 g, 1.02 mmol) and NaOMe (0.170 g, 3.15 mmol) in methanol (10 mL) was stirred at room temperature for overnight. The solvent was removed. The residue was treated with saturated $NH_4Cl_{(aq)}$ and extracted with $CH_2Cl_2$ and EtOAc. The combined organic layers were dried over $MgSO_{4(s)}$, filtered, and concentrated. The residue was purified by column chromatography (40% EtOAc in n-hexane) to give 1-(1,3-benzothiazol-2-yl)thiourea (36.9 mg, 17%) as a white solid.
$^1$H NMR (DMSO-$d_6$, 300 MHz) δ 11.80 (br s, 1H), 9.12 (br s, 2H), 7.92 (d, 1H), 7.70 (br d, 1H), 7.40 (dd, 1H), 7.27 (dd, 1H).

Step 3. N-(1,3-Benzothiazol-2-yl)-2',4'-dimethyl-4,5'-bi-1,3-thiazol-2-amine

Following the procedure B, 2-bromo-1-(2,4-dimethylthiazol-5-yl)ethanone (44.4 mg, 0.190 mmol), ethanol (2.0 mL), and 1-(1,3-benzothiazol-2-yl)thiourea (36.1 mg, 0.172 mmol) were used to carry out the reaction. After the solution was stirred for 6 h and work-up, the solid was collected by filtration and washed with water and $CH_2Cl_2$ to give N-(1,3-benzothiazol-2-yl)-2',4'-dimethyl-4,5'-bi-1,3-thiazol-2-amine (34.8 mg, 59%) as a lightly brown solid.
$^1$H NMR (DMSO-$d_6$, 400 MHz) δ 7.85 (br d, 1H), 7.54 (br s, 1H), 7.37 (dd, 1H), 7.25-7.10 (m, 2H), 2.60 (s, 3H), 2.54 (s, 3H); LC-MS (ESI) m/z: 345.0 [M+H]$^+$.

EXAMPLE 60

4-(2,4-Dimethylphenyl)-N-(2-ethylphenyl)-1,3-thiazol-2-amine

Compound 120

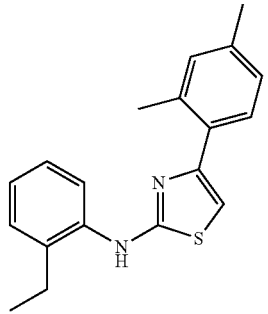

Following the procedure B, 2-bromo-1-(2,4-dimethylphenyl)ethanone (130 mg, 0.572 mmol), ethanol (3.0 mL), and 1-(2-ethylphenyl)thiourea (93.8 mg, 0.520 mmol) were used to carry out the reaction. After the solution was stirred for 1.5 h and work-up, the residue was purified by Isco Combi-Flash Companion column chromatography (0-7% EtOAc in n-hexane) to give 4-(2,4-dimethylphenyl)-N-(2-ethylphenyl)-1,3-thiazol-2-amine (122 mg, 76%) as a yellow solid.

$^1$H NMR (CDCl$_3$, 400 MHz) δ 7.67 (d, 1H), 7.48 (d, 1H), 7.28-7.22 (m, 2H), 7.13 (dd, 1H), 7.10-7.03 (m, 2H), 6.48 (s, 1H), 2.68 (q, 2H), 2.45 (s, 3H), 2.34 (s, 3H), 1.25 (t, 3H); LC-MS (APCI) m/z: 309.2 [M+H]$^+$.

EXAMPLE 61

N-(2-Ethylphenyl)-4-(4-methylphenyl)-1,3-thiazol-2-amine

Compound 121

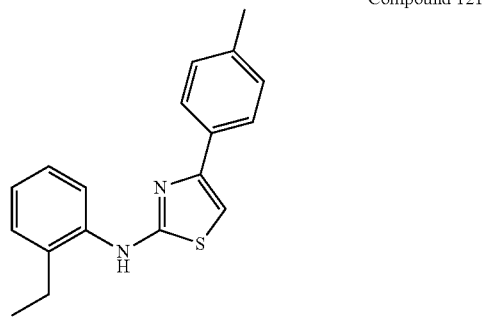

Following the procedure B, 2-bromo-4-methylacetophenone (114 mg, 0.534 mmol), ethanol (3.0 mL), and 1-(2-ethylphenyl)thiourea (87.5 mg, 0.485 mmol) were used to carry out the reaction. After the solution was stirred for 1.5 h and work-up, the residue was purified by Isco Combi-Flash Companion column chromatography (0-5% EtOAc in n-hexane) to give N-(2-ethylphenyl)-4-(4-methylphenyl)-1,3-thiazol-2-amine (115 mg, 81%) as a white solid.

$^1$H NMR (CDCl$_3$, 400 MHz) δ 7.71 (d, 2H), 7.65 (d, 1H), 7.29-7.25 (m, 2H), 7.20 (d, 2H), 7.15 (dd, 1H), 6.71 (s, 1H), 2.70 (q, 2H), 2.37 (s, 3H), 1.26 (t, 3H); LC-MS (APCI) m/z: 295.2 [M+H]$^+$.

EXAMPLE 62

4-(3,4-Dihydro-2H-1,5-benzodioxepin-7-yl)-N-(2-ethylphenyl)-1,3-thiazol-2-amine

Compound 122

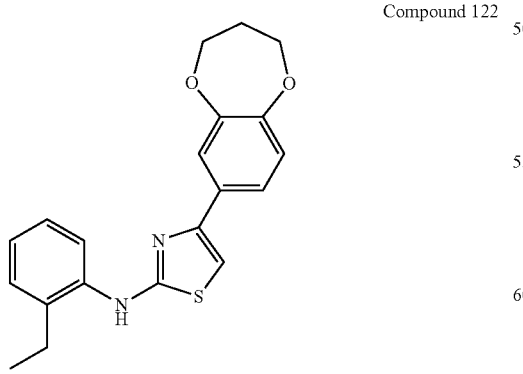

Following the procedure B, 7-bromo-3,4-dihydro-1,5-benzodioxepin (112 mg, 0.413 mmol), ethanol (3.0 mL), and 1-(2-ethylphenyl)thiourea (74.5 mg, 0.413 mmol) were used to carry out the reaction. After the solution was stirred for 6 h and work-up, the residue was purified by Isco Combi-Flash Companion column chromatography (0-30% EtOAc in n-hexane) to give 4-(3,4-dihydro-2H-1,5-benzodioxepin-7-yl)-N-(2-ethylphenyl)-1,3-thiazol-2-amine (96.6 mg, 66%) as a yellow solid.

$^1$H NMR (CDCl$_3$, 300 MHz) δ 7.65 (d, 1H), 7.45 (d, 1H), 7.39 (dd, 1H), 7.35-7.24 (m, 2H), 7.14 (dd, 1H), 7.10 (br s, 1H), 6.99 (d, 1H), 6.65 (s, 1H), 4.24 (t, 4H), 2.69 (q, 2H), 2.21 (quin, 2H), 1.25 (t, 3H); LC-MS (ESI) m/z: 353.1 [M+H]$^+$.

EXAMPLE 63

N-(2-Ethylphenyl)-4-(2-pyridinyl)-1,3-thiazol-2-amine

Compound 123

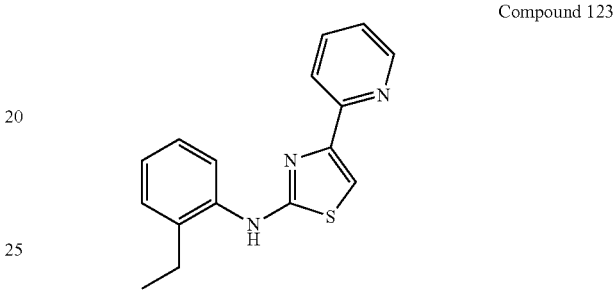

Following the procedure B, 2-bromo-(2-pyridinyl)-1-ethanone hydrobromide (110 mg, 0.391 mmol), ethanol (3.0 mL), and 1-(2-ethylphenyl)thiourea (70.5 mg, 0.391 mmol) were used to carry out the reaction. After the solution was stirred for 18 h and work-up, the crude product was purified by recrystallization with CH$_2$Cl$_2$/diethyl ether to give N-(2-ethylphenyl)-4-(2-pyridinyl)-1,3-thiazol-2-amine (23.7 mg, 22%) as a yellow solid.

$^1$H NMR (CDCl$_3$, 400 MHz) δ 8.61 (d, 1H), 7.94 (d, 1H), 7.74 (dd, 1H), 7.65 (d, 1H), 7.34 (s, 1H), 7.30-7.14 (m, 4H), 2.70 (q, 2H), 1.26 (t, 3H); LC-MS (ESI) m/z: 282.1 [M+H]$^+$.

EXAMPLE 64

N-(2-Ethylphenyl)-4-(2-thiophenyl)-1,3-thiazol-2-amine

Compound 124

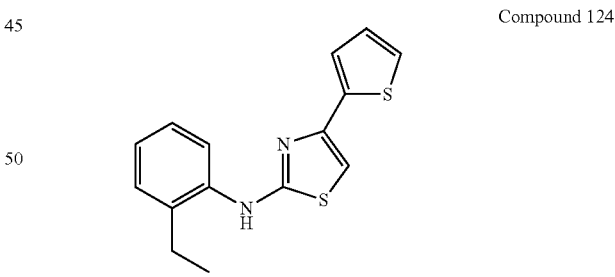

Step 1. 2-Bromo-1-(2-thiophenyl)ethanone

Compound 125

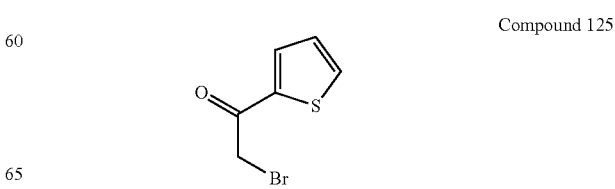

To a solution of 2-acetylthiophene (0.310 g, 2.46 mmol) in 33% of HBr in acetic acid (5.0 mL) was added phenyltrimethylammonium tribromide (0.970 g, 2.58 mmol) at room temperature. After the solution was stirred for overnight, it was poured into ice water and extracted with CH$_2$Cl$_2$. The combined organic layers were dried over MgSO$_{4(s)}$, filtered, and concentrated under reduced pressure to afford a residue. The residue was purified by Isco Combi-Flash Companion column chromatography (0-40% CH$_2$Cl$_2$ in n-hexane) to give 2-bromo-1-(2-thiophenyl)ethanone (0.287 g, 57%) as a brown oil.

$^1$H NMR (CDCl$_3$, 400 MHz) δ 7.81 (d, 1H), 7.72 (d, 1H), 7.17 (dd, 1H), 4.36 (s, 2H).

Step 2. N-(2-Ethylphenyl)-4-(2-thiophenyl)-1,3-thiazol-2-amine

Following the procedure B, 2-bromo-1-(2-thiophenyl)ethanone (94.9 mg, 0.463 mmol), ethanol (3.0 mL), and 1-(2-ethylphenyl)thiourea (83.4 mg, 0.463 mmol) were used to carry out the reaction. After the solution was stirred for 1 h and work-up, the residue was purified by column chromatography (40% EtOAc in n-hexane) to give N-(2-ethylphenyl)-4-(2-thiophenyl)-1,3-thiazol-2-amine (67.2 mg, 51%) as a dark solid.

$^1$H NMR (CDCl$_3$, 300 MHz) δ 7.60 (d, 1H), 7.37 (d, 1H), 7.33-7.20 (m, 3H), 7.16 (dd, 1H), 7.09 (br s, 1H), 7.04 (dd, 1H), 6.65 (s, 1H), 2.69 (q, 2H), 1.27 (t, 3H); LC-MS (ESI) m/z: 287.0 [M+H]$^+$.

EXAMPLE 65

N-(2-Ethylphenyl)-2,4'-bi-1,3-thiazol-2'-amine

Compound 126

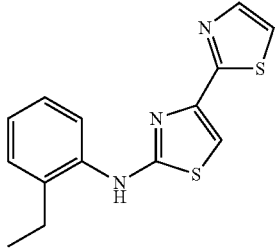

Following the procedure B, 2-bromo-1-(1,3-thiazo-2-yl)ethanone (78.6 mg, 0.381 mmol), ethanol (3.0 mL), and 1-(2-ethylphenyl)thiourea (68.7 mg, 0.381 mmol) were used to carry out the reaction. After the solution was stirred for 3 h and work-up, the residue was purified by Isco Combi-Flash Companion column chromatography (0-30% EtOAc in n-hexane) to give N-(2-ethylphenyl)-2,4'-bi-1,3-thiazol-2'-amine (84.8 mg, 77%) as a yellow solid.

$^1$H NMR (CDCl$_3$, 400 MHz) δ 7.83 (d, 1H), 7.60 (d, 1H), 7.34-7.26 (m, 3H), 7.20 (dd, 1H), 7.08 (br s, 1H), 2.70 (q, 2H), 1.26 (t, 3H); LC-MS (ESI) m/z: 288.0 [M+H]$^+$.

EXAMPLE 66

N-(2-Ethylphenyl)-8H-indeno[1,2-d][1,3]thiazol-2-amine

Compound 127

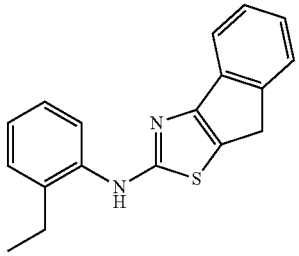

Following the procedure B, 2-bromo-1-indanone (105 mg, 0.498 mmol), ethanol (3.0 mL), and 1-(2-ethylphenyl)thiourea (89.7 mg, 0.498 mmol) were used to carry out the reaction. After the solution was stirred for 3 h and work-up, the residue was purified by Isco Combi-Flash Companion column chromatography (0-40% EtOAc in n-hexane) to give N-(2-ethylphenyl)-8H-indeno[1,2-d][1,3]thiazol-2-amine (48.7 mg, 33%) as a beige solid.

$^1$H NMR (CDCl$_3$, 400 MHz) δ 7.66 (d, 1H), 7.59 (d, 1H), 7.46 (d, 1H), 7.35-7.26 (m, 3H), 7.22-7.18 (m, 2H), 3.72 (s, 2H), 2.71 (q, 2H), 1.26 (t, 3H); LC-MS (ESI) m/z: 293.1 [M+H]$^+$.

EXAMPLE 67

Ethyl 5-{2-[(2-ethylphenyl)amino]-1,3-thiazol-4-yl}-1,2-oxazole-3-carboxylate

Compound 128

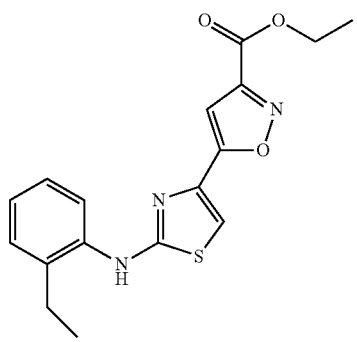

Following the procedure B, ethyl-5-(bromoacetyl)isoxazole-3-carboxylate (106 mg, 0.406 mmol), ethanol (3.0 mL), and 1-(2-ethylphenyl)thiourea (73.2 mg, 0.406 mmol) were used to carry out the reaction. After the solution was stirred for 4 h and work-up, the residue was purified by Isco Combi-Flash Companion column chromatography (0-20% EtOAc in n-hexane) to give ethyl 5-{2-[(2-ethylphenyl)amino]-1,3-thiazol-4-yl}-1,2-oxazole-3-carboxylate (114 mg, 82%) as a yellow solid.

$^1$H NMR (CDCl$_3$, 400 MHz) δ 7.57 (d, 1H), 7.32-7.13 (m, 5H), 6.95 (s, 1H), 4.46 (q, 2H), 2.69 (q, 2H), 1.44 (t, 3H), 1.25 (t, 3H); LC-MS (ESI) m/z: 344.1 [M+H]$^+$.

EXAMPLE 68

N-(2-Ethylphenyl)-4-(3-phenyl-1,2-oxazol-5-yl)-1,3-thiazol-2-amine

Compound 129

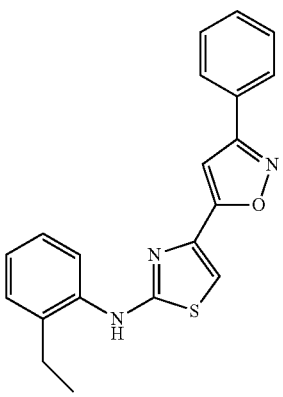

Following the procedure B, 5-(bromoacetyl)-3-phenylisoxazole (101 mg, 0.380 mmol), ethanol (3.0 mL), and 1-(2-ethylphenyl)thiourea (68.4 mg, 0.379 mmol) were used to carry out the reaction. After the solution was stirred for 5 h and work-up, the residue was purified by Isco Combi-Flash Companion column chromatography (0-60% EtOAc in n-hexane) to give N-(2-ethylphenyl)-4-(3-phenyl-1,2-oxazol-5-yl)-1,3-thiazol-2-amine (89.8 mg, 68%) as a white solid.

$^1$H NMR (CDCl$_3$, 400 MHz) δ 7.84 (br s, 2H), 7.59 (d, 1H), 7.56-7.45 (m, 3H), 7.32-7.20 (m, 3H), 7.15 (s, 1H), 6.90-6.82 (m, 1H), 2.70 (q, 2H), 1.25 (t, 3H); LC-MS (ESI) m/z: 348.1 [M+H]$^+$.

EXAMPLE 69

2',4'-Dimethyl-4,5'-bi-1,3-thiazol-2-amine

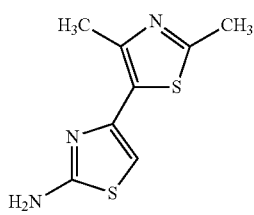

Compound 130

Following the procedure B, 2-bromo-1-(2,4-dimethylthiazol-5-yl)ethanone (92.4 mg, 0.395 mmol), ethanol (3.0 mL), and thiourea (30.1 mg, 0.395 mmol) were used to carry out the reaction. After the solution was stirred for 4 h and work-up, the crude product was washed with a solution of 10% diethyl ether in n-hexane to give 2',4'-dimethyl-4,5'-bi-1,3-thiazol-2-amine (43.9 mg, 53%) as a yellow solid.

$^1$H NMR (DMSO-d$_6$, 400 MHz) δ 7.15 (br s, 2H), 6.62 (s, 1H), 2.54 (s, 3H), 2.44 (s, 3H); LC-MS (ESI) m/z: 212.0 [M+H]$^+$.

EXAMPLE 70

N-(2-Ethylphenyl)-1,3-thiazol-2-amine

Compound 131

A solution of 1-(2-ethylphenyl)thiourea (0.350 g, 1.94 mmol) and bromoacetaldehyde dimethyl acetal (0.330 g, 1.94 mmol) in acetic acid (4.0 mL) was stirred at reflux for 2 h. After the solution was cooled to room temperature, it was quenched by added saturated NaHCO$_{3(aq)}$ and extracted with CH$_2$Cl$_2$. The combined organic layers were dried over MgSO$_{4(s)}$, filtered, and concentrated to afford a residue. The crude product was washed with a solution of 20% diethyl ether in n-hexane to give N-(2-ethylphenyl)-1,3-thiazol-2-amine (0.120 g, 30%) as a yellow solid.

$^1$H NMR (CDCl$_3$, 400 MHz) δ 7.60 (d, 1H), 7.27-7.24 (m, 3H), 7.13 (dd, 1H), 7.10-6.90 (br s, 1H), 6.58 (d, 1H), 2.67 (q, 2H), 1.24 (t, 3H); LC-MS (ESI) m/z: 205.0 [M+H]$^+$.

EXAMPLE 71

N-(2-Ethylphenyl)-4-methyl-1,3-thiazol-2-amine

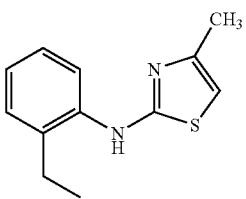

Compound 132

A solution of 1-(2-ethylphenyl)thiourea (0.360 g, 2.00 mmol) and 1-bromo-2,4-dimethoxypropane (0.330 mL, 2.44 mmol) in acetic acid (4.0 mL) was stirred at reflux for 3 h. After the solution was cooled to room temperature and concentrated, it was diluted with EtOAc and washed with water and saturated NaHCO$_{3(aq)}$. The organic layer was dried over MgSO$_{4(s)}$, filtered, and concentrated to afford a residue. The residue was purified by Isco Combi-Flash Companion column chromatography (0-20% EtOAc in n-hexane) to give N-(2-ethylphenyl)-4-methyl-1,3-thiazol-2-amine (0.114 g, 26%) as a yellow solid.

$^1$H NMR (CDCl$_3$, 300 MHz) δ 7.57 (d, 1H), 7.27-7.20 (m, 2H), 7.11 (dd, 1H), 7.05 (br s, 1H), 6.13 (s, 1H), 2.66 (q, 2H), 2.28 (s, 3H), 1.23 (t, 3H); LC-MS (ESI) m/z: 219.0 [M+H]$^+$.

EXAMPLE 72

The exemplary compounds prepared in Examples 1-71 above, as well as others, were tested for modulating opioid receptor activities following the procedures described below.

Cell Culture

Chinese hamster ovary (CHO)-K1 cells expressing hMOR and Gα15 (CHO-K1/MOR/Gα15) were cultured in F12 medium (GIBCO) supplemented with 10 μg/mL Hygromycin B (Invivogen), 20 μg/mL Zeocin (Invivogen) and P/S/F (100 units/mL penicillin, 100 μg/mL streptomycin, 10% fetal bovine serum). The cultures were incubated at 37° C. in a humidified 5% CO$_2$ incubator.

FLIPR® Calcium Assay

One day prior to running the assay, CORNING® black 96-well assay plates having a clear flat bottom were coated with a 0.1 mg/mL Poly-L-Lysine solution. CHO-K1/MOR/Gα15 cells were suspended in F12 medium and plated at a density of about 8×10$^4$ cells/well in 200 μL medium. Cells were incubated under a humidified atmosphere of 10% CO$_2$ at 37° C. overnight to reach an 80-90% confluent cell monolayer before the assay. On the day of the assay, 150 μL medium was removed from each well of the plates. To each well were added FLIPR® calcium assay reagents (Molecular Devices Corporation, Sunnyvale, Calif., USA; 50 μL) dissolved in 1× assay buffer (HBSS: KCl 5 mM, KH$_2$PO$_4$ 0.3 mM, NaCl 138 mM, NaHCO$_3$ 4 mM, Na$_2$HPO4 0.3 mM, d-glucose 5.6 mM, with additional 20 mM HEPES and 13 mM CaCl$_2$, pH 7.4) and 2.5 mM probenecid. After incubation at 37° C. for 1 hour, a test compound, alone or together with naloxone (a MOR antagonist), was also added to each well. Using a FlexStationlll instrument (Molecular Devices Corp.), increments of the [Ca$^{2+}$]$_i$ fluorescence after robotic injection of the cell suspension were monitored at 1.52 s intervals using the excitation wavelength of 485 nm and the emission wavelength of 525 nm. The $[Ca^{2+}]_i$ fluorescence was measured up to 90 s after the injection. The fluorescence intensity from 6 to 12 wells of cells were averaged and the relative amount of $[Ca^{2+}]_i$ release was determined by integrating the AUC of the $[Ca^{2+}]_i$ fluorescence averages.
Identification of Antagonist-to-agonist Allosteric Modifiers (AAMs) of MOR A CHO-K1 cell line expressing MOR and Gα15 (GenScript) was used to set up a sensitive high-throughput screen (HTS) system. In the FLIPR® calcium assay of CHO-K1/MOR/Gα15 cells, activation of MOR elicited an intracellular calcium release, which led to an increase in the relative fluorescence units (FRU). In this system, the $EC_{50}$ value of D-ala2-nmephe4-gly-ol-enkephalin (DAMGO), a MOR-specific agonist, was found to be 0.67 nM. The HTS was performed in the absence or presence of naloxone (an opioid antagonist; 20 nM), to identify AAMs.

Over 135,000 known compounds were screened and compound 1 was one of the active compounds identified with better $EC_{50}$ values. Compound 1 induced a significant calcium release in the presence of naloxone. Co-administered with naloxone (20 nM), Compound 1 induced calcium release in a dose dependent manner. The maximal effect ($E_{max}$) of Compound 1 combined with naloxone was 43% of that of DAMGO, with an $EC_{50}$ value of 4.0 µM.

In addition, concentration-response curves of naloxone in the presence Compound 1 at several concentrations were obtained by the FLIPR® calcium assay. The magnitude of increase in naloxone efficacy at each concentration of Compound 1 was recorded.

It was found that both $E_{max}$ and potency of naloxone were altered by varying the concentration of Compound 1. Compound 1 was also found to be as an AAM of MOR when combined with naltrexone (another MOR antagonist), exerting similar potency but higher efficacy, compared to those from the combination having naloxone.

Characterization of AAMs of MOR

Traditional allosteric modifiers are classified by the mode of target protein activity modulated by modifying compounds. Positive allosteric modifiers (PAMs) enhance the binding affinity or efficacy of an orthosteric agonist when they bind to the receptor; and negative allosteric modifiers (NAMs) inhibit the binding affinity or efficacy of the orthosteric agonist.

Compound 1 was also studied to determine whether it could produce a PAM or NAM effect. Concentration-response curves of morphine, a partial agonist of opioid receptor structurally close to naloxone, were obtained using the FLIPR® calcium assay in the presence or absence of Compound 1.

It was found that neither $E_{max}$ nor potency of morphine was significantly altered by Compound 1 at any tested concentration. Morphine alone produced similar $E_{max}$ as compared to morphine combined with Compound 1 at 30, 10, or 3.3 µM. These results demonstrate that Compound 1 modulated the action of an opiate antagonist without exerting any PAM or NAM effect of the MOR.

Assessment of Seventy One Compounds as AAMs of MOR

Compound 1 and seventy structural analogs thereof (all prepared in Examples 1-71 above) were assessed by both $EC_{50}$ and AUC values using the FLIPR® calcium assay.

All of the seventy one compounds tested in this assay, when combined with naloxone, were found to activate the MOR to different degrees as indicated by their $EC_{50}$ and AUC values shown in the table above. Among these tested compounds, Compounds 1, 17, 29, 33, 45, 47, 49, 70, 85, 95, 102, and 106 each showed an $EC_{50}$ value of lower than 10 µM; and Compounds 1, 4, 14, 17, 21, 29, 33, 35, 43, 47, 53, 55, 65, 85, 95, 102, and 105-107 each showed an AUC value of greater than 5000.

EXAMPLE 73

Naloxone Produced Antinociceptive Effects in Mice Injected with Compound 1 in a Tail-flick Test Male wild-type B6 mice (25-30 g) were kept in a temperature-controlled animal room with a 12-h light/dark cycle. The protocol was approved by the Institutional Animal Care and Use Committee of the National Health Research Institutes, Taiwan. Animal experiments were carried out in accordance with the Policies on the Use of Animals in Neuroscience Research and the ethical guidelines for investigations of experimental pain in conscious animals, International Association for the Study of Pain.

Tail-Flick Analgesia Meter (Columbia Instruments, Trussville, Ala., USA) was used to measure the tail-flick latencies of mice. The cut-off time for each measurement was 10 s to avoid tissue damage. Basal latencies (in seconds) were recorded before treatment and test latencies (also in seconds) were recorded at 30, 60, 90, 120, and 180 minutes after an intravenous injection of compounds. Time-response curves from compounds at various concentrations were obtained for anti-nociceptive effects occurring between 0 and 180 minutes. The AUC values corresponding to the various concentrations were also calculated. The anti-nociceptive effects were quantitatively calculated by substracting the basal latency from the test latency. An $ED_{50}$ value was determined by an up-and-down method reported in Crocker et al., *Pharmacol Biochem Behav*, 1984, 21, 133-136.

To investigate whether AAMs could change the innate character of MOR to be activated by naloxone in vivo, tail-flick tests after acute treatment were performed. Compound 1 alone at 25, 50, or 100 mg/kg (i.v.) did not produce any anti-nociceptive effect in B6 mice. On the other hand, significant inhibition of the tail-flick response was unexpectedly observed in mice injected with both naloxone at 10 mg/kg and Compound 1 at 25, 50, and 100 mg/kg (i.v.), affording AUC values of 114.8±26, 159.8±60, and 384±87 (min×s), respectively. In mice injected with Compound 1 at 100 mg/kg, an $ED_{50}$ value of naloxone in inhibiting the tail-flick response was found to be 17.5±4 mg/kg. Unexpectedly, in mice injected only with the vehicle not containing naloxone, no anti-nociception effect was observed even with the highest dose of Compound 1 at 100 mg/kg. These in vivo results again indicate that Compound 1 served as an AAM of the MOR.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A pharmaceutical composition for treating an opioid receptor-associated condition, the pharmaceutical composition comprising a pharmaceutically acceptable carrier, a mu-opioid receptor antagonist, and a compound of Formula (I):

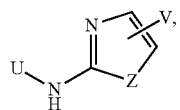

(I)

wherein
U is H, $C_{1-6}$ alkyl, $C_{3-8}$ cycloalkyl, $C_{2-8}$ heterocycloalkyl, $C_{6-14}$ aryl, or $C_{1-13}$ heteroaryl;
V is H, $C_{1-6}$ alkyl, $C_{3-8}$ cycloalkyl, $C_{2-8}$ heterocycloalkyl, or $C_{1-13}$ heteroaryl; and
Z is O or S,
in which
each of $C_{1-6}$ alkyl, $C_{3-8}$ cycloalkyl, $C_{2-8}$ heterocycloalkyl, $C_{6-14}$ aryl, and $C_{1-13}$ heteroaryl, independently, is optionally mono-, di-, or tri-substituted with halo, OH, CN, $NH_2$, $NO_2$, COOH, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, —C(O)OR, —C(O)NRR', —NRC(O)R', —S(O)$_2$R, —S(O)$_2$NRR', —NRS(O)$_2$R', —C(O)R, or —NRS(O)$_2$NR'R''; or is optionally fused with $C_{3-8}$ cycloalkyl, $C_{2-8}$ heterocycloalkyl, $C_{6-14}$ aryl, or $C_{1-13}$ heteroaryl; each of R, R', and R'', independently, being H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, $C_{6-14}$ aryl, or $C_{1-13}$ heteroaryl.

2. The pharmaceutical composition of claim 1, wherein U is

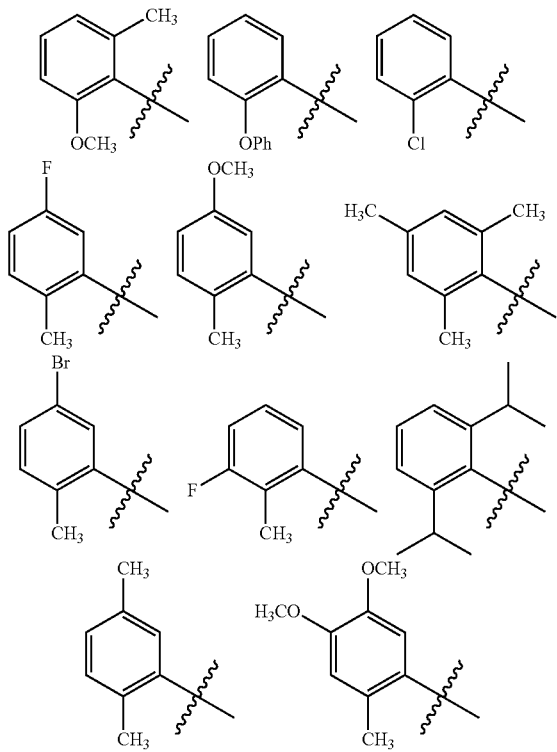

-continued

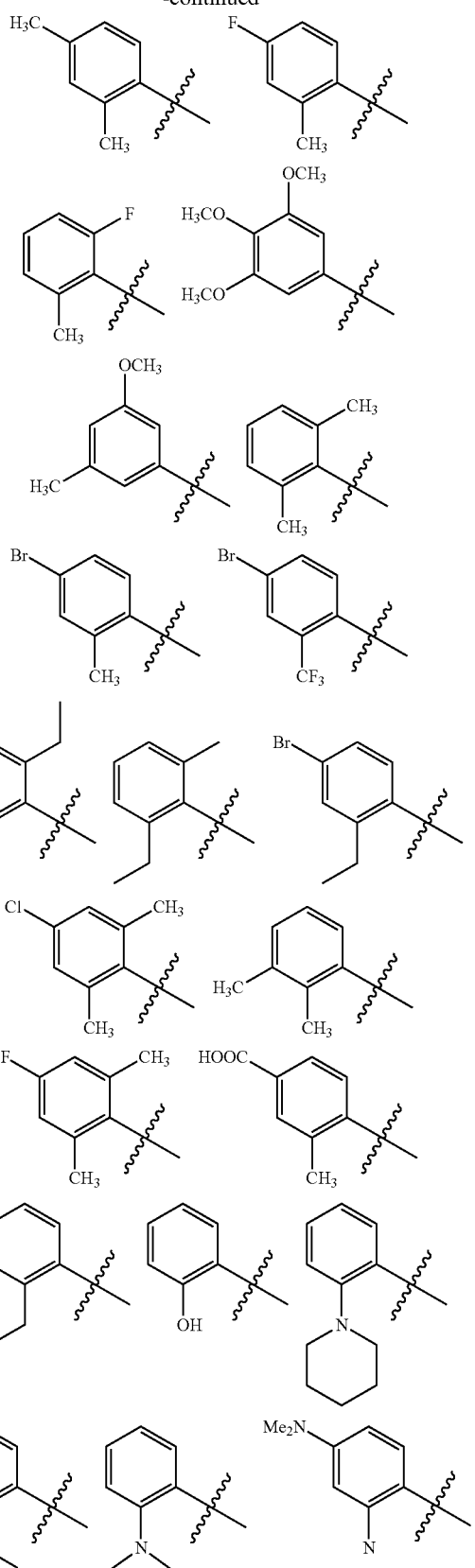

-continued

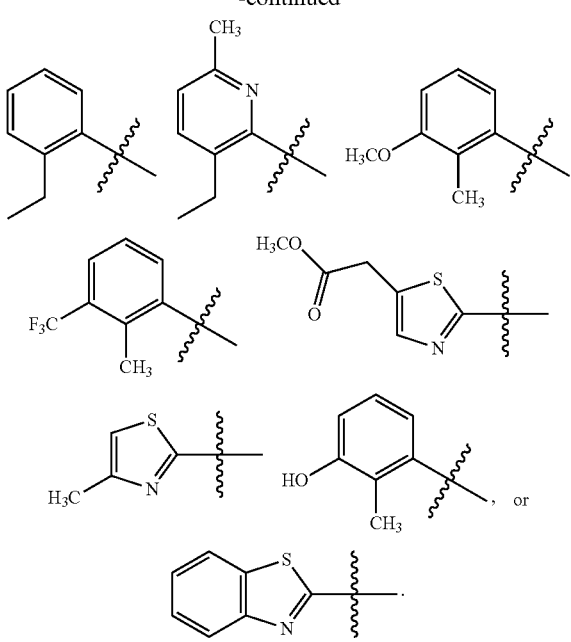

3. The pharmaceutical composition of claim 2, wherein V is

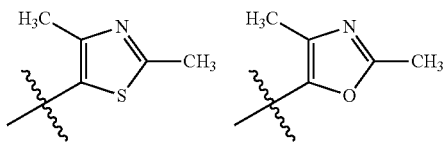

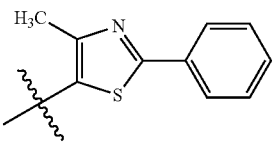

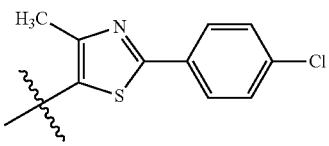

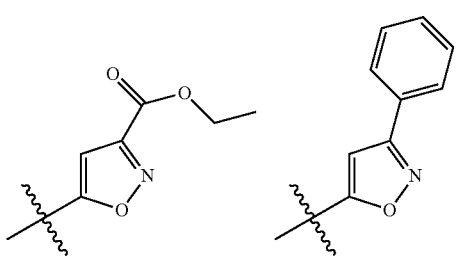

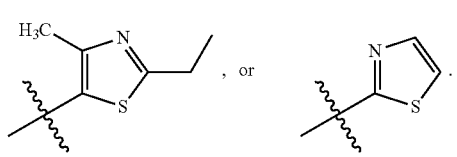

4. The pharmaceutical composition of claim 1, wherein V is

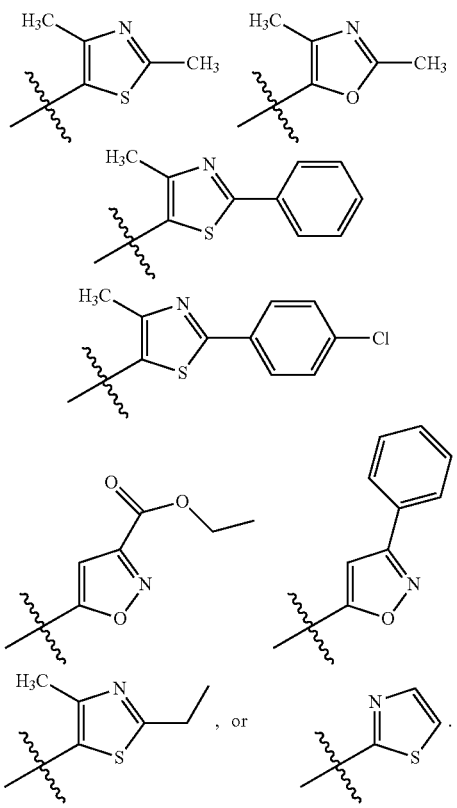

5. The pharmaceutical composition of claim 1, wherein the compound is one of Compounds 1, 4, 6, 8, 10, 12, 17, 19, 21, 23, 25, 27, 29, 31, 33, 35, 37, 39, 41-43, 45, 47, 49, 51, 53, 55, 57, 62, 65, 68, 70, 72, 75, 82, 85, 87, 89, 92, 93-95, 98, 102, 105-107, 109, 111, 114, 117, 126, 128, 129, 131, and 132.

6. The pharmaceutical composition of claim 5, wherein the opioid receptor-associated condition is pain, and the mu-opioid receptor antagonist is naloxone, naltrexone, or samidorphan.

7. The pharmaceutical composition of claim 6, wherein the compound is one of Compounds 1, 17, 29, 33, 47, 85, 95, 102, and 106.

8. The pharmaceutical composition of claim 7, wherein the compound is Compound 1.

9. The pharmaceutical composition of claim 1, wherein the mu-opioid receptor antagonist is naloxone, naltrexone, or samidorphan.

10. The pharmaceutical composition of claim 1, wherein the opioid receptor-associated condition is pain, immune disease, esophageal reflux, diarrhea, anxiety, heroin addiction, or cough.

11. The pharmaceutical composition of claim 10, wherein the opioid receptor-associated condition is pain.

12. A method of treating an opioid receptor-associated condition, the method comprising administering to a subject in need thereof a pharmaceutical composition of claim 8, wherein the pharmaceutical composition contains a mu-opioid receptor antagonist and an effective amount of a compound of Formula (I):

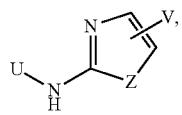
(I)

wherein
U is H, $C_{1-6}$ alkyl, $C_{3-8}$ cycloalkyl, $C_{2-8}$ heterocycloalkyl, $C_{6-14}$ aryl, or $C_{1-13}$ heteroaryl;
V is H, $C_{1-6}$ alkyl, $C_{3-8}$ cycloalkyl, $C_{2-8}$ heterocycloalkyl, or $C_{1-13}$ heteroaryl; and
Z is O or S,
in which
each of $C_{1-6}$ alkyl, $C_{3-8}$ cycloalkyl, $C_{2-8}$ heterocycloalkyl, $C_{6-14}$ aryl, and $C_{1-13}$ heteroaryl, independently, is optionally mono-, di-, or tri-substituted with halo, OH, CN, $NH_2$, $NO_2$, COOH, $C_{1-6}$ alkyl, $C_{1-6}$ haloalkyl, $C_{2-6}$ alkenyl, $C_{3-8}$ cycloalkyl, $C_{2-8}$ heterocycloalkyl, $C_{1-6}$ alkoxy, $C_{1-6}$ haloalkoxy, $C_{1-6}$ alkylamino, $C_{2-6}$ dialkylamino, $C_{7-12}$ aralkyl, $C_{1-12}$ heteroaralkyl, —C(O)OR, —C(O)NRR', —NRC(O)R', —S(O)$_2$R, —S(O)$_2$NRR', —NRS(O)$_2$R', —C(O)R, or —NRS(O)$_2$NR'R"; or is optionally fused with $C_{3-8}$ cycloalkyl, $C_{2-8}$ heterocycloalkyl, $C_{6-14}$ aryl, or $C_{1-13}$ heteroaryl; each of R, R', and R", independently, being H, halo, OH, $C_{1-6}$ alkyl, $C_{1-6}$ haloalkyl, $C_{1-6}$ alkoxy, $C_{3-8}$ cycloalkyl, $C_{2-8}$ heterocycloalkyl, $C_{6-14}$ aryl, or $C_{1-13}$ heteroaryl,
or a pharmaceutically acceptable salt of the compound.

13. The method of claim 12, wherein the mu-opioid receptor antagonist is naloxone, naltrexone, or samidorphan.

14. The method of claim 12, wherein the opioid receptor-associated condition is pain, immune disease, esophageal reflux, diarrhea, anxiety, heroin addiction, or cough.

15. The method of claim 14, wherein the opioid receptor-associated condition is pain.

16. The method of claim 15, wherein the compound is Compound 1, 17, 29, 33, 47, 85, 95, 102, or 106.

17. The method of claim 16, wherein the compound is Compound 1.

18. The method of claim 15, wherein the pain is renal colic, acute pancreatitis, angina, chronic neuropathic pain, chronic regional complex pain syndrome, or cancer pain.

* * * * *